US011360087B2

(12) United States Patent
Basso-Ricci et al.

(10) Patent No.: US 11,360,087 B2
(45) Date of Patent: Jun. 14, 2022

(54) USES, METHODS, KITS, COMPOSITIONS AND ANTIBODIES FOR IDENTIFYING HEMATOPOIETIC CELL SUBTYPES

(71) Applicants: Ospedale San Raffaele S.R.L., Milan (IT); Fondazione Telethon, Rome (IT)

(72) Inventors: Luca Basso-Ricci, Milan (IT); Luca Biasco, Milan (IT); Alessandro Aiuti, Milan (IT)

(73) Assignees: Ospedale San Raffaele S.R.L., Milan (IT); Fondazione Telethon, Rome (IT)

( * ) Notice: Subject to any disclaimer, the term of this patent is extended or adjusted under 35 U.S.C. 154(b) by 98 days.

(21) Appl. No.: 16/342,354

(22) PCT Filed: Oct. 17, 2017

(86) PCT No.: PCT/EP2017/076517
§ 371 (c)(1),
(2) Date: Apr. 16, 2019

(87) PCT Pub. No.: WO2018/073267
PCT Pub. Date: Apr. 26, 2018

(65) Prior Publication Data
US 2020/0182870 A1 Jun. 11, 2020

(30) Foreign Application Priority Data
Oct. 17, 2016 (GB) .................................... 1617572

(51) Int. Cl.
*G01N 33/569* (2006.01)
*G01N 1/28* (2006.01)
(Continued)

(52) U.S. Cl.
CPC ......... *G01N 33/56966* (2013.01); *G01N 1/28* (2013.01); *G01N 15/1459* (2013.01);
(Continued)

(58) Field of Classification Search
CPC ......... G01N 33/56966; G01N 33/4915; G01N 33/56972; G01N 33/582
See application file for complete search history.

(56) References Cited

U.S. PATENT DOCUMENTS

| 9,880,158 B2* | 1/2018 | Van Dongen ........ G01N 33/532 |
| 2012/0165213 A1* | 6/2012 | van Dongen ...... G01N 33/5091 506/9 |
| 2018/0052166 A1* | 2/2018 | Villalba Gonzalez ...................... G01N 33/57484 |

FOREIGN PATENT DOCUMENTS

| WO | 2009146495 A1 | 12/2009 |
| WO | 2010140885 A1 | 12/2010 |
| WO | 2011041912 A1 | 4/2011 |

OTHER PUBLICATIONS

Porwit et al. Flow cytometry immunophenotyping in integrated diagnostics of patients with newly diagnosed cytopenia: one tube 10-color 14-antibody screening panel and 3-tube extensive panel for detection of MDS-related features, International Journal of Laboratory Hematology. 37: 133-143 (2015).*

(Continued)

*Primary Examiner* — Gailene Gabel
(74) *Attorney, Agent, or Firm* — Grimes & Yvon LLP

(57) ABSTRACT

Use of (i) an anti-CD3 antibody, (ii) an anti-CD56 antibody, (iii) an anti-CD14 antibody, (iv) an anti-CD38 antibody, (v) an anti-CD45 antibody, (vi) an anti-CD90 antibody, (vii) an anti-CD135 antibody, (viii) an anti-CD10 antibody, (ix) an anti-CD11c antibody, (x) an anti-CD19 antibody, (xi) an anti-CD34 antibody, (xii) an anti-CD45RA antibody, (xiii) an anti-CD7 antibody, (xiv) an anti-CD71 antibody, (xv) an anti-CD41/CD61 complex antibody or an anti-CD41 antibody and/or an anti-CD61 antibody (xvi) an anti-CD33 antibody and/or an anti-CD66b antibody, for identifying hematopoietic cell subtypes in an isolated sample, determin- (Continued)

ing the relative frequency of hematopoietic cell subtypes in an isolated sample and/or quantifying the number of cells within hematopoietic cell subtypes in an isolated sample, wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD4 antibody and the anti-CD61 antibody are labelled with the same fluorochrome.

6 Claims, 45 Drawing Sheets

(51) Int. Cl.
G01N 15/14 (2006.01)
G01N 33/58 (2006.01)
G01N 33/49 (2006.01)

(52) U.S. Cl.
CPC ... *G01N 33/4915* (2013.01); *G01N 33/56972* (2013.01); *G01N 33/582* (2013.01)

(56) References Cited

OTHER PUBLICATIONS

Mateo et al. Platelet activation markers with anti-CD41/61 monoclonal antibodies. Veterinary Immunology and Immunopathology. 52: 357-362 (1996).*
Marini et al. Identification of granulocytic-myeloid-derived suppressor cells (G-MDCs) in the peripheral blood of Hodgkin and non-Hodgkin lymphoma patients. Oncotarget 7 (19): 27676-27687 (Mar. 30, 2016).*
Apasov S G, M. R. Blackburn; R. E. Kellems; P. T. Smith; M. V Sitkovsky, "Adenosine deaminase deficiency increases thymic apoptosis and causes defective T cell receptor signaling", J.Clin.Invest, (20010000), vol. 108, pp. 131-141.
Beckton Dickinson Biosciences, BD Horizon Brilliant™ Ultraviolet Reagents, 2014.
BioLegend, PE/Cy7 anti-human CD41/CD61 Product Data Sheet, Oct. 1, 2014.
Bhojwani D, J. J. Yang; C.-H. Pui, "Biology of Childhood Acute Lymphoblastic Leukemia", Pediatr. Clin. North Am., (2015), vol. 62, pp. 47-60.
Brigida I. A. V Sauer; F. Ferrua; S. Giannelli; S. Scaramuzza; V. Pistoia; M. C. Castiello; B. H. Barendregt; M. P. Cicalese; M., "B-cell development and functions and therapeutic options in adenosine deaminase-deficient patients", J. Allergy Clin. Immunol., (2014), vol. 133, pp. 799-806.
Cham B; M. A. Bonilla; J. Winkelstein, "Neutropenia associated with primary immunodeficiency syndromes", Semin. Hematol., (2002), vol. 39, pp. 107-112.
Chattopadhyay P K et al., Brilliant Violet Fluorophoes: a new class of ultrabright fluorescent compounds for immunofluorescence experiments, Cytometry Part A, (20120000), vol. 81A, pp. 456-466.
Craig F E, K. A. Foon, "Flow cytometric immunophenotyping for hematologic neoplasms", Blood, (2008), vol. 111, doi:doi:10.1182/BLDOD-2007-11-120535, pp. 3941-3967, XP002538070.
De Kouchkovsky I, M. Abdul-Hay, "Acute myeloid leukemia: a comprehensive review and 2016 update", Blood Cancer Journal, (2016), vol. e441, pp. 1-10.
Hofman E et al., Structural Basis of Light Harvesting by Carotenoids: Peridinin-Chlorophyll-Protein from Amphidinium carterae. Science, (1996), vol. 272, pp. 1788-1791.
Hudson P J and Kortt A A, High avidity scFv multimers; diabodies and triabodies, J Immunol Methods, (1999), vol. 231, No. 1, pp. 177-189.

Jabbour E, S. O'Brien; M. Konopleva; H. Kantarjian, "New Insights into the Pathophysiology and Therapy of Adult Acute Lymphoblastic Leukemia", Cancer, (2015), pp. 2517-2528.
Jacob M-C et al., "One tube with eight antibodies for 14-part bone marrow leukocyte differential using flow cytometry : Bone Marrow Cells and Flow Cytometry", Cytometry. Part B, Clinical Cytometry, US, (Mar. 14, 2016), vol. 92, No. 4, doi:10.1002/cyto.b.21369, ISSN 1552-4949, pp. 299-309, XP055438144.
Lavis L D and Raines, Bright ideas for Chemical Biology, ACS Chem Biol, (2008), vol. 3, No. 3, pp. 142-155.
Massaad M J,; N. Ramesh; R. S. Geha, "Wiskott-Aldrich syndrome: A comprehensive review", Ann. N. Y. Acad. Sci., (2013), vol. 1285, pp. 26-43.
Ochs H D, S. J. Slighter; L. A. Harker; W. E. Von Behrensm; R. A. Clark; R. J. Wedgwood, "The Wiskott-Aldrich Syndrome: Studies of Lymphocytes, Granulocytes, and Platelets", Blood, (1980), vol. 55, pp. 243pp-p. 252.
O'Donnell M R, C. N. Abboud; J. Altman; F. R. Appelbaum; D. A. Arber; E. Attar; U. Borate; S. E. Coutre; L. E. Damon; S. Goorha, "Acute Myeloid Leukemia", Natl. Compr. Cancer Netw., (2012), vol. 10, pp. 984-1021.
Oliveira E; T. S. Bacelar; J. Ciudad; M. C. M. Ribeiro; D. R. N. Garcia; L. Sedek; S. F. Maia; D. B. Aranha; I. C. Machado; A. Ik, "Altered neutrophil immunophenotypes in childhood B-cell precursor acute lymphoblastic leukemia", Oncotarget, (2016), vol. 7, pp. 24664-24676.
Ornatsky O et al., 2010. Highly multiparametric analysis by mass cytometry, Journal of Immunological Methods 361 (2010) 1-20.
Park J Y, M. Kob; A. P. Prodeus; F. S. Rosen; A. Shcherbina; E. Remold-O'Donnell, "Early deficit of lymphocytes in Wiskott-Aldrich syndrome: Possible role of WASP in human lymphocyte maturalion", Clin. Exp. Immunol., (2004), vol. 136, pp. 104-110.
Perfetto S P et al., Seventeen-colour flow cytometry: unravelling the immune system, Nature Reviews Immunology 2004 vol. 4, pp. 648-655.
Poljak, Structure, Production and structure of diabodies, (1994), vol. 2, No. 12, pp. 1121-1123.
Porwit A and A. Rajab, "Flow cytometry immunophenotyping in integrated diagnostics of patients with newly diagnosed cytopenia: one tube 10-color 14-antibody screening panel and 3-tube extensive panel for detection of MDS-related features", International Journal of Laboratory Hematology, 2015, vol. 37, pp. 133-143.
Resch-Genger, Quantum dots versus organic dyes as fluorescent labels, Nature Methods, 2008, vol. 5, pp. 763-775.
Rondon I J and Marasco W A, "Intracellular antibodies (intrabodies) for gene therapy of infectious diseases", Annual Review of Microbiology, (1997), vol. 21, pp. 257-283.
Sauer A V, H. Morbach; I. Brigida; Y. Ng; A. Aiuti; E. Meffre, Defective B cell tolerance in adenosine deaminase deficiency is corrected by gene therapy, (2012), vol. 122, pp. 2141-2152.
Simon K L, S. M. Anderson; E. K. Garabedian; D. Moratto; R. A. Sokolic; F. Candotti, "Molecular and phenotypic abnormalities of B lymphocytes in patients with Wiskott-Aldrich syndrome.", J. Allergy Clin. Immunol., (2014), vol. 133, pp. 896-899.e4.
Skotheim T A and Reynolds J R (editors), "Chapters 14, 17 and 22", Handbook of Conducting Polymers, 2006, 3rd edition, CRC Press.
Todorovska A et al., Design and application of diabodies, triabodies and tetrabodies for cancer targeting, J Immunol Methods, (2001), vol. 248, No. 1, pp. 47-66.
Van Dongen J J M et al., EuroFlow antibody panels for standardize n-dimensional flow cytometric mmunophenotyping of normal, reactive and malignant leukocytes, EuroFlow™ antibody panels, Handout at 14th EHA Congress, Berlin, DE. Jun. 4, 2009.
Van Lochem E G et al., "Immunophenotypic differentiation patterns of normal hematopoiesis in human bone marrow Reference patterns for age-related changes and disease-induced shifts", Cytometry. Part B, Clinical Cytometry, Wiley-Liss, Hoboken, NJ, US, (Jun. 14, 2004), vol. 60, No. 1, ISSN 1552-4949, pp. 1-13, XP002364966.
Basso-Ricci L et al., "Multiparametric Whole Blood Dissection: A one-shot comprehensive picture of the human hematopoietic system : Multiparametric immunophenotyping of human

(56) References Cited

OTHER PUBLICATIONS hematopoiesis", Cytometry. Part A, US, (Jun. 13, 2017), vol. 91, No. 10, doi:10.1002/cyto.a.23148, ISSN 1552-4922, pp. 952-965, XP055438131.

Karawajew L et al., "Minimal residual disease analysis by eight-color flow cytometry in relapsed childhood acute ymphoblastic leukemia, Haematologica", Hematologica, (20150601), vol. 100, pp. 935-944 URL: http://www.haematologica.org/content/100/7/935, (Jan. 4, 2018), XP055438273.

Van Dongen J J M et al., EuroFlow antibody panels for standardized n-dimensional flow cytometric immunophenotyping of normal, reactive and malignant leukocytes, Leukemia, 2012, vol. 26, pp. 1908-1975.

Hunger S P; C. G. Mullighan, "Acute Lymphoblastic Leukemia in Children", N. Engl. J. Med., (2015), vol. 373, pp. 1541-1552.

Malergue F et al., Simplified and More Accurate Surface + Intracellular Staining Experiments by Flow Cytometry, Beckman Coulter poster, Table 2, (2014).

\* cited by examiner

| Marker-Fluorochrome | | | | |
|---|---|---|---|---|
| Sorting 1 | Sorting 2 | Sorting 3 | Sorting 4 | Sorting 5 |
| CD45 APC | CD45 APC | CD45 APC | CD45 APC | CD45 APC |
| CD33 CD66b BB515 | CD33 CD66b BB515 | CD33 CD66b BB515 | CD33 CD66b BB515 | CD33 CD66b BB515 |
| CD3 PE | CD3 PE | CD11c PE | CD14 BV510 | CD3 PE |
| CD56 Pe-Cy5 | CD19 APC-R700 | CD10 Pe-Cy7 | CD11c PE | CD19 APC-R700 |
| CD19 APC-R700 | CD10 Pe-Cy7 | CD14 BV510 | CD34 BV421 | CD56 Pe-Cy5 |
| | CD34 BV421 | | CD41/61 Pe-Cy7 | CD34 BV421 |
| | | | CD71 APC-H7 | CD71 APC-H7 |
| | | | | CD41/61 Pe-Cy7 |
| | | | | CD10 PE-DAZZLE594 |
| | | | | CD7 BV510 |

FIG. 2A

USES, METHODS, KITS, COMPOSITIONS AND ANTIBODIES FOR IDENTIFYING HEMATOPOIETIC CELL SUBTYPES

CROSS-REFERENCE TO RELATED APPLICATIONS

This application is the national stage of International Application No. PCT/EP2017/076517, filed on Oct. 17, 2017, which claims the benefit of priority to Great Britain Application No. 1617572.1, filed on Oct. 17, 2016.

FIELD OF THE INVENTION

The present invention relates to the use of fluorochrome labelled antibodies for identifying, determining the relative frequency of and/or quantifying the number of cells within hematopoietic cell subtypes in an isolated sample.

BACKGROUND TO THE INVENTION

The haematopoietic system is a complex hierarchy of cells of different mature cell lineages found in the blood, including cells of the immune system that offer protection from pathogens, cells that carry oxygen through the body and cells involved in wound healing. These mature cells are derived from a pool of haematopoietic stem cells (HSC) that are capable of self-renewal and differentiation into any hematopoietic cell lineage in a process termed haematopoiesis. Together, there are over twenty distinct types of hematopoietic cells—including fully differentiated mature cells types, partially differentiated progenitor and immature cells and undifferentiated multipotent stem cells.

Human hematopoiesis is the process by which a hierarchically organized system of distinct hematopoietic cells with disparate properties and characteristics are continuously generated from primitive hematopoietic progenitors, which mainly reside in the bone marrow (BM). The fine regulation of this complex system allows the maintenance of its important functions, as blood coagulation, oxygen/metabolite transport and pathogen/viral clearance.

Several pathological conditions such as immunodeficiencies and tumours can cause alterations in the differentiation path of the hematopoietic cells, leading to an unbalanced frequency of immature vs. mature cell types or to aberrant cell phenotypes (1-13).

For example, primary immune deficiencies (PID) are inherited genetic disorders affecting distinct components of the innate and adaptive immune system, such as neutrophils, macrophages, dendritic cells, complement proteins, natural killer cells, T-cells and B-cells leading to impairment of cell differentiation and/or function.

Abnormal hematopoiesis can also result from the aberrant expansion of transformed hematopoietic cells. Acute lymphoblastic leukemia (ALL) is a genetic heterogeneous disorder, mostly affecting children, that leads to the accumulation of immature blasts bearing a lymphoid precursors-like phenotype (12-15). Acute myeloid leukemia (AML) is the most common acute leukemia in adults. In contrast to ALL, AML leukemic blasts display more heterogeneous myeloid phenotype having the ability to proliferate and partially differentiate (11, 16). In ALL and AML leukemic blasts dominate the BM compartment with profound suppression of other hematopoietic lineages, leading to severe unbalances in the relative frequency of hematopoietic cell types and peripheral blood (PB) cytopenia (1, 2, 11, 13, 15).

Morphological examination is one of the routine laboratory tests performed for the diagnosis of blood disorders, e.g. hematopoietic/immunological disorders or blood cancers, where alterations of the physiological differentiation of hematopoietic cells is suspected (1, 17, 18). However, this test requires experienced investigators and is time consuming. Moreover, this test has limitations for cell quantification and presents difficulties when attempting to identify rare hematopoietic cell subtypes.

As an alternative to examining cell morphology, the analysis of lineage-specific molecular markers on the surface of hematopoietic cells provides more quantitative and reproducible results. In this approach, cells are distinguished on the basis of differential expression of surface markers e.g. CD34, CD38 and C45RA. The particular combination of cell surface markers characteristic of a certain cell type is known as the cell's immunophenotype. Thus, by simultaneously measuring multiple fluorescently labelled antibodies each binding a specific surface marker, flow cytometry can be used for high-resolution classification and quantification of different cell types based on immunophenotype. A major challenge associated with so-called multi-colour flow cytometry is spectral overlap of the light emitted by the multiple fluorochromes.

In view of the problem of spectral overlap, most flow cytometers presently in use in the laboratory are limited to ten simultaneous measurements, corresponding to the detection of eight different fluorescent labels and two physical parameters. Since there are over twenty different subtypes of hematopoietic cell, some of which can only be distinguished by differential expression of a single maker, the use of up to eight independent markers is insufficient to identify all of the different hematopoietic cell subtypes in a whole blood sample. Accordingly, at present it is not possible to assess the relative frequency of all different hematopoietic cell subtypes in a single sample by flow cytometry.

Instead analysis of hematopoietic cells by flow cytometry currently requires splitting the available biological sample into different test tubes, each of which is then used to analyse a restricted group of hematopoietic cell subtypes based upon expression of a limited set of surface markers. For example, Dongen et al (EuroFlow™ antibody panels (2009) Handout at 14$^{th}$ EHA Congress, Berlin) have developed a number of panels of fluorescently labelled antibodies that can be used to identify particular cell type of interest.

WO2011/041912 describes seven colour flow cytometric analyses of HSC-enriched samples prepared by either CD34$^+$ selection or depletion of Lin$^+$ cells. However, this approach is associated with the requirements for a larger amount of starting material since there will be loss during the cell isolation process. In addition, the introduction of this additional step increases cost and time burdens.

Perfetto et al (2004 Nat Rev Immunol 4:648-655) have reported on the development of a multi-colour flow cytometry set up that can be used to detect up to 17 distinct fluorescent signals. However, this earlier protocol could not discriminate progenitor cells and therefore its application could not be extended to BM samples.

Mass spectrometry-based flow cytometry (mass cytometry) has also been developed to allow the simultaneous study of a large number of different cell markers (Ornatsky et al). This technology exploits heavy metal isotopes conjugated to molecules that are linked to antibodies. However, mass cytometry requires extensive optimization of panel design. Furthermore, the high cost of the instrumentation, the need for specialized personnel and the time consuming nature of the technique limit its application for routine laboratory tests.

Accordingly, there remains a need for new and improved methods for determining the relative frequency of all the different hematopoietic cell subtypes present in a sample.

SUMMARY OF THE INVENTION

The present inventors have devised a panel of fluorochrome-labelled antibodies that can be used to identify hematopoietic cell subtypes in an isolated sample, determine the relative frequency of and/or quantify the number of cells within hematopoietic cell subtypes in a sample. Importantly, the combination of cell surface markers arrived at by the present inventors allows a blood sample to be labelled without division into sub-samples or the prior isolation of a cell subpopulation of interest. Moreover, the present invention provides superior coverage of the various hematopoietic cell subtypes present in blood making it possible to discriminate 23 different hematopoietic cell subtypes.

The ability to determine relative frequencies of and quantify the number of cells within hematopoietic cell subtypes in a sample may be used in the diagnosis of blood disorders. For example, determination of relative frequencies of hematopoietic cell subtypes allows the identification of unbalanced distribution of cells among the different cell compartments. Moreover, absolute cell quantification allows the testing of whether each cell compartment is within the normal range of cellularity.

Thus, in a first aspect, the present invention provides use of (i) an anti-CD3 antibody, (ii) an anti-CD56 antibody, (iii) an anti-CD14 antibody, (iv) an anti-CD38 antibody, (v) an anti-CD45 antibody, (vi) an anti-CD90 antibody, (vii) an anti-CD135 antibody, (viii) an anti-CD10 antibody, (ix) an anti-CD11c antibody, (x) an anti-CD19 antibody, (xi) an anti-CD34 antibody, (xii) an anti-CD45RA antibody, (xiii) an anti-CD7 antibody, (xiv) an anti-CD71 antibody, (xv) an anti-CD41/CD61 complex antibody or an anti-CD41 antibody and/or an anti-CD61 antibody (xvi) an anti-CD33 antibody and/or an anti-CD66b antibody, for identifying hematopoietic cell subtypes in an isolated sample, determining the relative frequency of hematopoietic cell subtypes in an isolated sample and/or quantifying the number of cells within hematopoietic cell subtypes in an isolated sample, wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome.

An anti-CD41/CD61 complex antibody is an antibody immunospecific for the CD41/CD61 complex.

Thus, in one embodiment, (xv) is an anti-CD41/CD61 complex antibody. In another embodiment, (xv) is an anti-CD41 antibody. In another embodiment, (xv) is an anti-CD61 antibody. In another embodiment, (xv) is an anti-CD41 antibody and an anti-CD61 antibody wherein the anti-CD41 antibody and the anti-CD61 antibody are labelled with the same fluorochrome.

In one embodiment, (xvi) is an anti-CD33 antibody. In another embodiment, (xvi) is an anti-CD66b antibody. In another embodiment, (xvi) is an anti-CD33 antibody and an anti-CD66b antibody wherein the anti-CD33 antibody and anti-CD66b are labelled with the same fluorochrome In one embodiment there is provided use of (i) an anti-CD3 antibody, (ii) an anti-CD56 antibody, (iii) an anti-CD14 antibody, (iv) an anti-CD38 antibody, (v) an anti-CD45 antibody, (vi) an anti-CD90 antibody, (vii) an anti-CD135 antibody, (viii) an anti-CD10 antibody, (ix) an anti-CD11c antibody, (x) an anti-CD19 antibody, (xi) an anti-CD34 antibody, (xii) an anti-CD45RA antibody, (xiii) an anti-CD7 antibody, (xiv) an anti-CD71 antibody, (xv) an anti-CD41/CD61 complex antibody (xvi) an anti-CD33 antibody and an anti-CD66b antibody, for identifying hematopoietic cell subtypes in an isolated sample, determining the relative frequency of hematopoietic cell subtypes in an isolated sample and/or quantifying the number of cells within hematopoietic cell subtypes in an isolated sample, wherein each of (i) to (xvi) is labelled with a different fluorochrome, wherein the anti-CD33 antibody and the anti-CD66b antibody are labelled with the same fluorochrome, In one embodiment, the use according to the present invention is for identifying, determining the relative frequency of and/or quantifying the number of cells within one or more hematopoietic cell subtypes selected from the group consisting of immature polymorphonuclear leukocytes (iPMN), polymorphonuclear leukocytes (PMN), monocytes, dendritic cells (DC)/DC progenitors, myeloblasts, T-cells, natural killer T cells (NKT), natural killer cells (NK), B-cells, pre-B cells, pro-B cells, pro-lymphocytes, pro-erythroblasts, erythroblasts, hematopoietic stem cells (HSC), multipotent progenitors (MPP), multipotent lymphoid progenitors (MLP), early T progenitors (ETP) cells, pre-B/natural killer cells (PRE-B/NK), common myeloid progenitors (CMP), granuclocyte/macrophage progenitors (GMP), and megakaryocyte/erythrocyte progenitors (MEP).

In another aspect, the present invention provides use of (B-i) an anti-CD3 antibody, (B-ii) an anti-CD56 antibody, (B-iii) an anti-CD45 antibody, (B-iv) an anti-CD19 antibody, (B-v) an anti-CD45RA antibody, (B-vi) an anti-CD33 antibody and/or an anti-CD66b antibody, (B-vii) an anti-CD4 antibody, (B-viii) an anti-CD8 antibody, (B-ix) an anti-CD95 antibody, (B-x) an anti-TCRγδ antibody, (B-xi) an anti-CD127 antibody, (B-xii) an anti-CD62L antibody, (B-xiii) an anti-CD25 antibody, for identifying lymphoid cell subtypes in an isolated sample, determining the relative frequency of lymphoid cell subtypes in an isolated sample and/or quantifying the number of cells within lymphoid cell subtypes in an isolated sample, wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome.

The panel of markers (B-i)-(B-xiii) may be used in combination with the panel of markers (i)-(xvi) (e.g. using different aliquots of the same sample) to provide detailed analysis of lymphoid cells that may be coupled with the comprehensive analysis enabled by markers (i)-(xvi). As the two panels of markers may be used with the same initial steps of a gating strategy, the information obtained from the two analyses may be merged. Alternatively, analysis using markers (B-i)-(B-xiii) may be carried out independently.

In one embodiment, (B-vi) is an anti-CD33 antibody. In another embodiment, (B-vi) is an anti-CD66b antibody. In another embodiment, (B-vi) is an anti-CD33 antibody and an anti-CD66b antibody, wherein the anti-CD33 antibody and anti-CD66b are labelled with the same fluorochrome.

In one embodiment, the use according to the present invention is for identifying, determining the relative frequency of and/or quantifying the number of cells within one or more T cell sub-populations.

In one embodiment, the use according to the present invention is for identifying, determining the relative frequency of and/or quantifying the number of cells within one or more lymphoid cell subtypes selected from the group consisting of B cells, T cells and natural killer T cells (NKT); optionally also one or more T cell sub-populations selected from the group consisting of regulatory T cells (Treg), CD4+ T cells and CD8+ T cells; further optionally one or more differentiation states (e.g. naïve or memory) of the one or more T cell sub-populations.

In another aspect, the present invention provides a method for identifying, determining the relative frequency of and/or quantifying the number of cells within hematopoietic cell subtypes in an isolated sample, said method comprising the steps of:
(a) contacting the sample with (i) an anti-CD3 antibody, (ii) an anti-CD56 antibody, (iii) an anti-CD14 antibody, (iv) an anti-CD38 antibody, (v) an anti-CD45 antibody, (vi) an anti-CD90 antibody, (vii) an anti-CD135 antibody, (viii) an anti-CD10 antibody, (ix) an anti-CD11c antibody, (x) an anti-CD19 antibody, (xi) an anti-CD34 antibody, (xii) an anti-CD45RA antibody, (xiii) an anti-CD7 antibody, (xiv) an anti-CD71 antibody, (xv) an anti-CD41/CD61 complex antibody or an anti-CD41 antibody and/or an anti-CD61 antibody (xvi) an anti-CD33 antibody and/or an anti-CD66b antibody, wherein each of (i) to (xvi) is labelled with a different fluorochrome,
wherein when (xvi) is an anti-CD33 antibody and an anti-CD66b antibody, the anti-CD33 antibody and anti-CD66b are labelled with the same fluorochrome, and
wherein when (xv) is an anti-CD41 antibody and an anti-CD61 antibody, the anti-CD41 antibody and the anti-CD61 antibody are labelled with the same fluorochrome;
(b) detecting fluorochrome labelled hematopoietic cells.

In one embodiment, (xv) is an anti-CD41/CD61 complex antibody. In another embodiment, (xv) is an anti-CD41 antibody. In another embodiment, (xv) is an anti-CD61 antibody. In another embodiment, (xv) is an anti-CD41 antibody and an anti-CD61 antibody wherein the anti-CD41 antibody and the anti-CD61 antibody are labelled with the same fluorochrome.

In one embodiment, (xvi) is an anti-CD33 antibody. In another embodiment, (xvi) is an anti-CD66b antibody. In another embodiment, (xvi) is an anti-CD33 antibody and an anti-CD66b antibody wherein the anti-CD33 antibody and anti-CD66b are labelled with the same fluorochrome In a preferred embodiment, there is provided a method for identifying, determining the relative frequency of and/or quantifying the number of cells within hematopoietic cell subtypes in an isolated sample, said method comprising the steps of:
(a) contacting the sample with (i) an anti-CD3 antibody, (ii) an anti-CD56 antibody, (iii) an anti-CD14 antibody, (iv) an anti-CD38 antibody, (v) an anti-CD45 antibody, (vi) an anti-CD90 antibody, (vii) an anti-CD135 antibody, (viii) an anti-CD10 antibody, (ix) an anti-CD11c antibody, (x) an anti-CD19 antibody, (xi) an anti-CD34 antibody, (xii) an anti-CD45RA antibody, (xiii) an anti-CD7 antibody, (xiv) an anti-CD71 antibody, (xv) an anti-CD41/CD61 complex antibody (xvi) an anti-CD33 antibody and an anti-CD66b antibody, wherein each of (i) to (xvi) is labelled with a different fluorochrome,
wherein the anti-CD33 antibody and the anti-CD66b antibody are labelled with the same fluorochrome;
(b) detecting fluorochrome labelled hematopoietic cells.

The step of detecting the fluorochrome labelled hematopoietic cells may be performed by flow cytometry.

The method of the invention may be adapted for further characterising lymphoid cell subtypes in the sample. In one embodiment, the method may comprise the further steps of:
(c) providing another part of the sample, which part has not been used in step (a) and/or (b);
(d) contacting the sample of step (c) with (B-i) an anti-CD3 antibody, (B-ii) an anti-CD56 antibody, (B-iii) an anti-CD45 antibody, (B-iv) an anti-CD19 antibody, (B-v) an anti-CD45RA antibody, (B-vi) an anti-CD33 antibody and/or an anti-CD66b antibody, (B-vii) an anti-CD4 antibody, (B-viii) an anti-CD8 antibody, (B-ix) an anti-CD95 antibody, (B-x) an anti-TCRγδ antibody, (B-xi) an anti-CD127 antibody, (B-xii) an anti-CD62L antibody, (B-xiii) an anti-CD25 antibody, wherein each of (B-i) to (B-xiii) is labelled with a different fluorochrome,
wherein when (B-vi) is an anti-CD33 antibody and an anti-CD66b antibody, the anti-CD33 antibody and anti-CD66b are labelled with the same fluorochrome;
(e) detecting fluorochrome labelled lymphoid cells.

In another aspect, the present invention provides a method for identifying, determining the relative frequency of and/or quantifying the number of cells within lymphoid cell subtypes in an isolated sample, said method comprising the steps of:
(a) contacting the sample with (B-i) an anti-CD3 antibody, (B-ii) an anti-CD56 antibody, (B-iii) an anti-CD45 antibody, (B-iv) an anti-CD19 antibody, (B-v) an anti-CD45RA antibody, (B-vi) an anti-CD33 antibody and/or an anti-CD66b antibody, (B-vii) an anti-CD4 antibody, (B-viii) an anti-CD8 antibody, (B-ix) an anti-CD95 antibody, (B-x) an anti-TCRγδ antibody, (B-xi) an anti-CD127 antibody, (B-xii) an anti-CD62L antibody, (B-xiii) an anti-CD25 antibody, wherein each of (B-i) to (B-xiii) is labelled with a different fluorochrome,
wherein when (B-vi) is an anti-CD33 antibody and an anti-CD66b antibody, the anti-CD33 antibody and anti-CD66b are labelled with the same fluorochrome;
(b) detecting fluorochrome labelled lymphoid cells.

In one embodiment, (B-vi) is an anti-CD33 antibody. In another embodiment, (B-vi) is an anti-CD66b antibody. In another embodiment, (B-vi) is an anti-CD33 antibody and an anti-CD66b antibody, wherein the anti-CD33 antibody and anti-CD66b are labelled with the same fluorochrome.

The step of detecting the fluorochrome labelled lymphoid cells may be performed by flow cytometry.

The method of the present invention may further comprise the step of contacting the sample with a fluorescent cell viability marker; preferably the fluorescent cell viability marker is selected from propidium iodide (PI), propidium monoazide, ethidium monoazide, calcein AM, 7-aminoactinomycin (7-AAD), 4',6-diamidino-2-phenylindole (DAPI), and derivatives thereof; more preferably the fluorescent cell viability marker is PI.

The method of the present invention may further comprise a step wherein the sample is contacted with a known number of microspheres before the contacting of step (a) and/or (d). Preferably, the microspheres are fluorescently labelled.

The method of the present invention may further comprise use of a gating strategy which comprises the steps of:
(a) Exclude cell aggregates and dead cells;
(b) Identify CD45+ cells (leukocytes);
(c) Discriminate the myeloid cell population and the lymphoid cell population;
(d) Identify the major subpopulations of the myeloid cells (monocytes, iPMN, PMN, dendritic cells, myeloblasts and myeloid progenitors) and lymphoid cells (T-cells, NKt cells, mature B-cells, Pro-B, Pre-B and NK cells);
(e) Pool the myeloid committed progenitors and LIN–CD34+ cells; and
(f) Identify the Hematopoietic Stem and Progenitors Cell (HSPC) subsets.

Alternatively, the method of the present invention may further comprise use of a gating strategy which comprises the steps of:
(a) Exclude cell aggregates and dead cells;
(b) Identify CD34+ cells (progenitor cells);
(c) Identify CD45+ cells (leukocytes);
(d) From the CD34+CD45+ cell population, identify the HSPC subsets and LIN+CD34+ subsets.

The method of the present invention may further comprise the steps of:
(a) lysing red blood cells in the sample; and
(b) isolating non-lysed cells in the sample from the lysed red blood cells.

The method of the present invention may be used to identify, determine the relative frequency of and/or quantify the number of cells within one or more hematopoietic cell subtypes selected from the group consisting of immature polymorphonuclear leukocytes (iPMN), polymorphonuclear leukocytes (PMN), monocytes, dendritic cells (DC)/DC progenitors, myeloblasts, T-cells, natural killer T cells (NKT), natural killer cells (NK), B-cells, pre-B cells, pro-B cells, pro-lymphocytes, pro-erythroblasts, erythroblasts, hematopoietic stem cells (HSC), multipotent progenitor cells (MPP), multipotent lymphoid progenitor cells (MLP), early T progenitors (ETP), pre-B/natural killer cells (PRE-B/NK), common myeloid progenitor cells (CM P), granulocyte/macrophage progenitors (GM P), and megakaryocyte/erythrocyte progenitors (MEP).

The method of the present invention may be used to identify, determine the relative frequency of and/or quantify the number of cells within one or more T cell sub-populations.

The method of the present invention may be used to identify, determine the relative frequency of and/or quantify the number of cells within one or more lymphoid cell subtypes selected from the group consisting of B cells, T cells and natural killer T cells (NKT); optionally also one or more T cell sub-populations selected from the group consisting of regulatory T cells (Treg), CD4+ T cells and CD8+ T cells; further optionally one or more differentiation states (e.g. naïve or memory) of the one or more T cell sub-populations.

The sample may be a whole blood sample, and/or the sample may be obtained from peripheral blood, bone marrow, cord blood (CB), mobilized PB (mPB), human-in-mouse xenotrasplantations, or in vitro human cells suspensions.

The sample volume may be 10-5000 μl; preferably 50-1000 μl, more preferably 100-500 μl. The volume may be about 10 μl, about 20 μl; about 30 μl; about 40 μl; about 50 μl; about 60 μl; about 70 μl; about 80 μl; about 90 μl; about 100 μl; about 150 μl; about 200 μl; about 250 μl; about 300 μl; about 350 μl; about 400 μl; about 450 μl; about 500 μl; about 750 μl; about 1000 μl; about 2000 μl; about 3000 μl; about 4000 μl; or about 5000 μl.

Where the sample is obtained from BM, a smaller sample volume may be used. For example the BM sample volume may be 50-200 μl. Alternatively, where the sample is obtained from PB, a larger sample volume may be used. For example, the PB sample volume may be 200-500 μl.

In some embodiments, greater than 95% of the hematopoietic cell subtypes in the sample are identified, preferably greater than 99% of the hematopoietic cell subtypes in the sample are identified, more preferably greater than 99.5% of the hematopoietic cells subtypes in the sample are identified.

In another aspect, the present invention provides a kit for identifying, determining the relative frequency of and/or quantifying the number of cells within hematopoietic cell subtypes comprising (i) an anti-CD3 antibody, (ii) an anti-CD56 antibody, (iii) an anti-CD14 antibody, (iv) an anti-CD38 antibody, (v) an anti-CD45 antibody, (vi) an anti-CD90 antibody, (vii) an anti-CD135 antibody, (viii) an anti-CD10 antibody, (ix) an anti-CD11c antibody, (x) an anti-CD19 antibody, (xi) an anti-CD34 antibody, (xii) an anti-CD45RA antibody, (xiii) an anti-CD7 antibody, (xiv) an anti-CD71 antibody, (xv) an anti-CD41/CD61 complex antibody or an anti-CD41 antibody and/or an anti-CD61 antibody (xvi) an anti-CD33 antibody and/or an anti-CD66b antibody, wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome;

optionally wherein the kit further comprises a red blood cell lysis buffer.

In another aspect, the present invention provides a composition for identifying, determining the relative frequency of and/or quantifying the number of cells within hematopoietic cell subtypes comprising (i) an anti-CD3 antibody, (ii) an anti-CD56 antibody, (iii) an anti-CD14 antibody, (iv) an anti-CD38 antibody, (v) an anti-CD45 antibody, (vi) an anti-CD90 antibody, (vii) an anti-CD135 antibody, (viii) an anti-CD10 antibody, (ix) an anti-CD11c antibody, (x) an anti-CD19 antibody, (xi) an anti-CD34 antibody, (xii) an anti-CD45RA antibody, (xiii) an anti-CD7 antibody, (xiv) an anti-CD71 antibody, (xv) an anti CD41/CD61 complex antibody or an anti-CD41 antibody and/or an anti-CD61 antibody (xvi) an anti-CD33 antibody and/or an anti-CD66b antibody, wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome.

In one embodiment of the kit of the present invention, the kit further comprises (B-i) an anti-CD3 antibody, (B-ii) an anti-CD56 antibody, (B-iii) an anti-CD45 antibody, (B-iv) an anti-CD19 antibody, (B-v) an anti-CD45RA antibody, (B-vi) an anti-CD33 antibody and/or an anti-CD66b antibody, (B-vii) an anti-CD4 antibody, (B-viii) an anti-CD8 antibody, (B-ix) an anti-CD95 antibody, (B-x) an anti-TCRγδ antibody, (B-xi) an anti-CD127 antibody, (B-xii) an anti-CD62L antibody, (B-xiii) an anti-CD25 antibody, wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome.

In one embodiment of the kit and/or the composition of the present invention, (xv) is an anti-CD41/CD61 complex antibody.

In one embodiment of the kit and/or the composition of the present invention, (xvi) is an anti-CD33 antibody and an anti-CD66b antibody wherein both antibodies are labelled with the same fluorochrome, In a preferred embodiment of the kit and/or the composition of the present invention, (xv) is an anti-CD41/CD61 complex antibody and (xvi) is an anti-CD33 antibody and an anti-CD66b antibody wherein the anti-CD33 antibody and the anti-CD66b antibody are labelled with the same fluorochrome.

In another aspect, the present invention provides a kit for identifying, determining the relative frequency of and/or quantifying the number of cells within lymphoid cell subtypes comprising (B-i) an anti-CD3 antibody, (B-ii) an anti-CD56 antibody, (B-iii) an anti-CD45 antibody, (B-iv) an anti-CD19 antibody, (B-v) an anti-CD45RA antibody, (B-vi) an anti-CD33 antibody and/or an anti-CD66b antibody, (B-vii) an anti-CD4 antibody, (B-viii) an anti-CD8 antibody, (B-ix) an anti-CD95 antibody, (B-x) an anti-TCRγδ antibody, (B-xi) an anti-CD127 antibody, (B-xii) an anti-CD62L antibody, (B-xiii) an anti-CD25 antibody, wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome;

optionally wherein the kit further comprises a red blood cell lysis buffer.

In another aspect, the present invention provides a composition for identifying, determining the relative frequency of and/or quantifying the number of cells within lymphoid cell subtypes comprising (B-i) an anti-CD3 antibody, (B-ii) an anti-CD56 antibody, (B-iii) an anti-CD45 antibody, (B-iv) an anti-CD19 antibody, (B-v) an anti-CD45RA antibody, (B-vi) an anti-CD33 antibody and/or an anti-CD66b antibody, (B-vii) an anti-CD4 antibody, (B-viii) an anti-CD8 antibody, (B-ix) an anti-CD95 antibody, (B-x) an anti-TCRγδ antibody, (B-xi) an anti-CD127 antibody, (B-xii) an anti-CD62L antibody, (B-xiii) an anti-CD25 antibody, wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome.

In one embodiment, (B-vi) is an anti-CD33 antibody and an anti-CD66b antibody, wherein the anti-CD33 antibody and anti-CD66b are labelled with the same fluorochrome.

In a preferred embodiment, the kit and/or the composition of the present invention further comprises microspheres, preferably fluorescently-labelled microspheres, for providing an internal counting standard.

The kit and/or the composition of the present invention may further comprise a fluorescent cell viability marker; preferably the fluorescent cell viability marker is selected from propidium iodide (PI), propidium monoazide, ethidium monoazide, calcein AM, 7-aminoactinomycin (7-AAD), 4',6-diamidino-2-phenylindoleand derivatives thereof; more preferably the fluorescent cell viability marker is PI.

In another aspect, the present invention provides an anti-CD90 antibody (i) for use in diagnosing a blood disorder, wherein the anti-CD90 antibody (i) is used in combination with an anti-CD3 antibody (ii), an anti-CD56 antibody (iii), an anti-CD14 antibody (iv), an anti-CD38 antibody (v), an anti-CD45 antibody (vi), an anti-CD135 antibody (vii), an anti-CD10 antibody (viii), an anti-CD11c antibody (ix), an anti-CD19 antibody (x), an anti-CD34 antibody (xi), an anti-CD45RA antibody (xii), an anti-CD7 antibody (xiii), an anti-CD71 antibody (xiv), an anti CD41/CD61 complex antibody or an anti-CD61 antibody and/or an anti-CD41 antibody (xv), an anti-CD33 antibody and/or an anti-CD66b antibody (xvi) wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome.

The fluorochromes may be selected from the group consisting of small molecule fluorochromes, protein fluorochromes, organic polymer fluorochromes, and multicomponent combinations thereof. Preferably, the fluorochromes may be selected from the group consisting of allophycocyanin (APC), allophycocyanin cyanine 7 (APC-Cy7), allophycocyanin R700 (APC-R700), phycoerythrin (PE), phycoerythrin cyanine 5 (PE-Cy5), phycoerythrin cyanine 7 (PE-Cy7), peridinin chlorophyll protein cyanine 5.5 (PerCP-Cy5.5), Brilliant Blue 515 (BB515), Brilliant Violet 421 (BV421), Brilliant Violet 510 (BV510), Brilliant Violet 605 (BV605), Brilliant Violet 650 (BV650), Brilliant Violet 711 (BV711), Brilliant Violet 785 (BV785), Brilliant Ultraviolet 395 (BUV395), and Brilliant Ultraviolet 737 (BUV 737).

In any of the aspects or embodiments of the present invention, the anti-CD90 antibody may be labelled with a protein fluorochrome, the anti-CD3 antibody may be labelled with an organic polymer fluorochrome, the anti-CD56 antibody may be labelled with a multicomponent fluorochrome comprising a protein fluorochrome and a small molecule fluorochrome, the anti-CD14 antibody may be labelled with an organic polymer fluorochrome, the anti-CD38 antibody may be labelled with an organic polymer fluorochrome, the anti-CD45 antibody may be labelled with an organic polymer fluorochrome, the anti-CD135 antibody may be labelled with a protein fluorochrome, the anti-CD10 antibody may be labelled with an organic polymer fluorochrome, the anti-CD11c antibody may be labelled with an organic polymer fluorochrome, the anti-CD19 antibody may be labelled with a multicomponent fluorochrome comprising a protein fluorochrome and a small molecule fluorochrome, the anti-CD34 antibody may be labelled with an organic polymer fluorochrome, the anti-CD45RA antibody may be labelled with a multicomponent fluorochrome comprising a protein fluorochrome and a small molecule fluorochrome, the anti-CD7 antibody may be labelled with a multicomponent fluorochrome comprising a protein fluorochrome and a small molecule fluorochrome, the anti-CD71 antibody may be labelled with an organic polymer fluorochrome, the anti-CD41/CD61 complex antibody may be labelled with a multicomponent fluorochrome comprising a protein fluorochrome and a small molecule fluorochrome the anti-CD61 antibody may be labelled with a multicomponent fluorochrome comprising a protein fluorochrome and a small molecule fluorochrome, the anti-CD41 antibody may be labelled with a multicomponent fluorochrome comprising a protein fluorochrome and a small molecule fluorochrome, the anti-CD33 antibody may be labelled with an organic polymer fluorochrome, and/or the anti-CD66b antibody may be labelled with an organic polymer fluorochrome.

Preferably, the anti-CD90 antibody is labelled with APC, the anti-CD3 antibody is labelled with BV605, the anti-CD56 antibody is labelled with PE-Cy5, the anti-CD14 antibody is labelled with BV510, the anti-CD38 antibody is labelled with BUV737, the anti-CD45 antibody BUV395, the anti-CD135 antibody is labelled with PE, the anti-CD10 antibody is labelled with BV785, the anti-CD11c antibody is labelled with BV650, the anti-CD19 antibody is labelled with APC-R700, the anti-CD34 antibody is labelled with BV421, the anti-CD45RA antibody is labelled with APC-Cy7, the anti-CD7 antibody is labelled with PerCP-Cy5.5, the anti-CD71 antibody is labelled with BV711, the anti-CD41/CD61 complex antibody is labelled with PE-Cy7, the anti-CD41 antibody is labelled with PE-Cy7, the anti-CD61 antibody is labelled with PE-Cy7, the anti-CD33 antibody is labelled with BB515, and/or the anti-CD66b antibody is labelled with BB515.

In another embodiment, the anti-CD3 antibody is labelled with BV605, the anti-CD56 antibody is labelled with PE-Cy5, the anti-CD45 antibody is labelled with BUV395, the anti-CD19 antibody is labelled with APC-R700, the anti-CD45RA antibody is labelled with APC-Cy7, the anti-CD33 antibody is labelled with BB515, the anti-CD66b antibody is labelled with BB515, the anti-CD4 antibody is labelled with BV711, the anti-CD8 antibody is labelled with BUV737, the anti-CD95 antibody is labelled with PE, the anti-TCRγδ antibody is labelled with BV421, the anti-CD127 antibody is labelled with APC, the anti-CD62L antibody is labelled with BV510 and/or the anti-CD25 antibody is labelled with BV786.

Figure 1A:
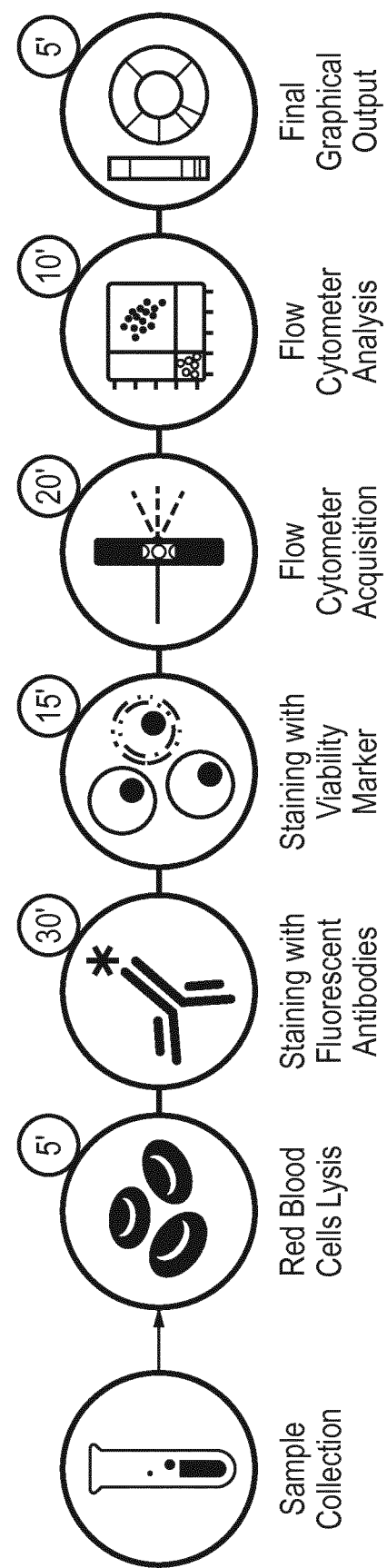
FIG. 1
Figure 1B:
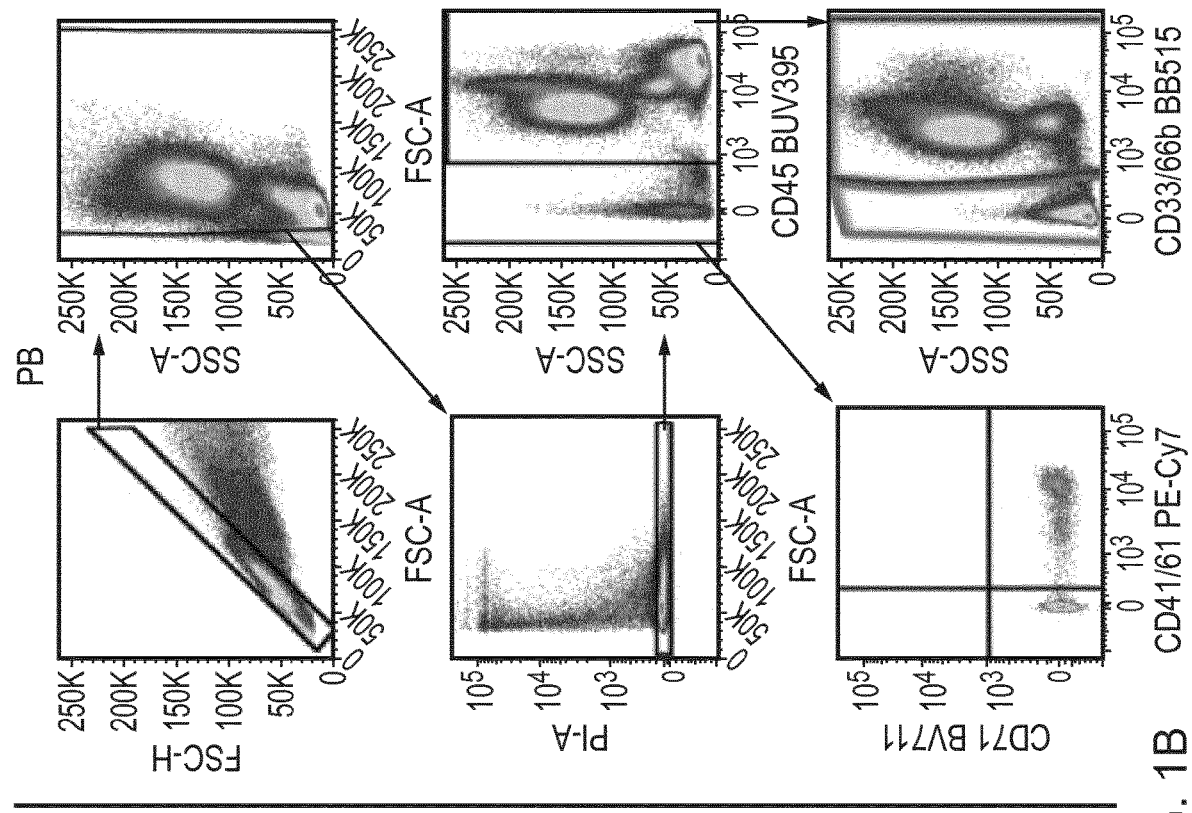
Figure 1B:
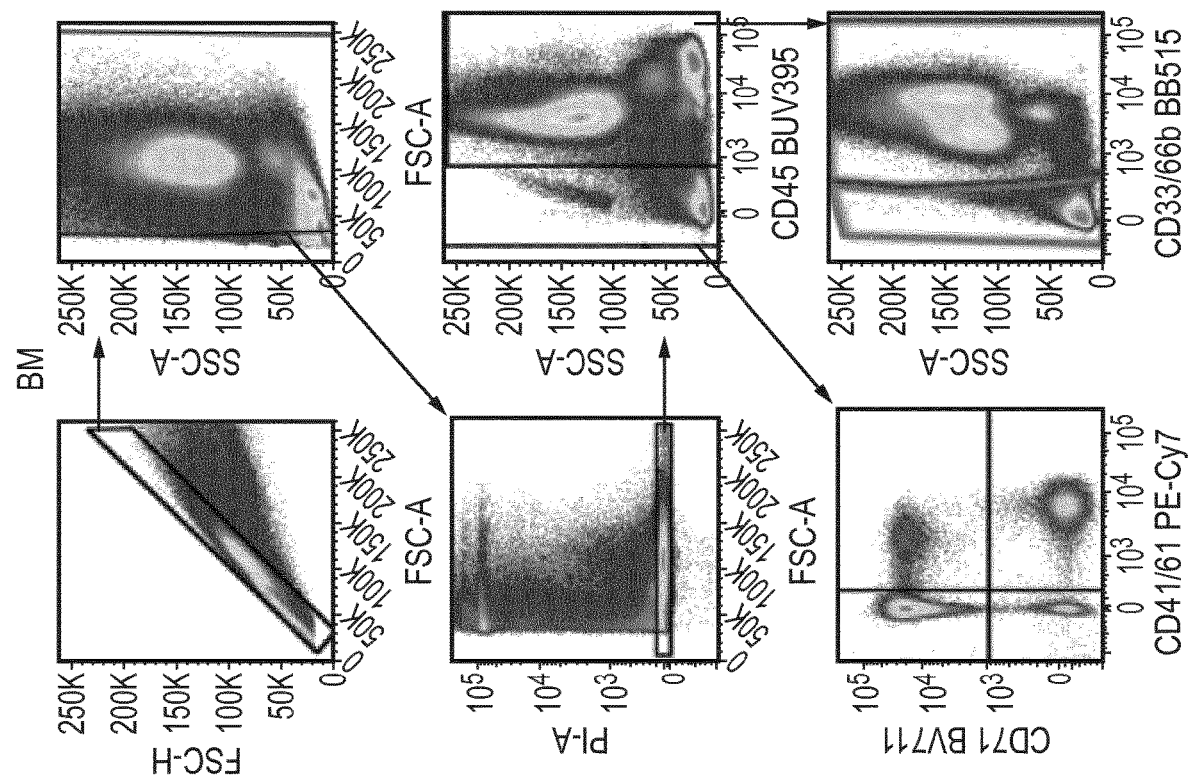
Figure 1C:
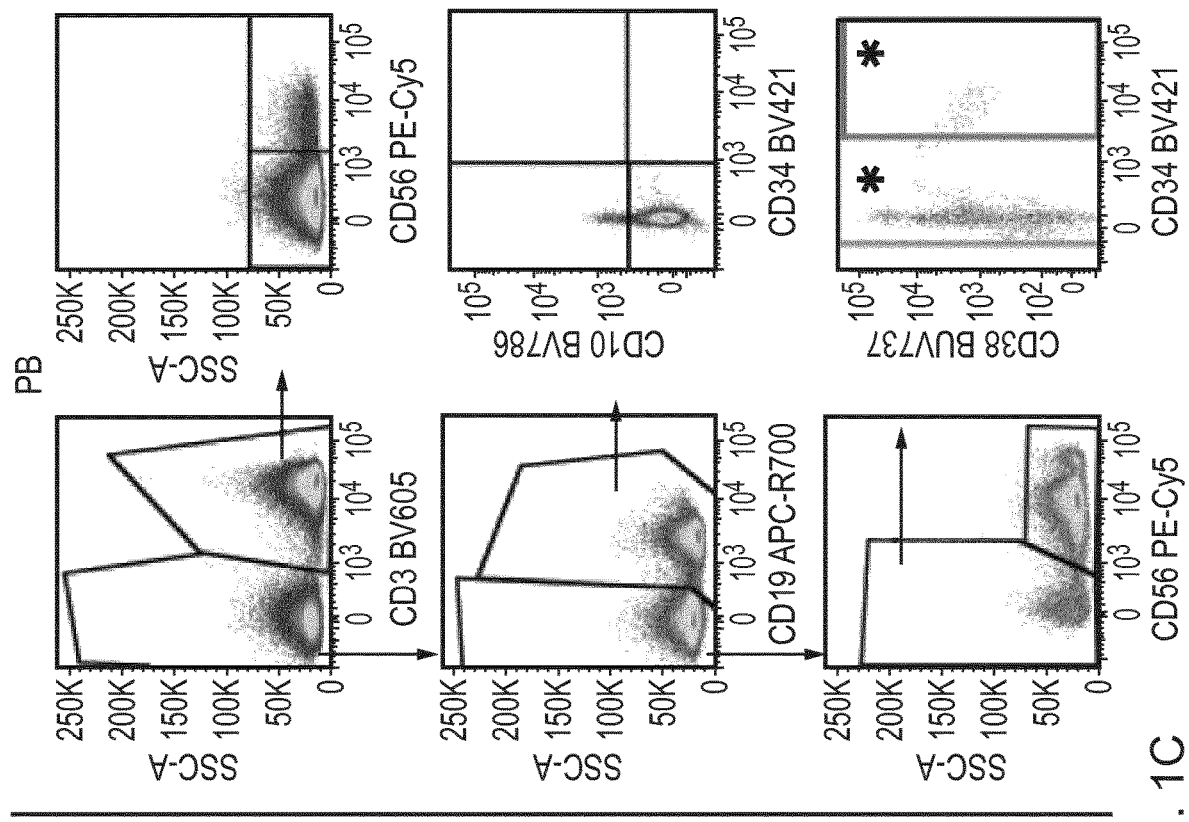
Figure 1C:
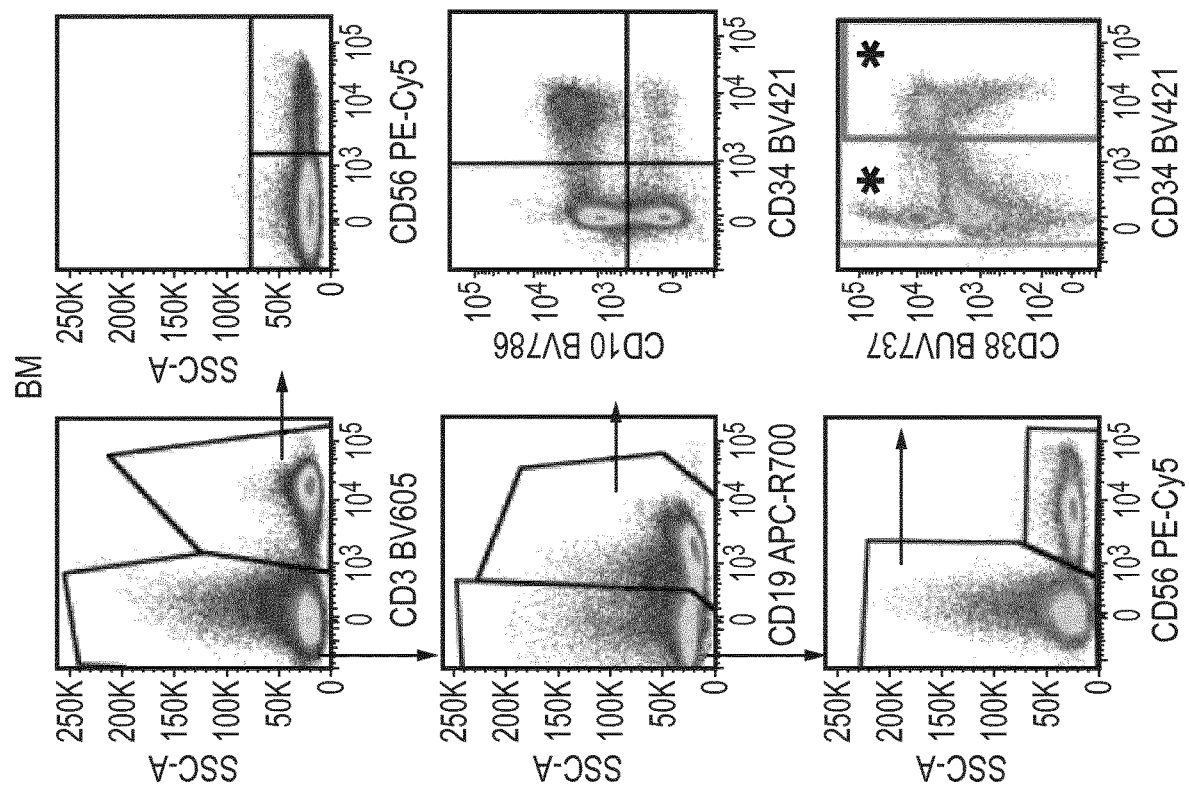
Figure 1D:
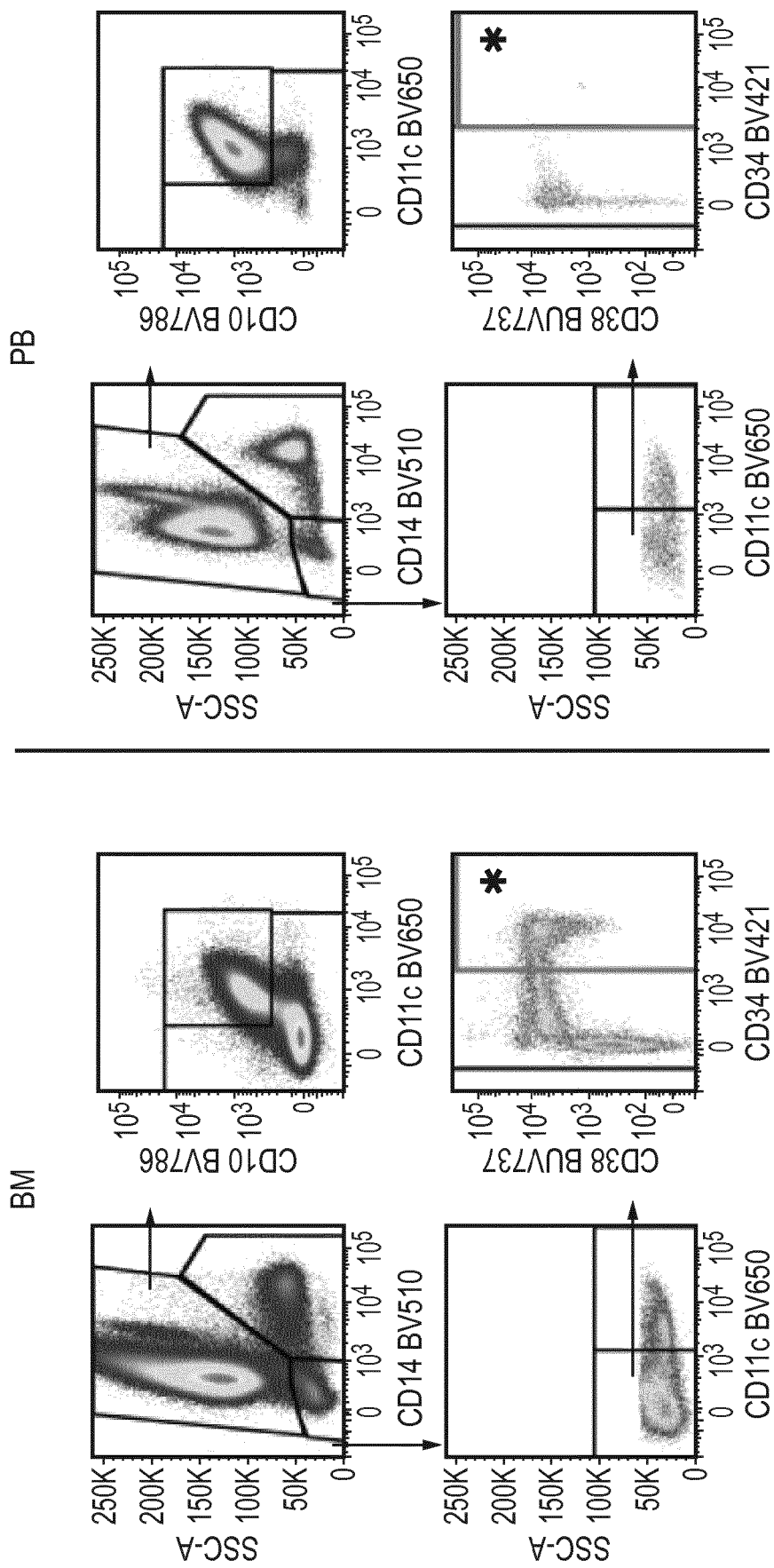
Figure 1E:
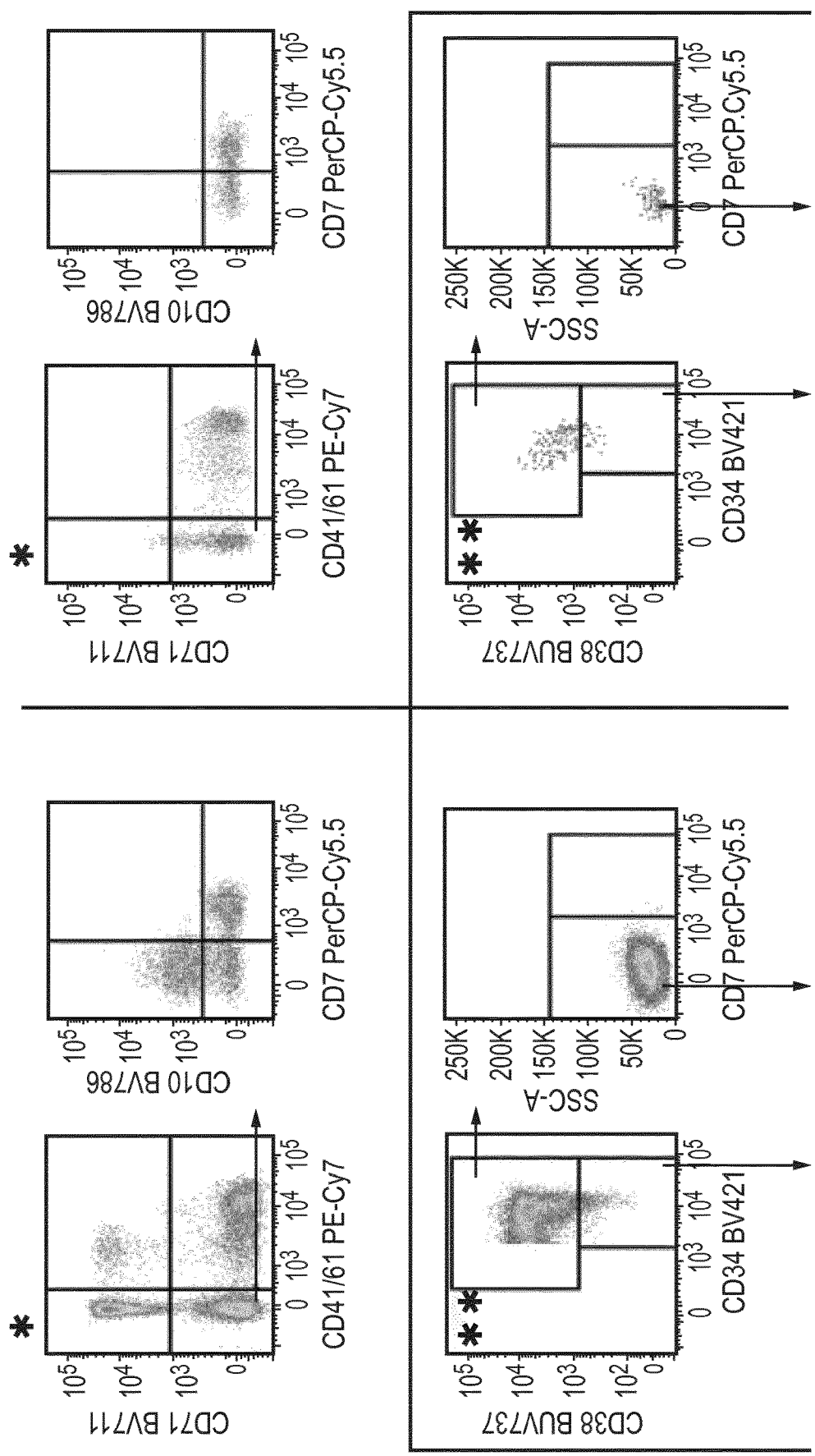
Figure 1E:
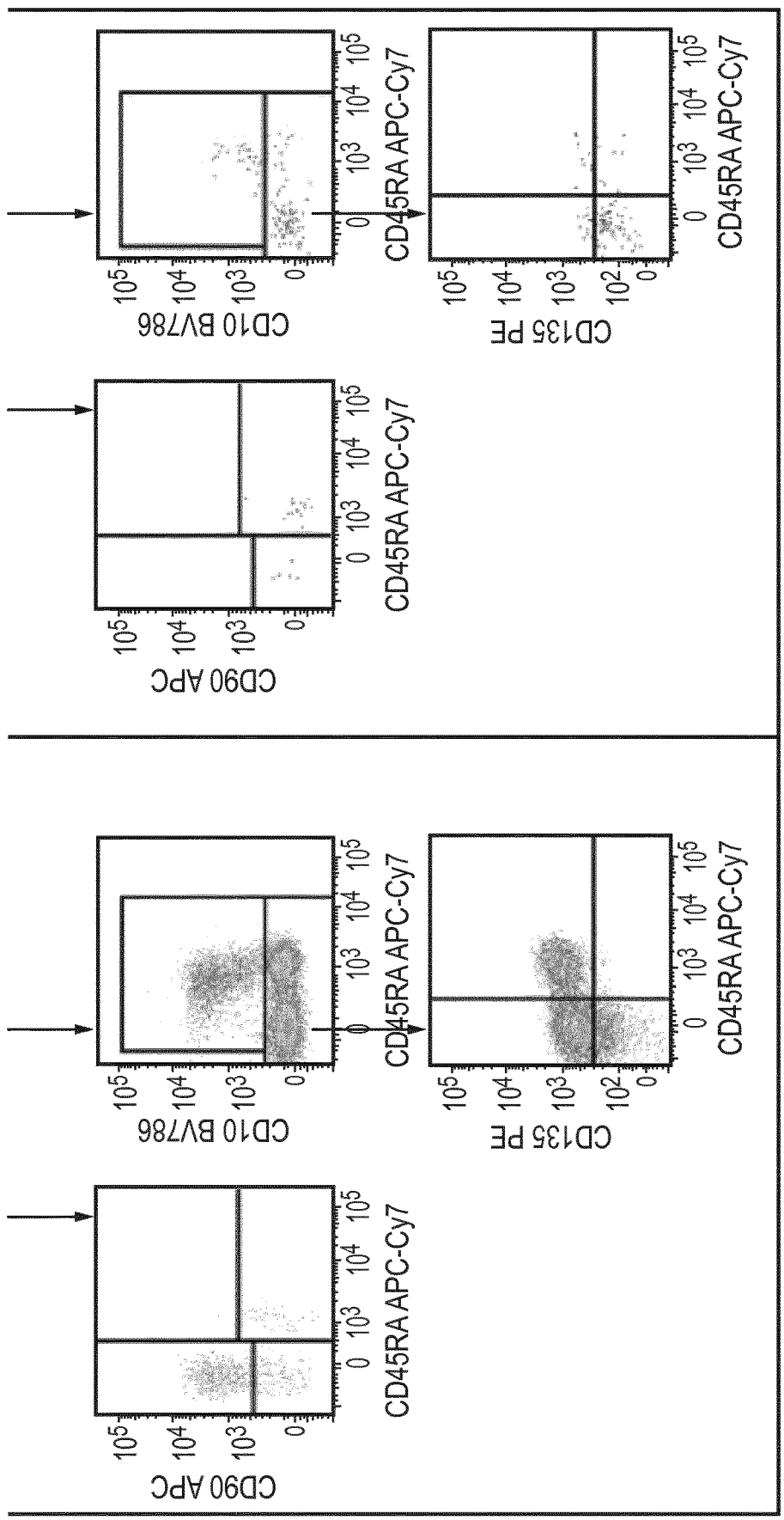

Protocol workflow and gating strategy. (A) Whole Blood Dissection (WBD) protocol workflow. After BM or PB sampling, the red blood cells are lysed and the samples are stained with the fluorescent antibodies against the WBD markers. The following steps comprise: incubation with Propidium Iodide (PI) to discriminate live and dead cells, acquisition to LSR-Fortessa (BD Bioscience), data analyses and graphical sample composition representation. The numbers in the smaller circles indicate the minutes required for performing each step: once setup, the final WBD results are available in less than 1.5 hours from the arrival of the samples. (B-E) Gating strategy for characterization of healthy donor (HD) bone marrow (BM, left side of the colored frames) and peripheral blood (PB, right side of the colored frames). (B), black frame: after physical parameters, live/dead and pan-leukocyte CD45 marker expression discrimination, the gating strategy identifies myeloid (blue gate) and not-myeloid cells (green gate). (D), blue frame: Myeloid cell subtypes and myeloid-committed CD34+ cells (red gate and asterisk). (C), green frame: gating strategy for not-myeloid cells identifies lymphoid and Lineage negative (LIN−, orange gate) cells. Lin− cells are separated on the basis of CD34 expression as LIN−CD34− (orange asterisk) and LIN−CD34+ (red gate and asterisk) cells. (E), orange frame: LIN−CD34− subtypes (orange asterisk); red frame: HSPC subpopulations analyzed from the merge of myeloid-committed CD34+ (from panel D) and LIN−CD34+ (from panel C) cells (double red asterisks).

FIG. 2

Morphological validation. Table showing the sorting strategies and the resulting morphology of myeloid (B), lymphoid (C) and immature (D) cell subtypes isolated from bone marrow of healthy donors. Cells were sorted according to the markers listed in Table A and on the basis of the gating strategy described in "FIG. 1B-E". For each compartment, the dot plots show the physical parameters (left plot) and the markers (right plot) used to identify and sort the different sub-populations. The pictures on the right show the observed morphology of the isolated cells (May-Grunwald-Giemsa staining; magnification reported on the bottom right corner of each picture).

FIG. 3

Analyses of BM samples from healthy donors and patients: (A) Example graphical representation for the composition of the CD45+ cell population. Ticks allow the estimation of the relative contribution of the different hematopoietic subtypes. The ring charts show frequencies of hematopoietic cell subtypes as a percentage of the total CD45+ cells. Left panel: representation of immature subtypes. The "less-exploded" section shows immature cells (LIN−CD34− and Pro-B cells) while the "more-exploded" section shows the frequencies of LIN−CD34+ (HSPC) sub-populations out of the total CD45+ cell population. The stacked bar graph on the left of the ring chart is an expanded representation of the frequency of different HSPC subtypes within the LIN−CD34+ compartment. The percentage reported on each graph displays the relative frequency of the LIN−CD34+ cells out of total CD45+ cells. Right panel: representation of the mature subpopulations. The non-exploded section of the ring chart (grey) displays the myeloid and lymphoid subpopulations of the LIN+CD34− cells. (B-D) Averages of BM hematopoietic cell subtype frequencies in pediatric (B left panel, n=5) and adult (B right panel, n=5) healthy donors (HD) in comparison with WAS (C left panel, n=6), ADA-SCID (C right panel, n=4), CGD (n=1) patients and MLD (D, n=7) affected individuals. (Ad=adult; Ped=pediatric; WAS=Wskott-Aldrich Syndrome; ADA-SCID=adenosine deaminase severe combined immunodeficiency; CGD=Chronic Granulomatous Disease; MLD=Metachromatic Leukodystrophy).

FIG. 4

Analyses of BM samples from patients with myeloid or lymphoid leukemia. From A to E: Whole Blood Dissection (WBD) graphical representation showing BM composition in 1 representative adult HD (A), 5 patients with acute myeloid leukemia (AML) (B-C), 1 patient with acute lymphoid leukemia (ALL) (D) and 1 patient with multiple myeloma (MM) (E) The percentages indicate the relative frequency of the cells with immature markers likely belonging to leukemic blasts on total CD45+ cells. In the MM sample, we highlighted in black the fraction of CD38high putative plasmablasts in the unknown compartment.

FIG. 5

CD34 vs. CD33/66b markers allows type and differentiation state categorization of leukemic samples. Dot plots showing on the left, the expression of the CD45 marker (gated on live cells) and on the right, the combined expression of CD34 vs. CD33/CD66b surface molecules (gated on CD45+ cells) in, from top to bottom, 1 representative adult HD (A), 6 patients with acute myeloid leukemia (AML) (B-C), 1 patient with acute lymphoid leukemia (ALL) (D) and 1 patient with Multiple Myeloma (MM) (E). For the MM patient we showed also the expression of CD38 vs. CD34 markers on the unknown events to evaluate the presence of CD38high plasmablast-like cells.

FIG. 6

Fluorescent minus one (FMO) controls for Whole Blood Dissection (WBD) staining. Hematopoietic cell subpopulations were distinguished using physical parameters (forward scatter and side scatter), a cell viability marker (PI) and fluorochrome-labelling—see Example 1.

FIG. 7

Relative frequency of hematopoietic cell subtypes in bone marrow and peripheral blood of healthy donors. Comparison of bone marrow (BM, n=9) and peripheral blood (PB, n=8) whole blood samples obtained from healthy donors. Starting from top left to bottom right, bar graphs show distribution of CD45+ (A), myeloid (B), lymphoid (C), CD19+ (D), LIN− (E), and HSPC (F) subpopulations in BM (left stacked bar graph) and PB (right stacked bar graph). The order of the stacked bars corresponds to the key on the right of each bar graph.

FIG. 8

Comparison of bone marrow hematopoietic cell subtypes in healthy donors and patients. Stacked bar graphs showing bone marrow (BM) hematopoietic cell subtypes in adult (n=5) and pediatric (n=5) healthy donors and in WAS (n=6), ADA-SCID (n=7), MLD (n=6) and CGD (n=1) patients. (A-B) detailed and general composition of CD45+ compartment; (C) Frequencies of cells within the myeloid compartment; (D) Frequencies of cells within the lymphoid compartment, (E) Frequencies of cells within the CD19+ compartment; (F) Frequencies of cells within the LIN− compartment; (G) Frequencies of cells within the LIN−CD34+ compartment. The order of the stacked bars corresponds to the key on the right of each bar graph.

FIG. 9

Alternative Whole Blood Dissection (WBD) gating strategy: (A-D) Gating strategy for characterization of healthy donor (HD) bone marrow (BM, left side of the colored frames) and peripheral blood (PB, right side of the colored frames) CD34+ compartment. (A) Black frame: after physical parameters, live/dead and progenitor-enriching CD34 marker expression discrimination, the gating strategy identifies CD45+ and CD45− subpopulations. Among CD45+ cells we distinguish myeloid (blue gate) and not-myeloid cells (green gate). (B), blue frame: CD34+ myeloid cell subtypes and LIN−CD33+ progenitors (red gate and asterisk). (C), green frame: gating strategy for not-myeloid cells identifies lymphoid and Lineage negative (LIN−, orange gate) cells. (D), orange/red frame: HSPC subpopulations analyzed from the merge of myeloid-committed CD34+ (from panel B) and LIN−CD34+ (from panel C) cells (double red asterisks).

FIG. 10

Comparison of bone marrow CD34+ hematopoietic subsets in healthy donors and patients: stacked bar graphs showing bone marrow (BM) CD34+ hematopoietic subpopulations in adult (n=5) and pediatric (n=5) healthy donors and in WAS (n=6), ADA (n=7), MLD (n=6) and CGD (n=1) patients. (A) Detailed and general composition of CD34+ compartment; (B) Frequencies of HSPC subpopulations and LIN+ compartment within the CD34+ cells; (C) Frequencies of LIN+CD34+ subpopulations within the LIN+CD34+ compartment.

FIG. 11

Absolute count quantification of hematopoietic subsets through Whole Blood Dissection (WBD). (A) Linear regression of 3 independent experiments of whole PB dilutions into PBS. Different amount (500 ul, 200 ul, 100 ul) of PB from the same aliquot were collected. PBS was added in order to reach final volume of 500 ul in all the samples. Same quantity of count beads was used in all the samples in order to calculate the amount of cells and calculate linear regression. $R^2$ of each replicate and the mean of the three replicates are reported on the right. (B) Quantification of BM and PB hematopoietic subsets in 3 representative WAS, ADA-SCID and MLD patients. BM and PB samples were collected from the same patient in the same day. Ticks allow the estimation of the absolute count/ul of whole blood of the different hematopoietic subtypes.

FIG. 12

Whole Blood Dissection (WBD) allows characterization of human cells in xeno-transplantations. (A) Experimental scheme for human-in-mouse transplantations. Sub-lethally irradiated NSG (n=3) and SGM3 (n=3) mice were transplanted with 300.000 cord-blood (CB) derived CD34+ cells/mouse. Bleedings were performed at 6 and 13 weeks. At 16 weeks mice were euthanized and peripheral blood (PB), bone marrow (BM) and spleen (SPL) were collected and analyzed. (B) Survival curve of treated mice. (C) Dot plots displaying specificity of human anti-CD45 antibody in total live cells. On the left, one NSG and one SGM3 representative mice transplanted with human CB CD34+ cells, on the right, PB analyses of one NSG and one SGM3 un-transplanted mice. (D) Graph on right shows percentage of human cells in PB overtime and in BM and SPL at sacrifice in NSG and SGM3 transplanted mice. Graph on the left shows the absolute count of human cells detected in PB of NSG and SGM3 transplanted mice. Absolute count expressed as number of cells/ul of whole PB. (E-F) Composition of human graft in PB overtime and BM and SPL at sacrifice in NSG (E) and 3SGM3 (F) mice. Ticks allow the estimation of the absolute count/ul of whole blood (PB) or in the entire organ (BM and SPL) of the different hematopoietic subtypes.

FIG. 13

Detection of human hematopoietic cells in peripheral blood of transplanted mice: stacked bar graphs showing the human hematopoietic cell composition in peripheral blood (PB) of NSG (n=3) and 3SGM (n=3) mice a different time points after xeno-transplantation of human cord-blood derived HSPC. (A-B) Detailed and general composition of human cells within CD45+ compartment. (C) Frequencies of human myeloid cells within the myeloid compartment. (D) Frequencies of human lymphoid cells within the lymphoid compartment. (E) Frequencies of human LIN− cells within the LIN− compartment. (F) Frequencies of human HSPC subtypes within the LIN−CD34+ compartment.

FIG. 14

Detection of human hematopoietic cells in bone marrow and spleen of transplanted mice at sacrifice: stacked bar graphs showing the human hematopoietic cell composition in bone marrow (BM) and spleen (SPL) of NSG (n=2) and 3SGM (n=1) mice at sacrifice after xeno-transplantation of human cord-blood derived HSPC. (A-B) Detailed and general composition of human cells within CD45+ compartment. (C) Frequencies of human myeloid cells within the myeloid compartment. (D) Frequencies of human lymphoid cells within the lymphoid compartment. (E) Frequencies of human LIN− cells within the LIN− compartment. (F) Frequencies of human HSPC subtypes within the LIN−CD34+ compartment.

FIG. 15

Absolute quantification of human hematopoietic cells in peripheral blood of transplanted mice: graphs showing the absolute count overtime of human hematopoietic cells in peripheral blood (PB) of NSG (n=3) and 3SGM (n=3) mice after xeno-transplantation of human cord-blood derived HSPC. (A) Measurement overtime of human lymphoid (green), myeloid (blue) and LIN− (orange) subpopulations in peripheral blood transplanted mice; (B-C) Absolute cell count overtime of human myeloid (B) and lymphoid (C) subsets in peripheral blood of transplanted mice.

FIG. 16

Additional panel for lymphoid subset dissection. A. Table of markers and fluorochromes used for identifying T cell subpopulations. CD3+ (B), T cell (C), CD4+ T cell (D), CD8+ Tcell (E) subsets in Ad and Ped HD.

DETAILED DESCRIPTION

The practice of the present invention will employ, unless otherwise indicated, conventional techniques of cell biology, molecular biology, histology, immunology, oncology, which are within the capabilities of a person of ordinary skill in the art. Such techniques are explained in the literature.

Hematopoetic Cells

Hematopoietic cells, also known as blood cells, hemocytes, or hematocytes, are the cellular components of blood. Cells in the hematopoietic lineage are derived from multipotent hematopoietic stem cells (HSCs), which are capable of self-renewal and differentiation into any blood cell lineage and provide for life-long production of all lineages of haematopoietic cells.

Haematopoietic progenitor cells also have the capacity to differentiate into more specialised cell types. However, in contrast to HSC, they are already far more specific, i.e. they are already pushed to differentiate into their "target" cell. A difference between stem cells and progenitor cells is that stem cells can replicate indefinitely, whereas progenitor cells can only divide a limited number of times.

As used herein the term "differentiated cell" is understood as a cell which has become more specialised than a HSC. Cell differentiation may occur during the development of a multicellular organism as the organism changes from a single zygote to a complex system of tissues and cell types.

Differentiation is also a common process in adults: adult stem cells divide and create fully-differentiated daughter cells during tissue repair and normal cell turnover. Differentiation dramatically changes a cell's size, shape, membrane potential, metabolic activity and responsiveness to signals. These changes are largely due to highly-controlled modifications in gene expression. In other words, a differentiated cell is a cell that has specific structures and performs certain functions due to a developmental process which involves the activation and deactivation of specific genes.

Thus, as used herein the term "hematopoietic cell" encompasses the most primitive (least differentiated) HSCs and all cells derived from HSCs irrespective of differentiation status. Accordingly, the haematopoietic lineage includes immature polymorphonuclear leukocytes (iPMN), polymorphonuclear leukocytes (PMN), monocytes, dendritic cells (DC)/DC progenitors, myeloblasts, T-cells, natural killer T cells (NKT), natural killer cells (NK), B-cells, pre-B cells, pro-B cells, pro-lymphocytes, pro-erythroblasts, erythroblasts, hematopoietic stem cells (HSC), multipotent progenitors (MPP), multipotent lymphoid progenitors (MLP), early T progenitors (ETP) cells, pre-B/natural killer cells (PRE-B/NK), common myeloid progenitors (CMP), granuclocyte/macrophage progenitors (GMP), and megakaryocyte/erythrocyte progenitors (MEP).

Differentiated hematopoietic cells belong to either the myeloid lineage or the lymphoid lineage. The myeloid lineage includes thrombocytes, erythrocytes, granulocytes, and monocytes (e.g. macrophages and myeloid dendritic cells). The lymphoid lineage includes B-cells, T-cells, natural killer cells and lymphoid dendritic cells.

Myeloid cells and lymphoid cells may be distinguished by the respective presence or absence of a myeloid cell marker, such as CD33 or CD66b. Myeloid and lymphoid cells may be distinguished on the basis of a combination of CD33 and CD66b expression.

Accordingly, hematopoietic cells encompass over twenty distinct cell subtypes, each of which has different characteristics and functions. The hematopoietic cell subtypes may, for example, be distinguished from each other by examination of cell morphology under the microscope. However, this is time consuming and requires a specially trained cell biologist. Moreover, some of the morphological differences between closely related cells are difficult to discern by eye.

In an alternative approach, hematopoietic cell subtypes may be identified and classified on the basis of their differential expression of cell surface markers, such as receptor proteins or ligands that are exposed on the cell membrane. Such cell markers may be referred to using cluster of differentiation (CD) nomenclature. For example, CD4 is a protein expressed on the surface of T helper cells, whereas CD8 is a protein expressed on the surface of cytotoxic T cells. CD molecules may be common to more than one type of cell, e.g. CD45, which is expressed by all leukocytes (i.e. they are CD45+) but not by erythrocytes (i.e. they are CD45−). Accordingly, in order to definitively distinguish each hematopoietic cell subtype in a sample from one another it is necessary to examine the expression status of several CD molecules. This allows the so-called immunophenotype of the cell to be determined.

According to the present invention, haematopoietic cell subtypes may be identified using antibodies specific for the following CD markers: CD3, CD56, CD14, CD38, CD45, CD90, CD135, CD10, CD11c, CD19, CD34, CD45RA, CD7, CD71, CD61, CD41, CD41/CD61 complex; CD33, or CD66b.

The hematopoietic cell subtypes identified in the present invention may have the immunophenotypes as set out in Table 1.

TABLE 1

Immunophentoypes of hematopoietic cell subtypes.

| Cell type | Immunophenotype |
| --- | --- |
| iPMN | CD45+ CD33+ CD66b+ SSChigh CD10− and/or CD11c |
| PMN | CD45+ CD33+ CD66b+ SSChigh CD10+ CD11c+ |
| Monocyte | CD45+ CD33+ CD14+ |
| DC/DC progenitor | CD45+ CD33+ CD14− CD11c+ |
| Myeloblast | CD45+ CD33+ CD14− CD11c+ CD34− |
| T-cell | CD45+ CD33− CD66b− CD3+ CD56− |
| NKT | CD45+ CD33− CD66b− CD3+ CD56+ |
| NK | CD45+ CD33− CD66b− CD3+ CD19− CD56+ |
| B-cell | CD45+ CD33− CD66b− CD3+ CD19+ CD10− CD43− |
| Pre-B cell | CD45+ CD33− CD66− CD3− CD19+ CD10+ CD34− |
| Pro-B cell | CD45+ CD33− CD66b− CD3− CD19+ CD10+ CD34+ |
| Pro-lymphocyte | CD45+ CD33− CD66b− CD3− CD19− CD56− CD34− CD71− CD41/61− CD7+ or CD10+ |
| Pro-erythroblast | CD45+ CD33− CD66b− CD3− CD19− CD56− CD34− CD71+ |
| Erythroblast | CD45− CD71+ |
| HSC | CD45+ CD14− CD11c− CD3− CD19− CD56− CD34+ CD38− CD90+ CD45RA− |
| MPP | CD45+ CD14− CD11c− CD3− CD19− CD56− CD34+ CD38− CD90− CD45RA− |
| MLP | CD45+ CD14− CD11c− CD3− CD19− CD56− CD34+ CD38− CD90− CD45RA+ |

TABLE 1-continued

Immunophentoypes of hematopoietic cell subtypes.

| Cell type | Immunophenotype |
|---|---|
| ETP | CD45+ CD14− CD11c− CD3− CD19− CD56− CD34+ CD38+ CD7+ |
| PRE-B/NK | CD45+ CD14− CD11c− CD3− CD19− CD56− CD34+ CD38+ CD7− CD10+ CD45RA+ |
| CMP | CD45+ CD14− CD11c− CD3− CD19− CD56− CD34+ CD38+ CD7− CD10− CD135+ CD45RA− |
| GMP | CD45+ CD14− CD11c− CD3− CD19− CD56− CD34+ CD38+ CD7− CD10− CD135+ CD45RA+ |
| MEP | CD45+ CD14− CD11c− CD3− CD19− CD56− CD34+ CD38+ CD7− CD10− CD135− CD45RA− |

Antibodies

As used herein, the term "antibody" is understood as a polypeptide substantially encoded by an immunoglobulin gene or immunoglobulin genes, or fragments thereof, which specifically bind and recognize an antigen (e.g. a cell surface marker). As used herein, the term "antibody" refers to a whole or intact antibody molecule (e.g., IgM, IgG (including IgG1, IgG2, IgG3, and IgG4), IgA, IgD, or IgE) or any antigen-binding fragment thereof.

An antibody may be a polyclonal antibody or a monoclonal antibody. Monoclonal antibodies are produced by identical immune cells (e.g. hybridomas that may be generated from the fusion of an antibody producing B-cell line and a cancerous B-cell line). A monoclonal antibody directed to a particular antigen will recognise a single specific epitope on said antigen. In contrast, polyclonal antibodies are produced from multiple non-identical cell lines and therefore recognise several different epitopes on a particular antigen.

Antigen-binding fragments of an antibody include, e.g., a single chain antibody, a single chain Fv fragment (scFv), an Fd fragment, an Fab fragment, an Fab' fragment, or an F(ab')$_2$ fragment. An scFv fragment is a single polypeptide chain that includes both the heavy and light chain variable regions of the antibody from which the scFv is derived. In addition, intrabodies, minibodies, triabodies, and diabodies (see, e.g., Todorovska et al. (2001) J Immunol Methods 248(1):47-66; Hudson and Kortt (1999) J Immunol Methods 231(1):177-189; Poljak 25 (1994) Structure 2(12): 1121-1123; Rondon and Marasco (1997) Annual Review of Microbiology 21:257-283, are also included in the definition of antibody and are compatible for use in the methods described herein. The term "antibody," as used herein, also includes antibody fragments either produced by the modification of whole antibodies or those synthesized de novo using recombinant methods.

Suitable methods for producing an antibody or antigen binding fragments thereof directed to a particular antigen are known in the art (see, e.g., Greenfield (2014) Antibodies: A Laboratory Manual, Second Edition 201-221).

An anti-CD41/CD61 complex antibody is an antibody immunospecific for the CD41/CD61 complex. CD41/CD61, also known as gpIIb/IIIa, is a member of a family integrin receptors. This is a complex comprised by CD41 and CD61 through non-covalent association.

Fluorochromes

As used herein, the term "fluorochrome" refers to a fluorescent molecule that can re-emit light following excitation with absorbed light that has a specific wavelength. Typically, the light emitted by a fluorochrome has longer wavelength than that of the absorbed light. The term "fluorochrome" may be used interchangeably with the terms "fluorophore", "fluorescent label", "fluorescent dye", "fluorescent tag", "fluorescent marker", "fluorescent probe" and "fluorescent reporter".

A fluorochrome may be characterised by a number of properties. Such properties include maximum excitation and emission wavelengths, which correspond to the respective peaks of the fluorochrome emission and excitation spectra. The difference between the maximum excitation and emission wavelengths is known as the Stokes shift.

Other parameters that may be used to characterise fluorochromes include extinction coefficient, which is a measure of the concentration dependence of the amount of light absorbed at a given wavelength; quantum yield, which is a measure of the efficiency of energy transfer from absorbed light to emitted light; and fluorescent lifetime—i.e. the duration of the excited state before the fluorochrome re-emits light and returns to the ground state.

The present invention relates to the use of antibodies labelled with different fluorochromes. Different fluorochromes may be distinguished in terms of their characteristic properties. For example, the different fluorochromes may have different maximum excitation wavelengths, different emission wavelengths, different Stokes shifts, different extinction coefficients, different quantum yields, and/or different fluorescent lifetimes.

Fluorochromes may consist of a single fluorescent molecule, which is responsible for both the absorption and emission of light. Alternatively, fluorochromes may be a multi-component system, e.g., a tandem fluorochrome comprising a donor molecule, responsible for the absorption of light, and an acceptor molecule, responsible for emission of light. Energy is transferred from the excited donor molecule to the acceptor molecule by fluorescence resonance energy transfer.

Fluorochromes may be broadly grouped into four classes: small molecules, proteins (or peptides), organic polymers, and quantum dots.

Small Molecule Fluorochromes

A wide array of small molecule fluorochromes are known in the art—see, e.g. Lavis and Raines (2008) ACS Chem Biol 20; 3(3):142-155. Small molecule fluorophores typically have a molecular weight of 200-2000 Da.

A small molecule fluorochrome may be selected from aromatic amino acids (e.g. phenylalanine, tyrosine and tryptophan); polycyclic aromatics (e.g. derivatives of naphthalene, pyrene and anthracene); coumarins; quinolones; indoles (e.g. DAPI); imidizoles (e.g. Hoechst dyes); benzoxadiazole derivatives (e.g. NBD); fluoresceins; rhodamines; naphthoxanthenes; phenanthridines, boron difluoride dipyrromethene (BODIPY) derivatives; cyanines; phthalocyanines; oxazines; and triarylmethanes.

Cyanine fluorochromes are characterised by a polymethine chain between two nitrogen atoms (i.e. $R_2N-(CH=CH)_n-CH=N+R_2$), where typically n=2, 3, 5 or 7. Accordingly, in some embodiments, at least one fluorochrome is a cyanine, or a derivative thereof. In some embodiments, the cyanine has 2, 3, 5, or 7, methinegroups in its polymethine chain.

In some embodiments, at least one fluorochrome is a tiarylmethane, preferably ethyl-[4-[[4-[ethyl-[(3-sulfophenyl)methyl]amino]phenyl]-(2-sulfophenyl) methylidene]-1-cyclohexa-2,5-dienylidene]-[(3-sulfophenyl)methyl]azanium (also known as Brilliant Blue).

Protein Fluorochromes

Protein (or peptide) fluorochromes are well known in the art, and may have molecular weights of about 20-300 kDa. Protein fluorochromes comprise at least one fluorescent group known as a chromophore, which is responsible for the absorption and emission of light. This chromophore may be provided by modified amino acid residues as in green fluorescent protein (GFP) that was first isolated from the jellyfish Aequora victoria.

Derivatives of GFP include enhanced GFP (EGFP); yellow fluorescent protein (YFP), and derivatives thereof (e.g. citrine, venus, and YPet); blue fluorescent protein (BFP), and derivatives thereof (e.g. enhanced EBFP, and Azurite), cyan fluorescent protein (CFP), and derivatives thereof (e.g. enhanced CFP, Cerulean, and CyPet, and mTurquoise2); mOrange; and mCherry.

An alternative class of protein fluorochromes are the phycobilliproteins produced by photosynthetic cyanobacteria and algae. Unlike GFP derivatives, the chromophore of a phycobilliprotein is provided by a co-factor known as bilin, which has linear arrangement of four pyrrole rings.

Accordingly, in some embodiments, at least one fluorochrome is a phycobilliprotein, or a derivative thereof. The fluorochrome may be phycoerythrin (PE); a phycocyanin (CPC); an allophycocyanin (APC); or a multicomponent system comprising PE, CPC, APC, or derivatives thereof; or derivatives thereof.

Another class of protein fluorochromes that may be used in the present invention are the peridinin chlorophyl proteins (PerCP), which are produced by photosynthetic dinoflagellates (see, e.g. Hofman et al (1996) Science vol. 272, pp. 1788-1791). Thus, in some embodiments, at least one fluorochrome is a PerCP; a multicomponent system comprising a PerCP or a derivative thereof; or a derivative thereof.

Organic Polymer Fluorochromes

Organic polymer fluorochromes consist of repeating fluorescent subunits that act cooperatively. For example, some polymer fluorochromes comprise unsaturated organic moieties with alternating single and double bonds and aromatic units. This conjugated structure creates a continuous 7-orbital system and extended electronic delocalization over the length of the polymer fluorochrome giving rise to, for example, a large extinction coefficients (>106 $M^{-1}$ $cm^{-1}$) and a high fluorescence intensity. See, e.g., Chattopadhyay et al (2012) Cytometry Part A 81A:456-466 and Handbook of Conducting Polymers, $3^{rd}$ ed, Conjugated Polymers, Chapters 14, 17 and 22. Examples of commercially available organic polymer fluorochromes that may be used in the present invention are the Brilliant Violet™ (BV) series developed by BioLegend and the Brilliant Ultraviolet™ (BUV) developed by BD Biosciences.

Thus, in some embodiments, at least one fluorochrome is an organic polymer fluorochrome, a multicomponent system comprising an organic polymer fluorochrome, or derivatives thereof.

Quantum Dot Fluorochromes

Quantum dots (QDs) are particles or nanocrystals of semiconducting material with diameters in the range of 2-10 nm which are able to re-emit absorbed light. The energy required to excite a QD is dependent on its diameter. Accordingly, the emission wavelength (i.e. fluorescent colour) of a QD may be tuned by varying its diameter. Other advantageous properties of QDs include high photostability and large extinction coefficient (see, e.g. Resch-Genger (2008) Nature Methods 5, 763-775). QD dots may be manufactured by any method known in the art.

Thus, in some embodiments, at least one fluorochrome is a QD fluorochrome, a multicomponent system comprising a QD fluorochrome, or a derivative thereof.

Examples of fluorochromes that could be used in the present invention are fluorochromes having the following spectral properties:

| Excitation wavelength (nm) | Maximal emission wavelength range (nm) |
|---|---|
| 355 | 365-430 |
| 355 | 720-760 |
| 405 | 410-460 |
| 405 | 480-560 |
| 405 | 590-620 |
| 405 | 630-670 |
| 405 | 685-735 |
| 405 | 750-810 |
| 488 | 495-550 |
| 488 | 670-720 |
| 561 [488]* | 560-610 |
| 561 [488]* | 650-690 |
| 561 [488]* | 750-810 |
| 635 | 650-670 |
| 635 | 690-720 |
| 635 | 750-810 |

*Alternative excitation wavelength

The fluorochromes may be selected from, for example, the group consisting of allophycocyanin (APC), allophycocyanin cyanine 7 (APC-Cy7), allophycocyanin R700 (APC-R700), phycoerythrin (PE), phycoerythrin cyanine 5 (PE-Cy5), phycoerythrin cyanine 7 (PE-Cy7), peridinin chlorophyll protein cyanine 5.5 (PerCP-Cy5.5), Brilliant Blue 515 (BB515), Brilliant Violet 421 (BV421), Brilliant Violet 510 (BV510), Brilliant Violet 605 (BV605), Brilliant Violet 650 (BV650), Brilliant Violet 711 (BV711), Brilliant Violet 785 (BV785), Brilliant Ultraviolet 395 (BUV395), and Brilliant Ultraviolet 737 (BUV 737).

The fluorochromes may have the spectral properties set out in below.

| Fluorochrome | Excitation wavelength (nm) | Maximal emission wavelength range (nm) |
|---|---|---|
| BUV395 | 355 | 365-430 |
| BUV737 | 355 | 720-760 |
| BV421 | 405 | 410-460 |
| BV510 | 405 | 480-560 |
| BV605 | 405 | 590-620 |
| BV650 | 405 | 630-670 |
| BV711 | 405 | 685-735 |
| BV786 | 405 | 750-810 |
| BB515 | 488 | 495-550 |
| PerCP-Cy5.5 | 488 | 670-720 |
| PE | 561 [488]* | 560-610 |
| PE-Cy5 | 561 [488]* | 650-690 |
| PE-Cy7 | 561 [488]* | 750-810 |
| APC | 635 | 650-670 |
| APC-R700 | 635 | 690-720 |
| APC-Cy7 | 635 | 750-810 |

*Alternative excitation wavelength

Fluorochrome Labelled Antibodies

The present invention relates to the use of antibodies labelled with fluorochromes. As used herein the term "labelled" is understood to mean that the antibody is associated, conjugated, tagged, linked, or attached, to the fluorochrome. The antibody may be covalently or non-covalently labelled. By way of example, the antibody may be labelled via a reactive amine group, e.g. an exposed lysine side chain amine group or an α-amine group.

A person skilled in the art is able to routinely prepare antibodies labelled with fluorochromes without undue experimentation. Antibodies labelled with fluorochromes may be prepared according to any method known in the art. For example, commercially available antibodies labelled with a fluorochrome may be employed for the present invention.

In any of the aspects or embodiments of the present invention, the anti-CD90 antibody may be labelled with a protein fluorochrome, the anti-CD3 antibody may be labelled with an organic polymer fluorochrome, the anti-CD56 antibody may be labelled with a multicomponent fluorochrome comprising a protein fluorochrome and a small molecule fluorochrome, the anti-CD14 antibody may be labelled with an organic polymer fluorochrome, the anti-CD38 antibody may be labelled with an organic polymer fluorochrome, the anti-CD45 antibody may be labelled with an organic polymer fluorochrome, the anti-CD135 antibody may be labelled with a protein fluorochrome, the anti-CD10 antibody may be labelled with an organic polymer fluorochrome, the anti-CD11c antibody may be labelled with an organic polymer fluorochrome, the anti-CD19 antibody may be labelled with a multicomponent fluorochrome comprising a protein fluorochrome and a small molecule fluorochrome, the anti-CD34 antibody may be labelled with an organic polymer fluorochrome, the anti-CD45RA antibody may be labelled with a multicomponent fluorochrome comprising a protein fluorochrome and a small molecule fluorochrome, the anti-CD7 antibody may be labelled with a multicomponent fluorochrome comprising a protein fluorochrome and a small molecule fluorochrome, the anti-CD71 antibody may be labelled with an organic polymer fluorochrome, the anti-CD41/CD61 complex antibody may be labelled with a multicomponent fluorochrome comprising a protein fluorochrome and a small molecule fluorochrome the anti-CD61 antibody may be labelled with a multicomponent fluorochrome comprising a protein fluorochrome and a small molecule fluorochrome, the anti-CD41 antibody may be labelled with a multicomponent fluorochrome comprising a protein fluorochrome and a small molecule fluorochrome, the anti-CD33 antibody may be labelled with an organic polymer fluorochrome, and/or the anti-CD66b antibody may be labelled with an organic polymer fluorochrome.

In any aspects or embodiments of the present invention, the anti-CD90 antibody may be labelled with a fluorochrome having an excitation wavelength of about 635 nm and a maximal emission wavelength range of about 650-670 nm;

the anti-CD3 antibody may be labelled with a fluorochrome having an excitation wavelength of about 405 nm and a maximal emission wavelength range of about 590-620 nm;

the anti-CD56 antibody may be labelled with a fluorochrome having an excitation wavelength of about 561 nm or about 488 nm and a maximal emission wavelength range of about 650-690 nm;

the anti-CD14 antibody may be labelled with a fluorochrome having an excitation wavelength of about 405 nm and a maximal emission wavelength range of about 480-560 nm;

the anti-CD38 antibody may be labelled with a fluorochrome having an excitation wavelength of about 355 nm and a maximal emission wavelength range of about 720-760 nm;

the anti-CD45 antibody may be labelled with a fluorochrome having an excitation wavelength of about 355 nm and a maximal emission wavelength range of about 365-430 nm;

the anti-CD135 antibody may be labelled with a fluorochrome having an excitation wavelength of 561 or 488 nm and a maximal emission wavelength range of about 560-610 nm;

the anti-CD10 antibody may be labelled with a fluorochrome having an excitation wavelength of about 405 nm and a maximal emission wavelength range of about 750-810 nm;

the anti-CD11c antibody may be labelled with a fluorochrome having an excitation wavelength of about 405 nm and a maximal emission wavelength range of about 630-670 nm;

the anti-CD19 antibody may be labelled with a fluorochrome having an excitation wavelength of about 635 nm and a maximal emission wavelength range of about 690-720 nm;

the anti-CD34 antibody may be labelled with a fluorochrome having an excitation wavelength of about 405 nm and a maximal emission wavelength range of about 410-460 nm;

the anti-CD45RA antibody may be labelled with a fluorochrome having an excitation wavelength of about 635 nm and a maximal emission wavelength range of about 750-810 nm;

the anti-CD7 antibody may be labelled with a fluorochrome having an excitation wavelength of about 488 nm and a maximal emission wavelength range of about 670-720 nm;

the anti-CD71 antibody may be labelled with a fluorochrome having an excitation wavelength of about 405 nm and a maximal emission wavelength range of about 685-735 nm;

the anti-CD41 antibody may be labelled with a fluorochrome having an excitation wavelength of about 561 nm or about 488 nm and a maximal emission wavelength range of about 750-810 nm;

the anti-CD61 antibody may be labelled with a fluorochrome having an excitation wavelength of about 561 nm or about 488 nm and a maximal emission wavelength range of about 750-810 nm;

the anti-CD41/CD61 complex antibody may be labelled with a fluorochrome having an excitation wavelength of about 561 nm or about 488 nm and a maximal emission wavelength range of about 750-810 nm;

the anti-CD33 antibody may be labelled with a fluorochrome having an excitation wavelength of about 488 nm and a maximal emission wavelength range of about 495-550 nm; and/or the anti-CD66b antibody may be labelled with a fluorochrome having an excitation wavelength of about 488 nm and a maximal emission wavelength range of about 495-550 nm.

The anti-CD90 antibody may be labelled with a protein fluorochrome having an excitation wavelength of about 635 nm and a maximal emission wavelength range of about 650-670 nm;

the anti-CD3 antibody may be labelled with an organic polymer fluorochrome having an excitation wavelength of about 405 nm and a maximal emission wavelength range of about 590-620 nm;

the anti-CD56 antibody may be labelled with a multicomponent fluorochrome comprising a protein fluorochrome and a small molecule fluorochrome, wherein the multicomponent fluorochrome has an excitation wavelength of about 561 nm or about 488 nm and a maximal emission wavelength range of about 650-690 nm;

the anti-CD14 antibody may be labelled with an organic polymer fluorochrome having an excitation wavelength of about 405 nm and a maximal emission wavelength range of about 480-560 nm;

the anti-CD38 antibody may be labelled with an organic polymer fluorochrome having an excitation wavelength of about 355 nm and a maximal emission wavelength range of about 720-760 nm;

the anti-CD45 antibody may be labelled with an organic polymer fluorochrome having an excitation wavelength of about 355 nm and a maximal emission wavelength range of about 365-430 nm;

the anti-CD135 antibody may be labelled with a protein fluorochrome having an excitation wavelength of 561 or 488 nm and a maximal emission wavelength range of about 560-610 nm;

the anti-CD10 antibody may be labelled with an organic polymer fluorochrome having an excitation wavelength of about 405 nm and a maximal emission wavelength range of about 750-810 nm;

the anti-CD11c antibody may be labelled with an organic polymer fluorochrome having an excitation wavelength of about 405 nm and a maximal emission wavelength range of about 630-670 nm;

the anti-CD19 antibody may be labelled with a multicomponent fluorochrome comprising a protein fluorochrome and a small molecule fluorochrome, wherein the multicomponent fluorochrome has an excitation wavelength of about 635 nm and a maximal emission wavelength range of about 690-720 nm;

the anti-CD34 antibody may be labelled with an organic polymer fluorochrome having an excitation wavelength of about 405 nm and a maximal emission wavelength range of about 410-460 nm;

the anti-CD45RA antibody may be labelled with a multicomponent fluorochrome comprising a protein fluorochrome and a small molecule fluorochrome, wherein the multicomponent fluorochrome has an excitation wavelength of about 635 nm and a maximal emission wavelength range of about 750-810 nm;

the anti-CD7 antibody may be labelled with a multicomponent fluorochrome comprising a protein fluorochrome and a small molecule fluorochrome, wherein the multicomponent fluorochrome has an excitation wavelength of about 488 nm and a maximal emission wavelength range of about 670-720 nm;

the anti-CD71 antibody may be labelled with an organic polymer fluorochrome having an excitation wavelength of about 405 nm and a maximal emission wavelength range of about 685-735 nm;

the anti-CD41 antibody may be labelled with a multicomponent fluorochrome comprising a protein fluorochrome and a small molecule fluorochrome, wherein the multicomponent fluorochrome has an excitation wavelength of about 561 nm or about 488 nm and a maximal emission wavelength range of about 750-810 nm;

the anti-CD61 antibody may be labelled with a multicomponent fluorochrome comprising a protein fluorochrome and a small molecule fluorochrome, wherein the multicomponent fluorochrome has an excitation wavelength of about 561 nm or about 488 nm and a maximal emission wavelength range of about 750-810 nm;

the anti-CD41/CD61 complex antibody may be labelled with a multicomponent fluorochrome comprising a protein fluorochrome and a small molecule fluorochrome, wherein the multicomponent fluorochrome has an excitation wavelength of about 561 nm or about 488 nm and a maximal emission wavelength range of about 750-810 nm;

the anti-CD33 antibody may be labelled with an organic polymer fluorochrome having an excitation wavelength of about 488 nm and a maximal emission wavelength range of about 495-550 nm; and/or and the anti-CD66b antibody may be labelled with an organic polymer fluorochrome having an excitation wavelength of about 488 nm and a maximal emission wavelength range of about 495-550 nm.

Preferably, the anti-CD90 antibody may be labelled with APC, the anti-CD3 antibody may be labelled with BV605, the anti-CD56 antibody may be labelled with PE-Cy5, the anti-CD14 antibody may be labelled with BV510, the anti-CD38 antibody may be labelled with BUV737, the anti-CD45 antibody BUV395, the anti-CD135 antibody may be labelled with PE, the anti-CD10 antibody may be labelled with BV785, the anti-CD11c antibody may be labelled with BV650, the anti-CD19 antibody may be labelled with APC-R700, the anti-CD34 antibody may be labelled with BV421, the anti-CD45RA antibody may be labelled with APC-Cy7, the anti-CD7 antibody may be labelled with PerCP-Cy5.5, the anti-CD71 antibody may be labelled with BV711, the anti-CD41 antibody may be labelled with PE-Cy7, the anti-CD61 antibody may be labelled with PE-Cy7, the anti-CD41/CD61 complex antibody may be labelled with PE-Cy7 the anti-CD33 antibody may be labelled with BB515, and the anti-CD66b antibody may be labelled with BB515.

In another embodiment, the anti-CD3 antibody is labelled with a fluorochrome having an excitation wavelength of about 405 nm and a maximal emission wavelength range of about 590-620 nm;

the anti-CD56 antibody is labelled with a fluorochrome having an excitation wavelength of about 561 nm or about 488 nm and a maximal emission wavelength range of about 650-690 nm;

the anti-CD45 antibody is labelled with a fluorochrome having an excitation wavelength of about 355 nm and a maximal emission wavelength range of about 365-430 nm;

the anti-CD19 antibody is labelled with a fluorochrome having an excitation wavelength of about 635 nm and a maximal emission wavelength range of about 690-720 nm;

the anti-CD45RA antibody is labelled with a fluorochrome having an excitation wavelength of about 635 nm and a maximal emission wavelength range of about 750-810 nm;

the anti-CD33 antibody is labelled with a fluorochrome having an excitation wavelength of about 488 nm and a maximal emission wavelength range of about 495-550 nm;

the anti-CD66b antibody is labelled with a fluorochrome having an excitation wavelength of about 488 nm and a maximal emission wavelength range of about 495-550 nm;

the anti-CD4 antibody is labelled with a fluorochrome having an excitation wavelength of about 405 nm and a maximal emission wavelength range of about 685-735 nm;

the anti-CD8 antibody is labelled with a fluorochrome having an excitation wavelength of about 355 nm and a maximal emission wavelength range of about 720-760 nm;

the anti-CD95 antibody is labelled with a fluorochrome having an excitation wavelength of about 561 nm or about 488 nm and a maximal emission wavelength range of about 560-610 nm;

the anti-TCRγδ antibody is labelled with a fluorochrome having an excitation wavelength of about 405 nm and a maximal emission wavelength range of about 410-460 nm;

the anti-CD127 antibody is labelled with a fluorochrome having an excitation wavelength of about 635 nm and a maximal emission wavelength range of about 650-670 nm;

the anti-CD62L antibody is labelled with a fluorochrome having an excitation wavelength of about 405 nm and a maximal emission wavelength range of about 480-560 nm;

and/or the anti-CD25 antibody is labelled with a fluorochrome having an excitation wavelength of about 405 nm and a maximal emission wavelength range of about 750-810 nm.

Preferably, the anti-CD3 antibody is labelled with BV605, the anti-CD56 antibody is labelled with PE-Cy5, the anti-CD45 antibody is labelled with BUV395, the anti-CD19 antibody is labelled with APC-R700, the anti-CD45RA antibody is labelled with APC-Cy7, the anti-CD33 antibody is labelled with BB515, the anti-CD66b antibody is labelled with BB515, the anti-CD4 antibody is labelled with BV711, the anti-CD8 antibody is labelled with BUV737, the anti-CD95 antibody is labelled with PE, the anti-TCRγδ antibody is labelled with BV421, the anti-CD127 antibody is labelled with APC, the anti-CD62L antibody is labelled with BV510 and/or the anti-CD25 antibody is labelled with BV786.

Fluorescent Cell Viability Marker

Isolated samples of hematopoietic cells contain both live (viable) and dead cells. Dead cells are particularly prevalent in samples that have been activated or thawed and are problematic when attempting to analyse those hematopoietic cell subtypes which are present at low frequency e.g. less than 1% of the population. In particular, where an immunostaining approach is adopted, cell death can result in large errors because of the propensity of antibodies to bind non-specifically to dead cells.

One approach to address the problem of dead cells is to isolate the viable cells from dead cells before analysis the composition of the live cell population, thereby reducing non-specific antibody binding.

In another approach, a fluorescent cell viability marker may be used to discriminate between live and dead hematopoietic cells present in the sample.

Thus, the method of the present invention may further comprise the step of contacting the sample with a fluorescent cell viability marker. The fluorescent cell viability marker may be specific for either dead cells or live cells. In a preferred embodiment, the fluorescent cell viability marker is specific for dead cells.

In one embodiment, the fluorescent cell viability maker is selected from propidium iodide (PI), propidium monoazide, ethidium monoazide, calcein AM, 7-aminoactinomycin (7-AAD), 4',6-diamidino-2-phenylindole (DAPI), and derivatives thereof.

PI is a fluorescent intercalating agent with a maximum excitation wavelength of 535 nm and a maximum emission wavelength of 617 nm. PI is membrane impermeable and is therefore excluded from live cells. Accordingly, since PI is only taken up by dead cells they may be distinguished from the live cell population on the basis of PI fluorescent signal. Thus, in preferred embodiments of the present invention, the fluorescent cell viability marker is propidium iodide (PI).

Detection of Labelled Cells

Fluorochrome labelled hematopoietic cells may be detected by any suitable method known in the art. In some embodiments, the step of detecting the fluorochrome labelled cells is performed by flow cytometry.

In a flow cytometry experiment, high throughput multi-parametric analysis (also known as acquisition) is conducted on a cell-by-cell basis as cells suspended in a liquid stream pass through a beam of light generated by appropriately positioned lasers. The extent to which the cells scatter the light is measured as a so-called physical parameter. In addition, the relative fluorescence of excited fluorochrome labelled cells (or auto-fluorescent cells) passing through the light beam can be measured by appropriately positioned detectors.

Modern flow cytometers fitted with multiple light sources of different wavelength (e.g. red, blue, green and violet) and multiple detectors, allow for the simultaneous measurement up to 17 different fluorescent signals (see, e.g. Perfetto et al. (2004) Nat Rev Immunol 4:648-655). Thus, the step of detecting the fluorochrome labelled cells may be performed by 17-colour flow cytometry.

Absolute Cell Quantification

The uses, methods and kits of the invention may allow quantification of the number of cells within each cell subtype.

Cell quantification may be achieved by contacting the sample with a known number of independently identifiable entities, which may provide a reference against which to quantify the number of cells. For example, microspheres (also referred to herein as "beads" or "count beads"), which may be morphologically different to cells and/or may be labelled (e.g. fluorescently labelled), may be contacted with the sample to enable quantification. The microspheres function to provide an internal counting standard. Suitable microspheres are commercially available, such as Precision Count Beads™ (Biolegend). Typically, count beads are in the form of a calibrated suspension of fluorescent microspheres (e.g. about 7-10 μm) that can be detected across a broad range of wavelengths (e.g UV-635 nm excitation and 385-800 nm emission) and contain a known concentration of microspheres.

Cell quantification may be performed independently from the gating strategy by comparing morphological parameters of the microspheres with those of the cells.

For example, the cell count of the sample analyzed (Cs) may be calculated according to the following formula when the starting amount of blood sample (Vs) and bead solution (Vb); the concentration of beads (Cb); and the number of cell (Es) and beads (Eb) events acquired are known:

$$C_s = \frac{V_b \times E_s}{V_s \times E_b} \times C_b$$

Gating Strategy

The present inventors have devised gating strategies that may be used with the various aspects of the present invention. The main gating strategy described herein allows for the identification of, for example, up to 23 different hematopoietic cell subtypes.

The main gating strategy may be used to analyse all the hematopoietic cell subtypes in a sample. Accordingly, the gating strategy is useful for providing a general picture of hematopoietic status.

The gating strategy may include the following steps:
1) Exclude doublets and dead cells
2) Identify the leukocyte compartment (CD45+).
3) Discriminate the two major mature compartments, lymphoid and myeloid
4) Dissect each compartment into its major subpopulations.
5) Pool myeloid committed progenitors and LIN−CD34+ cells 6) Identify the Hematopoietic Stem and Progenitors Cells (HSPC) subsets The main gating strategy may further comprise additional steps, e.g. steps set out in Example 1.

In certain clinical protocols, progenitor cells are identified exclusively on the basis of the expression of the CD34 marker (e.g. on ex vivo hematopoietic stem/progenitor cells gene therapy). The present inventors have devised an alternative gating strategy, which may be used for more detailed analysis of the progenitor compartment (CD34+ cells). The alternative gating strategy may be used to identify both LIN−CD34+ subsets (HSPC) and LIN+CD34+ (i.e. differentiated cells that still express CD34 marker).

This alternative gating strategy may be based on the following steps:
 (a) Exclude doublets and dead cells;
 (b) Identify CD34+ cells (progenitor cells);
 (c) Identify CD45+ cells (leukocytes);
 (d) From the CD34+CD45+ cells population, identify the HSPC subsets and the LIN+CD34+ subsets.

The alternative gating strategy may further comprise additional steps, e.g. one or more steps described in Example 1.

Cell aggregates, also known as doublets may be distinguished from single cells in a process known as doublet discrimination, which is well known in the art.

Dead cells may be distinguished from live cells using a fluorescent cell viability marker.

The myeloid cell population and the lymphoid cell population may be identified and discriminated on the basis of expression of CD33 and CD66b. For example, myeloid cells may be CD33+ and/or CD66b+ whereas lymphoid cells are CD33− and CD66b−.

As used herein, the term "lineage positive (LIN+) cells" refers to hematopoietic cell subtypes which express at least one marker of lineage maturation e.g. CD3, CD19, or CD14. Accordingly, LIN+ cells may be identified and discriminated on the basis of expression of at least one marker of lineage maturation, e.g. CD3, CD19 or CD14.

On the other hand, the term "lineage negative (LIN−) cells" refers to hematopoietic cell subtypes which do not express any marker of lineage maturation. The lack of lineage marker expression is indicative of the immature status of this population.

Advantageously, the gating strategies described herein allow all major lineage positive mature cells, immature progenitors and HSPC to be analysed.

Alternative gating strategies may also be used in the method of present invention, e.g. for specific purposes. The method of the present invention may further comprises the use of a gating strategy described in Example 1, or a variation thereof.

Red Blood Cells

Red blood cells, also known as erythrocytes, are the most abundant hematopoietic cell subtype. The presence of red blood cells can reduce the relative signal strength of other fluorochrome labelled hematopoietic cell subtypes in the same sample. Accordingly, in order improve accuracy of flow cytometric data collection and analysis the red blood cells may be eliminated from the sample before data acquisition. Thus, in some embodiments, the method of the present invention further comprises steps of: (i) lysing the red blood cells in the sample; and (ii) isolating the non-lysed cells in the sample from the lysed red blood cells.

The step of lysing the red blood cells in the sample may be conducted by any suitable method known in the art, e.g. by contacting the sample with a red blood cell lysis buffer. The red blood cell lysis buffer may comprise ammonium chloride ($NH_4Cl$). After contacting the sample with the red blood cell lysis buffer, the sample may be agitated for efficient lysis, e.g. by vortex.

The step of isolating the non-lysed cells in the sample from the lysed red blood cells may be performed using any suitable method known in the art, e.g. by centrifugation, in which the non-lysed cells form a pellet and the lysed red blood cells can then be discarded in the supernatant.

Sample

The present invention relates to determining the relative frequency of hematopoietic cell subtypes and/or lymphoid cell subtypes. As used herein, relative frequency is understood to mean the relative proportion of a particular hematopoietic and/or lymphoid cell subtype in a sample, e.g. the percentage of the particular hematopoietic and/or lymphoid cell subtype relative to the total hematopoietic and/or lymphoid cell population in a sample.

However, the present invention may also be used for quantifying the number of cells within hematopoietic and/or lymphoid cell subtypes.

The present invention allows hematopoietic and/or lymphoid cell subtypes in an isolated sample to be identified, the relative frequency of hematopoietic and/or lymphoid cell subtypes in an isolated sample to be determined and/or the number of cells within hematopoietic and/or lymphoid cell subtypes to be quantified. The sample may be a whole blood sample.

As used herein the term "whole blood sample" is understood to mean a sample in which substantially all the hematopoietic cell subtypes that were present in the sample at the time of collection are still present when the method of the present invention is performed, i.e. the sample has not been modified to isolate a particular subtype. An anticoagulant may be present in a whole blood sample.

The blood sample may be obtained from peripheral blood (PB). As used herein the term "peripheral blood" refers to blood that was obtained from the circulatory system and was not obtained from blood sequestered in e.g. bone marrow (BM), the lymphatic system (e.g. lymph nodes), the spleen, or the liver.

Alternatively, the blood sample may be obtained from bone marrow (BM), cord blood (CB), mobilized PB (mPB), sampling from human-in-mouse xenotransplantations or from in vitro human cells suspensions.

In one embodiment, the sample is an isolated human sample.

The present invention advantageously allows for a minimal sample volume to be used for identifying, determining the relative frequency of and/or quantifying the number of hematopoietic and/or lymphoid cell subtypes in an isolated sample. The sample volume may be 10-5000 µl; preferably 50-1000 µl, more preferably 100-500 µl. The volume may be about 10 µl, about 20 µl; about 30 µl; about 40 µl; about 50 µl; about 60 µl; about 70 µl; about 80 µl; about 90 µl; about 100 µl; about 150 µl; about 200 µl; about 250 µl; about 300 µl; about 350 µl; about 400 µl; about 450 µl; about 500 µl; about 750 µl; about 1000 µl; about 2000 µl; about 3000 µl; about 4000 µl; or about 5000 µl.

Where the sample is obtained from BM, a smaller sample volume may be used. For example the BM sample volume may be 50-200 µl. Alternatively, where the sample is obtained from PB, a larger sample volume may be used. For example, the PB sample volume may be 200-500 µl.

Previous methods for identifying hematopoietic and/or lymphoid cells often require that a sample is split into a number of sub-samples which are then contacted with different combinations of antibodies before conducting separate data collection of each sub-sample. This is disadvantageous since it is both time consuming for a trained operator and requires a larger volume of starting sample.

In contrast, the present invention allows detection of, for example, up to 23 different hematopoietic cell subtypes for a single data acquisition using a sample that has been prepared in a single tube. This represents a significant reduction in starting material and the time of a trained operator.

Accordingly, the step of contacting the cells with the antibodies of the invention may be carried out in a single container.

When characterisation of the identities of, relative frequencies of and/or quantification of the number of cells within both hematopoietic and lymphoid cell subtypes are carried out, a sample is typically divided, and one part is used for hematopoietic cell subtype characterisation and another part is used for lymphoid cell subtype characterisation.

Sample Coverage

The present invention allows the identification of, for example, up to 23 different hematopoietic cell subtypes in a single sample. The present invention also allows the relative frequency of, for example, up to 23 different hematopoietic cell subtypes in a single sample to be determined. The present invention also allows the quantification of the number of cells within, for example, up to 23 different hematopoietic cell subtypes in a single sample. This represents superior sample coverage to that provided by previous methods.

In particular, the sample coverage provided by the present invention is superior to that provided by prior art methods that rely on sub-dividing the sample and analysing several limited subsets of cell markers in multiple experiments. Similarly, the present invention provides superior coverage of hematopoietic cell subtypes relative to prior art methods that are directed to the identification and quantification of a single cell type of interest.

Accordingly, in some embodiments, greater than 95% of the hematopoietic cell subtypes in the sample are identified, preferably greater than 99% of the hematopoietic cell subtypes in the sample are identified, more preferably greater than 99.5% of the hematopoietic cell subtypes in the sample are identified, and even more preferably greater than 99.7%, 99.8%, or 99.9% of the cell subtypes in the sample are identified.

Kit

In another aspect, the present invention provides a kit comprising (i) an anti-CD3 antibody, (ii) an anti-CD56 antibody, (iii) an anti-CD14 antibody, (iv) an anti-CD38 antibody, (v) an anti-CD45 antibody, (vi) an anti-CD90 antibody, (vii) an anti-CD135 antibody, (viii) an anti-CD10 antibody, (ix) an anti-CD11c antibody, (x) an anti-CD19 antibody, (xi) an anti-CD34 antibody, (xii) an anti-CD45RA antibody, (xiii) an anti-CD7 antibody, (xiv) an anti-CD71 antibody, (xv) an anti-CD41/CD61 complex antibody or an anti-CD41 antibody and/or an anti-CD61 antibody (xvi) an anti-CD33 antibody and/or an anti-CD66b antibody, for identifying hematopoietic cell subtypes in an isolated sample, determining the relative frequency of hematopoietic cell subtypes in an isolated sample and/or quantifying the number of cells within hematopoietic cell subtypes in an isolated sample, wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome.

The kit may be for identifying, determining the relative frequency of and/or quantifying the number of cells within hematopoietic cell subtypes.

In one embodiment, the kit further comprises (B-i) an anti-CD3 antibody, (B-ii) an anti-CD56 antibody, (B-iii) an anti-CD45 antibody, (B-iv) an anti-CD19 antibody, (B-v) an anti-CD45RA antibody, (B-vi) an anti-CD33 antibody and/or an anti-CD66b antibody, (B-vii) an anti-CD4 antibody, (B-viii) an anti-CD8 antibody, (B-ix) an anti-CD95 antibody, (B-x) an anti-TCRγδ antibody, (B-xi) an anti-CD127 antibody, (B-xii) an anti-CD62L antibody, (B-xiii) an anti-CD25 antibody, wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome.

In another aspect, the present invention provides a kit comprising (B-i) an anti-CD3 antibody, (B-ii) an anti-CD56 antibody, (B-iii) an anti-CD45 antibody, (B-iv) an anti-CD19 antibody, (B-v) an anti-CD45RA antibody, (B-vi) an anti-CD33 antibody and/or an anti-CD66b antibody, (B-vii) an anti-CD4 antibody, (B-viii) an anti-CD8 antibody, (B-ix) an anti-CD95 antibody, (B-x) an anti-TCRγδ antibody, (B-xi) an anti-CD127 antibody, (B-xii) an anti-CD62L antibody, (B-xiii) an anti-CD25 antibody, wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome.

The kit may be for identifying, determining the relative frequency of and/or quantifying the number of cells within lymphoid cell subtypes.

Optionally, the kit may further comprise microspheres, preferably fluorescently-labelled microspheres, for providing an internal counting standard. As disclosed herein, a known number of such microspheres may be added to a sample to enable quantification of numbers of cells within the sample.

Optionally, the kit may further comprise a red blood cell lysis buffer.

In some embodiments, the kit further comprises a fluorescent cell viability marker. The fluorescent cell viability marker may be specific for either dead cells or live cells. In a preferred embodiment, the fluorescent cell viability marker is specific for dead cells. In some embodiments, the fluorescent cell viability maker is selected from propidium iodide (PI), propidium monoazide, ethidium monoazide, calcein AM, 7-aminoactinomycin (7-AAD), 4',6-diamidino-2-phenylindole (DAPI), and derivatives thereof. In a preferred embodiment, the fluorescent cell viability marker is propidium iodide (PI).

The antibodies of the kit may be provided in suitable containers.

The antibodies of the kit may be individually packaged and labelled.

Alternatively one or more of the antibodies of the kit may be packaged as a mixture of antibodies (e.g. an antibody cocktail). A mixture of antibodies may comprise two or more of said antibodies.

The kit may also include instructions for use.

Composition

In another aspect, the present invention provides a composition for identifying, determining the relative frequency of and/or quantifying the number of cells within hematopoietic cell subtypes comprising (i) an anti-CD3 antibody, (ii) an anti-CD56 antibody, (iii) an anti-CD14 antibody, (iv) an anti-CD38 antibody, (v) an anti-CD45 antibody, (vi) an anti-CD90 antibody, (vii) an anti-CD135 antibody, (viii) an anti-CD10 antibody, (ix) an anti-CD11c antibody, (x) an anti-CD19 antibody, (xi) an anti-CD34 antibody, (xii) an anti-CD45RA antibody, (xiii) an anti-CD7 antibody, (xiv) an anti-CD71 antibody, (xv) an anti CD41/CD61 complex antibody or an anti-CD41 antibody and/or an anti-CD61 antibody (xvi) an anti-CD33 antibody and/or an anti-CD66b antibody, wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome.

In one embodiment the composition further comprises (B-i) an anti-CD3 antibody, (B-ii) an anti-CD56 antibody, (B-iii) an anti-CD45 antibody, (B-iv) an anti-CD19 antibody, (B-v) an anti-CD45RA antibody, (B-vi) an anti-CD33 antibody and/or an anti-CD66b antibody, (B-vii) an anti-CD4 antibody, (B-viii) an anti-CD8 antibody, (B-ix) an anti-CD95 antibody, (B-x) an anti-TCRγδ antibody, (B-xi) an anti-CD127 antibody, (B-xii) an anti-CD62L antibody, (B-xiii) an anti-CD25 antibody, wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome.

In another aspect, the present invention provides a composition for identifying, determining the relative frequency of and/or quantifying the number of cells within lymphoid cell subtypes comprising (B-i) an anti-CD3 antibody, (B-ii) an anti-CD56 antibody, (B-iii) an anti-CD45 antibody, (B-iv) an anti-CD19 antibody, (B-v) an anti-CD45RA antibody, (B-vi) an anti-CD33 antibody and/or an anti-CD66b antibody, (B-vii) an anti-CD4 antibody, (B-viii) an anti-CD8 antibody, (B-ix) an anti-CD95 antibody, (B-x) an anti-TCRγδ antibody, (B-xi) an anti-CD127 antibody, (B-xii) an anti-CD62L antibody, (B-xiii) an anti-CD25 antibody, wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome.

Optionally, the composition may further comprise microspheres, preferably fluorescently-labelled microspheres, for providing an internal counting standard.

In some embodiments, the composition further comprises a fluorescent cell viability marker. The fluorescent cell viability marker may be specific for either dead cells or live cells. In a preferred embodiment, the fluorescent cell viability marker is specific for dead cells.

In some embodiments, the fluorescent cell viability maker is selected from propidium iodide (PI), propidium monoazide, ethidium monoazide, calcein AM, 7-aminoactinomycin (7-AAD), 4',6-diamidino-2-phenylindole (DAPI) and derivatives thereof. In a preferred embodiment, the fluorescent cell viability marker is propidium iodide (PI).

The composition may further comprise buffers, salts, counter ions, diluents, and/or excipients.

Antibodies for Use in Diagnosing a Blood Disorder

In another aspect the present invention provides an anti-CD90 antibody (i) for use in diagnosing a blood disorder, wherein the anti-CD90 antibody (i) is used in combination with an anti-CD3 antibody (ii), an anti-CD56 antibody (iii), an anti-CD14 antibody (iv), an anti-CD38 antibody (v), an anti-CD45 antibody (vi), an anti-CD135 antibody (vii), an anti-CD10 antibody (viii), an anti-CD11c antibody (ix), an anti-CD19 antibody (x), an anti-CD34 antibody (xi), an anti-CD45RA antibody (xii), an anti-CD7 antibody (xiii), an anti-CD71 antibody (xiv), an anti CD41/CD61 complex antibody or an anti-CD61 antibody and/or an anti-CD41 antibody (xv), an anti-CD33 antibody and/or an anti-CD66b antibody (xvi) wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome.

In another aspect the present invention provides an anti-CD3 antibody (i) for use in diagnosing a blood disorder, wherein the anti-CD3 antibody (i) is used in combination with an anti-CD90 antibody (ii), an anti-CD56 antibody (iii), an anti-CD14 antibody (iv), an anti-CD38 antibody (v), an anti-CD45 antibody (vi), an anti-CD135 antibody (vii), an anti-CD10 antibody (viii), an anti-CD11c antibody (ix), an anti-CD19 antibody (x), an anti-CD34 antibody (xi), an anti-CD45RA antibody (xii), an anti-CD7 antibody (xiii), an anti-CD71 antibody (xiv), an anti CD41/CD61 complex antibody or an anti-CD61 antibody and/or an anti-CD41 antibody (xv), an anti-CD33 antibody and/or an anti-CD66b antibody (xvi), wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome.

In another aspect the present invention provides an anti-CD56 antibody (i) for use in diagnosing a blood disorder, wherein the anti-CD56 antibody (i) is used in combination with an anti-CD90 antibody (ii), an anti-CD3 antibody (iii), an anti-CD14 antibody (iv), an anti-CD38 antibody (v), an anti-CD45 antibody (vi), an anti-CD135 antibody (vii), an anti-CD10 antibody (viii), an anti-CD11c antibody (ix), an anti-CD19 antibody (x), an anti-CD34 antibody (xi), an anti-CD45RA antibody (xii), an anti-CD7 antibody (xiii), an anti-CD71 antibody (xiv), an anti-CD41/CD61 complex antibody or an anti-CD41 antibody and/or an anti-CD61 antibody (xv), an anti-CD33 antibody and/or an anti-CD66b antibody (xvi), wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome.

In another aspect the present invention provides an anti-CD14 antibody (i) for use in diagnosing a blood disorder, wherein the anti-CD14 antibody (i) is used in combination with an anti-CD90 antibody (ii), an anti-CD3 antibody (iii), an anti-CD56 antibody (iv), an anti-CD38 antibody (v), an anti-CD45 antibody (vi), an anti-CD135 antibody (vii), an anti-CD10 antibody (viii), an anti-CD11c antibody (ix), an anti-CD19 antibody (x), an anti-CD34 antibody (xi), an anti-CD45RA antibody (xii), an anti-CD7 antibody (xiii), an anti-CD71 antibody (xiv), an anti-CD41/CD61 complex antibody or an anti-CD41 antibody and/or an anti-CD61 antibody (xv), an anti-CD33 antibody and/or an anti-CD66b antibody (xvi), wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome.

In another aspect the present invention provides an anti-CD38 antibody (i) for use in diagnosing a blood disorder, wherein the anti-CD38 antibody (i) is used in combination with an anti-CD90 antibody (ii), an anti-CD3 antibody (iii), an anti-CD56 antibody (iv), an anti-CD14 antibody (v), an anti-CD45 antibody (vi), an anti-CD135 antibody (vii), an anti-CD10 antibody (viii), an anti-CD11c antibody (ix), an anti-CD19 antibody (x), an anti-CD34 antibody (xi), an anti-CD45RA antibody (xii), an anti-CD7 antibody (xiii), an anti-CD71 antibody (xiv), an anti-CD41/CD61 complex antibody or an anti-CD41 antibody and/or an anti-CD61 antibody (xv), an anti-CD33 antibody and/or an anti-CD66b antibody (xvi), wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome.

In another aspect the present invention provides an anti-CD45 antibody (i) for use in diagnosing a blood disorder, wherein the anti-CD45 antibody (i) is used in combination with an anti-CD90 antibody (ii), an anti-CD3 antibody (iii), an anti-CD56 antibody (iv), an anti-CD14 antibody (v), an anti-CD38 antibody (vi), an anti-CD135 antibody (vii), an anti-CD10 antibody (viii), an anti-CD11c antibody (ix), an anti-CD19 antibody (x), an anti-CD34 antibody (xi), an anti-CD45RA antibody (xii), an anti-CD7 antibody (xiii), an anti-CD71 antibody (xiv), an anti-CD41/CD61 complex antibody or an anti-CD41 antibody and/or an anti-CD61 antibody (xv), an anti-CD33 antibody and/or an anti-CD66b antibody (xvi), wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome.

In another aspect the present invention provides an anti-CD135 antibody (i) for use in diagnosing a blood disorder, wherein the anti-CD135 antibody (i) is used in combination with an anti-CD90 antibody (ii), an anti-CD3 antibody (iii), an anti-CD56 antibody (iv), an anti-CD14 antibody (v), an anti-CD38 antibody (vi), an anti-CD45 antibody (vii), an anti-CD10 antibody (viii), an anti-CD11c antibody (ix), an anti-CD19 antibody (x), an anti-CD34 antibody (xi), an anti-CD45RA antibody (xii), an anti-CD7 antibody (xiii), an anti-CD71 antibody (xiv), an anti-CD41/CD61 complex antibody or an anti-CD41 antibody and/or an anti-CD61 antibody (xv), an anti-CD33 antibody and/or an anti-CD66b antibody (xvi), wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome.

In another aspect the present invention provides an anti-CD10 antibody (i) for use in diagnosing a blood disorder, wherein the anti-CD10 antibody (i) is used in combination with an anti-CD90 antibody (ii), an anti-CD3 antibody (iii), an anti-CD56 antibody (iv), an anti-CD14 antibody (v), an anti-CD38 antibody (vi), an anti-CD45 antibody (vii), an anti-CD135 antibody (viii), an anti-CD11c antibody (ix), an anti-CD19 antibody (x), an anti-CD34 antibody (xi), an anti-CD45RA antibody (xii), an anti-CD7 antibody (xiii), an anti-CD71 antibody (xiv), an anti-CD41/CD61 complex antibody or an anti-CD41 antibody and/or an anti-CD61 antibody (xv), an anti-CD33 antibody and/or an anti-CD66b antibody (xvi), wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome.

In another aspect the present invention provides an anti-CD11c antibody (i) for use in diagnosing a blood disorder, wherein the anti-CD11c antibody (i) is used in combination with an anti-CD90 antibody (ii), an anti-CD3 antibody (iii), an anti-CD56 antibody (iv), an anti-CD14 antibody (v), an anti-CD38 antibody (vi), an anti-CD45 antibody (vii), an anti-CD135 antibody (viii), an anti-CD10 antibody (ix), an anti-CD19 antibody (x), an anti-CD34 antibody (xi), an anti-CD45RA antibody (xii), an anti-CD7 antibody (xiii), an anti-CD71 antibody (xiv), an anti-CD41/CD61 complex antibody or an anti-CD41 antibody and/or an anti-CD61 antibody (xv), an anti-CD33 antibody and/or an anti-CD66b antibody (xvi), wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome.

In another aspect the present invention provides an anti-CD19 antibody (i) for use in diagnosing a blood disorder, wherein the anti-CD19 antibody (i) is used in combination with an anti-CD90 antibody (ii), an anti-CD3 antibody (iii), an anti-CD56 antibody (iv), an anti-CD14 antibody (v), an anti-CD38 antibody (vi), an anti-CD45 antibody (vii), an anti-CD135 antibody (viii), an anti-CD10 antibody (ix), an anti-CD11c antibody (x), an anti-CD34 antibody (xi), an anti-CD45RA antibody (xii), an anti-CD7 antibody (xiii), an anti-CD71 antibody (xiv), an anti-CD41/CD61 complex antibody or an anti-CD41 antibody and/or an anti-CD61 antibody (xv), an anti-CD33 antibody and/or an anti-CD66b antibody (xvi), wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome.

In another aspect the present invention provides an anti-CD34 antibody (i) for use in diagnosing a blood disorder, wherein the anti-CD34 antibody (i) is used in combination with an anti-CD90 antibody (ii), an anti-CD3 antibody (iii), an anti-CD56 antibody (iv), an anti-CD14 antibody (v), an anti-CD38 antibody (vi), an anti-CD45 antibody (vii), an anti-CD135 antibody (viii), an anti-CD10 antibody (ix), an anti-CD11c antibody (x), an anti-CD19 antibody (xi), an anti-CD45RA antibody (xii), an anti-CD7 antibody (xiii), an anti-CD71 antibody (xiv), an anti-CD41/CD61 complex antibody or an anti-CD41 antibody and/or an anti-CD61 antibody (xv), an anti-CD33 antibody and/or an anti-CD66b antibody (xvi), wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome.

In another aspect the present invention provides an anti-CD45RA antibody (i) for use in diagnosing a blood disorder, wherein the anti-CD45RA antibody (i) is used in combination with an anti-CD90 antibody (ii), an anti-CD3 antibody (iii), an anti-CD56 antibody (iv), an anti-CD14 antibody (v), an anti-CD38 antibody (vi), an anti-CD45 antibody (vii), an anti-CD135 antibody (viii), an anti-CD10 antibody (ix), an anti-CD11c antibody (x), an anti-CD19 antibody (xi), an anti-CD34 antibody (xii), an anti-CD7 antibody (xiii), an anti-CD71 antibody (xiv), an anti-CD41/CD61 complex antibody or an anti-CD41 antibody and/or an anti-CD61 antibody (xv), an anti-CD33 antibody and/or anti-CD66b antibody (xvi), wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome.

In another aspect the present invention provides an anti-CD7 antibody (i) for use in diagnosing a blood disorder, wherein the anti-CD7 antibody (i) is used in combination with an anti-CD90 antibody (ii), an anti-CD3 antibody (iii), an anti-CD56 antibody (iv), an anti-CD14 antibody (v), an anti-CD38 antibody (vi), an anti-CD45 antibody (vii), an anti-CD135 antibody (viii), an anti-CD10 antibody (ix), an anti-CD11c antibody (x), an anti-CD19 antibody (xi), an anti-CD34 antibody (xii), an anti-CD45RA antibody (xiii), an anti-CD71 antibody (xiv), an anti-CD41/CD61 complex antibody or an anti-CD41 antibody and/or an anti-CD61 antibody (xv), an anti-CD33 antibody and/or an anti-CD66b antibody (xvi), wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome.

In another aspect the present invention provides an anti-CD71 antibody (i) for use in diagnosing a blood disorder, wherein the anti-CD71 antibody (i) is used in combination with an anti-CD90 antibody (ii), an anti-CD3 antibody (iii), an anti-CD56 antibody (iv), an anti-CD14 antibody (v), an anti-CD38 antibody (vi), an anti-CD45 antibody (vii), an anti-CD135 antibody (viii), an anti-CD10 antibody (ix), an anti-CD11c antibody (x), an anti-CD19 antibody (xi), an anti-CD34 antibody (xii), an anti-CD45RA antibody (xiii), an anti-CD7 antibody (xiv), an anti-CD41/CD61 complex antibody or an anti-CD41 antibody and/or an anti-CD61 antibody (xv), an anti-CD33 antibody and/or an anti-CD66b antibody (xvi), wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome.

In another aspect the present invention provides an anti-CD41/CD61 complex antibody or an anti-CD41 antibody and/or an anti-CD61 antibody (i) for use in diagnosing a blood disorder, wherein the anti-CD41/CD61 complex antibody or the anti-CD41 antibody and/or anti-CD61 antibody (i) is used in combination with an anti-CD90 antibody (ii), an anti-CD3 antibody (iii), an anti-CD56 antibody (iv), an anti-CD14 antibody (v), an anti-CD38 antibody (vi), an anti-CD45 antibody (vii), an anti-CD135 antibody (viii), an anti-CD10 antibody (ix), an anti-CD11c antibody (x), an anti-CD19 antibody (xi), an anti-CD34 antibody (xii), an anti-CD45RA antibody (xiii), an anti-CD7 antibody (xiv), an anti-CD71 antibody (xv), an anti-CD33 antibody and/or an anti-CD66b antibody (xvi), wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (i) is an anti-CD41 antibody and an anti-CD61 antibody, the anti-CD41 antibody and the anti-CD61 antibody are labelled with the same fluorochrome.

In another aspect the present invention provides an anti-CD33 antibody and/or an anti-CD66b antibody (i) for use in diagnosing a blood disorder, wherein the anti-CD33 antibody and/or anti-CD66b antibody (i) is used in combination with an anti-CD90 antibody (ii), an anti-CD3 antibody (iii), an anti-CD56 antibody (iv), an anti-CD14 antibody (v), an anti-CD38 antibody (vi), an anti-CD45 antibody (vii), an anti-CD135 antibody (viii), an anti-CD10 antibody (ix), an anti-CD11c antibody (x), an anti-CD19 antibody (xi), an anti-CD34 antibody (xii), an anti-CD45RA antibody (xiii), an anti-CD7 antibody (xiv), an anti-CD71 antibody (xv), an anti-CD41/CD61 complex antibody or an anti-CD41 antibody and/or an anti-CD61 antibody (xvi), wherein each of (i) to (xvi) is labelled with a different fluorochrome, wherein when (i) is an anti-CD33 antibody and an anti-CD66b antibody, the anti-CD33 antibody and anti-CD66b are labelled with the same fluorochrome, and wherein when (xvi) is an anti-CD41 antibody and an anti-CD61 antibody, the anti-CD41 antibody and the anti-CD61 antibody are labelled with the same fluorochrome.

In another aspect, the present invention provides an anti-CD3 antibody (B-i) for use in diagnosing a blood disorder, wherein the anti-CD3 antibody (B-i) is used in combination with an anti-CD56 antibody (B-ii), an anti-CD45 antibody (B-iii), an anti-CD19 antibody (B-iv), an anti-CD45RA antibody (B-v), an anti-CD33 antibody and/or an anti-CD66b antibody (B-vi), an anti-CD4 antibody (B-vii), an anti-CD8 antibody (B-viii), an anti-CD95 antibody (B-ix), an anti-TCRγδ antibody (B-x), an anti-CD127 antibody (B-xi), an anti-CD62L antibody (B-xii), an anti-CD25 antibody (B-xiii), wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome.

In another aspect, the present invention provides an anti-CD56 antibody (B-i) for use in diagnosing a blood disorder, wherein the anti-CD56 antibody (B-i) is used in combination with an anti-CD3 antibody (B-ii), an anti-CD45 antibody (B-iii), an anti-CD19 antibody (B-iv), an anti-CD45RA antibody (B-v), an anti-CD33 antibody and/or an anti-CD66b antibody (B-vi), an anti-CD4 antibody (B-vii), an anti-CD8 antibody (B-viii), an anti-CD95 antibody (B-ix), an anti-TCRγδ antibody (B-x), an anti-CD127 antibody (B-xi), an anti-CD62L antibody (B-xii), an anti-CD25 antibody (B-xiii), wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome.

In another aspect, the present invention provides an anti-CD45 antibody (B-i) for use in diagnosing a blood disorder, wherein the anti-CD45 antibody (B-i) is used in combination with an anti-CD56 antibody (B-ii), an anti-CD3 antibody (B-iii), an anti-CD19 antibody (B-iv), an anti-CD45RA antibody (B-v), an anti-CD33 antibody and/or an anti-CD66b antibody (B-vi), an anti-CD4 antibody (B-vii), an anti-CD8 antibody (B-viii), an anti-CD95 antibody (B-ix), an anti-TCRγδ antibody (B-x), an anti-CD127 antibody (B-xi), an anti-CD62L antibody (B-xii), an anti-CD25 antibody (B-xiii), wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome.

In another aspect, the present invention provides an anti-CD19 antibody (B-i) for use in diagnosing a blood disorder, wherein the anti-CD19 antibody (B-i) is used in combination with an anti-CD56 antibody (B-ii), an anti-CD45 antibody (B-iii), an anti-CD3 antibody (B-iv), an anti-CD45RA antibody (B-v), an anti-CD33 antibody and/or an anti-CD66b antibody (B-vi), an anti-CD4 antibody (B-vii), an anti-CD8 antibody (B-viii), an anti-CD95 antibody (B-ix), an anti-TCRγδ antibody (B-x), an anti-CD127 antibody (B-xi), an anti-CD62L antibody (B-xii), an anti-CD25 antibody (B-xiii), wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome.

In another aspect, the present invention provides an anti-CD45RA antibody (B-i) for use in diagnosing a blood disorder, wherein the anti-CD45RA antibody (B-i) is used in combination with an anti-CD56 antibody (B-ii), an anti-CD45 antibody (B-iii), an anti-CD19 antibody (B-iv), an anti-CD3 antibody (B-v), an anti-CD33 antibody and/or an anti-CD66b antibody (B-vi), an anti-CD4 antibody (B-vii), an anti-CD8 antibody (B-viii), an anti-CD95 antibody (B-ix), an anti-TCRγδ antibody (B-x), an anti-CD127 antibody (B-xi), an anti-CD62L antibody (B-xii), an anti-CD25 antibody (B-xiii), wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome.

In another aspect, the present invention provides an anti-CD33 antibody and/or an anti-CD66b antibody (B-i) for use in diagnosing a blood disorder, wherein the anti-CD33 antibody and/or anti-CD66b antibody (B-i) is used in combination with an anti-CD56 antibody (B-ii), an anti-CD45 antibody (B-iii), an anti-CD19 antibody (B-iv), an anti-CD45RA antibody (B-v), an anti-CD3 antibody (B-vi), an anti-CD4 antibody (B-vii), an anti-CD8 antibody (B-viii), an anti-CD95 antibody (B-ix), an anti-TCRγδ antibody (B-x), an anti-CD127 antibody (B-xi), an anti-CD62L antibody (B-xii), an anti-CD25 antibody (B-xiii), wherein each of (B-i) to (B-xiii) is labelled with a different fluorochrome, wherein when (B-i) is an anti-CD33 antibody and an anti-CD66b antibody, the anti-CD33 antibody and anti-CD66b are labelled with the same fluorochrome.

In another aspect, the present invention provides an anti-CD4 antibody (B-i) for use in diagnosing a blood disorder, wherein the anti-CD4 antibody (B-i) is used in combination with an anti-CD56 antibody (B-ii), an anti-CD45 antibody (B-iii), an anti-CD19 antibody (B-iv), an anti-CD45RA antibody (B-v), an anti-CD33 antibody and/or an anti-CD66b antibody (B-vi), an anti-CD3 antibody (B-vii), an anti-CD8 antibody (B-viii), an anti-CD95 antibody (B-ix), an anti-TCRγδ antibody (B-x), an anti-CD127 antibody (B-xi), an anti-CD62L antibody (B-xii), an anti-CD25 antibody (B-xiii), wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome.

In another aspect, the present invention provides an anti-CD8 antibody (B-i) for use in diagnosing a blood disorder, wherein the anti-CD8 antibody (B-i) is used in combination with an anti-CD56 antibody (B-ii), an anti-CD45 antibody (B-iii), an anti-CD19 antibody (B-iv), an anti-CD45RA antibody (B-v), an anti-CD33 antibody and/or an anti-CD66b antibody (B-vi), an anti-CD4 antibody (B-vii), an anti-CD3 antibody (B-viii), an anti-CD95 antibody (B-ix), an anti-TCRγδ antibody (B-x), an anti-CD127 antibody (B-xi), an anti-CD62L antibody (B-xii), an anti-CD25 antibody (B-xiii), wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome.

In another aspect, the present invention provides an anti-CD95 antibody (B-i) for use in diagnosing a blood disorder, wherein the anti-CD95 antibody (B-i) is used in combination with an anti-CD56 antibody (B-ii), an anti-CD45 antibody (B-iii), an anti-CD19 antibody (B-iv), an anti-CD45RA antibody (B-v), an anti-CD33 antibody and/or an anti-CD66b antibody (B-vi), an anti-CD4 antibody (B-vii), an anti-CD8 antibody (B-viii), an anti-CD3 antibody (B-ix), an anti-TCRγδ antibody (B-x), an anti-CD127 antibody (B-xi), an anti-CD62L antibody (B-xii), an anti-CD25 antibody (B-xiii), wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome.

In another aspect, the present invention provides an anti-TCRγδ antibody (B-i) for use in diagnosing a blood disorder, wherein the anti-TCRγδ antibody (B-i) is used in combination with an anti-CD56 antibody (B-ii), an anti-CD45 antibody (B-iii), an anti-CD19 antibody (B-iv), an anti-CD45RA antibody (B-v), an anti-CD33 antibody and/or an anti-CD66b antibody (B-vi), an anti-CD4 antibody (B-vii), an anti-CD8 antibody (B-viii), an anti-CD95 antibody (B-ix), an anti-CD3 antibody (B-x), an anti-CD127 antibody (B-xi), an anti-CD62L antibody (B-xii), an anti-CD25 antibody (B-xiii), wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome.

In another aspect, the present invention provides an anti-CD127 antibody (B-i) for use in diagnosing a blood disorder, wherein the anti-CD127 antibody (B-i) is used in combination with an anti-CD56 antibody (B-ii), an anti-CD45 antibody (B-iii), an anti-CD19 antibody (B-iv), an anti-CD45RA antibody (B-v), an anti-CD33 antibody and/or an anti-CD66b antibody (B-vi), an anti-CD4 antibody (B-vii), an anti-CD8 antibody (B-viii), an anti-CD95 antibody (B-ix), an anti-TCRγδ antibody (B-x), an anti-CD3 antibody (B-xi), an anti-CD62L antibody (B-xii), an anti-CD25 antibody (B-xiii), wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome.

In another aspect, the present invention provides an anti-CD62L antibody (B-i) for use in diagnosing a blood disorder, wherein the anti-CD62L antibody (B-i) is used in combination with an anti-CD56 antibody (B-ii), an anti-CD45 antibody (B-iii), an anti-CD19 antibody (B-iv), an anti-CD45RA antibody (B-v), an anti-CD33 antibody and/or an anti-CD66b antibody (B-vi), an anti-CD4 antibody (B-vii), an anti-CD8 antibody (B-viii), an anti-CD95 antibody (B-ix), an anti-TCRγδ antibody (B-x), an anti-CD127 antibody (B-xi), an anti-CD3 antibody (B-xii), an anti-CD25 antibody (B-xiii), wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome.

In another aspect, the present invention provides an anti-CD25 antibody (B-i) for use in diagnosing a blood disorder, wherein the anti-CD25 antibody (B-i) is used in combination with an anti-CD56 antibody (B-ii), an anti-CD45 antibody (B-iii), an anti-CD19 antibody (B-iv), an anti-CD45RA antibody (B-v), an anti-CD33 antibody and/or an anti-CD66b antibody (B-vi), an anti-CD4 antibody (B-vii), an anti-CD8 antibody (B-viii), an anti-CD95 antibody (B-ix), an anti-TCRγδ antibody (B-x), an anti-CD127 antibody (B-xi), an anti-CD62L antibody (B-xii), an anti-CD3 antibody (B-xiii), wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome.

As used herein the term "blood disorder" refers to a disease or conditions associated with an unbalanced distribution of hematopoietic cell subtypes. The unbalanced distribution of hematopoietic cell subtypes may in the PB and/or the BM. An unbalanced distribution of cells refers to a relative frequency of hematopoietic cell subtypes that is significantly different to the relative frequency observed in a corresponding healthy control sample. Accordingly, the present invention is useful for diagnosing such blood disorders since it allows the relative frequency of hematopoietic cells in a sample isolated from PB or BM sample to be determined. Blood disorders may also be diagnosed using the present invention by quantification of the number of cells within hematopoietic cell subtypes in a sample. For example, absolute cell quantification allows the testing of whether each cell compartment is within the normal range of cellularity (e.g. by comparison to the cellularity observed in a corresponding healthy control sample).

In some embodiments, the antibodies for use in diagnosing a blood disorder are contacted with an isolated sample obtained from an individual who is at risk of blood disorder, is suspected of having a blood disorder, or has a blood disorder, or has previously had a blood disorder. The individual may be in remission.

In some embodiments, the individual may be diagnosed with a blood disorder if the relative frequency of hematopoietic cell subtypes is significantly different to a control.

In some embodiments, the individual may be diagnosed with a blood disorder if the number of cells of one or more hematopoietic cell subtypes is significantly different to a control.

The control may be a control sample. For example, the control sample may be isolated from an aged matched healthy individual. Alternatively, the control may be a dataset comprising relative frequencies of or absolute numbers of cells within hematopoietic cell subtypes that have been previously determined for a healthy individual or a population of healthy individuals.

The individual may be diagnosed with a blood disorder if the relative frequency of or absolute numbers of cells within one or more of the following hematopoietic cell subtypes is increased or decreased relative to a control: immature polymorphonuclear leukocytes (iPMN), polymorphonuclear leukocytes (PMN), monocytes, dendritic cells (DC)/DC progenitors, myeloblasts, T-cells, natural killer T cells (NKT), natural killer cells (NK), B-cells, pre-B cells, pro-B cells, pro-lymphocytes, pro-erythroblasts, erythroblasts, hematopoietic stem cells (HSC), multipotent progenitors (MPP), multipotent lymphoid progenitors (MLP), early T progenitors (ETP) cells, pre-B/natural killer cells (PRE-B/NK), common myeloid progenitors (CMP), granulocyte/macrophage progenitors (GMP), and megakaryocyte/erythrocyte progenitors (MEP).

In some embodiments, the blood disorder is a blood cancer; preferably the blood cancer is a leukaemia. In a preferred embodiment, the blood disorder is acute myeloid leukemia (AML) or acute lymphocytic leukemia (ALL)

In some embodiments, the blood disorder is not a blood cancer.

In some embodiments, the blood disorder is a primary immune deficiency (PID). In one embodiment, the PID is adenosine deaminase deficiency severe combined immunodeficiency (ADA-SCID) or Wiskott Aldrich syndrome (WAS).

The blood disorder may be beta thalassemia, chronic granulomatous disease (CGD), X-linked severe combined immunodeficiency (X-SCID), other PID, or other hematopoietic disorders.

The blood disorder may be a chronic lymphoid leukaemia (CLL), a chronic myeloid leukaemia (CML), or a multiple myeloma (MM). The blood disorder may be another type of blood cancer.

The blood disorder may be at the onset, during or after treatment, or at relapse.

The present invention may be used to monitor or diagnose minimal residual disease (MRD). MRD refers to diseased or abnormal cells that remain in a patient following treatment, e.g. for a blood cancer. This remaining population of cells may be present at a very low frequency and are therefore difficult to detect by conventional techniques. However, this residual cell population may cause a relapse in the patient if the frequency of such cells increases. Since the use, method, kit, composition and antibodies described herein may be used to determine the relative frequency of hematopoietic cell types, the present invention may be useful for monitoring MRD.

Accordingly, in another aspect, the present invention provides a method for monitoring minimal residual disease (MRD) in a patient comprising the steps of:
(a) contacting an isolated sample obtained from the patient with (i) an anti-CD3 antibody, (ii) an anti-CD56 antibody, (iii) an anti-CD14 antibody, (iv) an anti-CD38 antibody, (v) an anti-CD45 antibody, (vi) an anti-CD90 antibody, (vii) an anti-CD135 antibody, (viii) an anti-CD10 antibody, (ix) an anti-CD11c antibody, (x) an anti-CD19 antibody, (xi) an anti-CD34 antibody, (xii) an anti-CD45RA antibody, (xiii) an anti-CD7 antibody, (xiv) an anti-CD71 antibody, (xv) an anti-CD41/CD61 complex antibody or an anti-CD41 antibody and/or an anti-CD61 antibody (xvi) an anti-CD33 antibody and/or an anti-CD66b antibody, wherein each of (i) to (xvi) is labelled with a different fluorochrome,
wherein when (xvi) is an anti-CD33 antibody and an anti-CD66b antibody, the anti-CD33 antibody and anti-CD66b are labelled with the same fluorochrome, and
wherein when (xv) is an anti-CD41 antibody and an anti-CD61 antibody, the anti-CD41 antibody and the anti-CD61 antibody are labelled with the same fluorochrome;
(b) detecting fluorochrome labelled hematopoietic cells.

In one embodiment, the method may comprise the further steps of:
(c) providing another part of the sample, which part has not been used in step (a) and/or (b);
(d) contacting the sample of step (c) with (B-i) an anti-CD3 antibody, (B-ii) an anti-CD56 antibody, (B-iii) an anti-CD45 antibody, (B-iv) an anti-CD19 antibody, (B-v) an anti-CD45RA antibody, (B-vi) an anti-CD33 antibody and/or an anti-CD66b antibody, (B-vii) an anti-CD4 antibody, (B-viii) an anti-CD8 antibody, (B-ix) an anti-CD95 antibody, (B-x) an anti-TCRγδ antibody, (B-xi) an anti-CD127 antibody, (B-xii) an anti-CD62L antibody, (B-xiii) an anti-CD25 antibody, wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome;

(e) detecting fluorochrome labelled lymphoid cells.

The patient may be in remission. The patient may have been previously treated for a blood disorder.

In some embodiments, one or more of the following hematopoietic cell subtypes are identified: immature polymorphonuclear leukocytes (iPMN), polymorphonuclear leukocytes (PMN), monocytes, dendritic cells (DC)/DC progenitors, myeloblasts, T-cells, natural killer T cells (NKT), natural killer cells (NK), B-cells, pre-B cells, pro-B cells, pro-lymphocytes, pro-erythroblasts, erythroblasts, hematopoietic stem cells (HSC), multipotent progenitors (MPP), multipotent lymphoid progenitors (MLP), early T progenitors (ETP) cells, pre-B/natural killer cells (PRE-B/NK), common myeloid progenitors (CMP), granulocyte/macrophage progenitors (GMP), and megakaryocyte/erythrocyte progenitors (MEP).

All publications mentioned in the above specification are herein incorporated by reference. Various modifications and variations of the described present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in cell biology, molecular biology, histology, immunology, oncology, or related fields are intended to be within the scope of the following claims.

Various preferred features and embodiments of the present invention will now be described by way of non-limiting examples.

EXAMPLES

Example 1

Protocol for Determining the Relative Frequency of Hematopoietic Cell Subtypes Present in an Isolated Sample Reagent Preparation RBC lysis buffer: dissolve NH$_4$Cl (Sigma, final concentration: 0.15 M), KHCO$_3$ (Fluka BioChemika, final concentration 10 mM) and EDTA Tetrasodium (Fluka BioChemika, final concentration: 0.10 mM) in H$_2$O. Filter the solution with 0.2 µm membrane filter and store at +4° C. for up to three months.

PBS-FACS: prepare the solution adding Bovine Serum Albumin (BSA) (Roche) 0.3% and Na—N$_3$ (Sigma) 0.1% to PBS without Calcium and Magnesium (Gibco). Filter the solution with 0.2 µm membrane filter and store at +4° C.

WORKING SOLUTION (WS): prepare RPMI (Corning) medium complemented with 10% FBS (EuroClone), 1% Pen/Strep and 1% L-Glutammine (Lonza). Dilute the complete medium in PBS without Calcium and Magnesium at 1:1 ratio. Add Hepes (Sigma) to the final concentration of 25 mM. Filter the solution with 0.2 µm membrane filter and store at +4° C.

Staining Protocol

To prepare the samples for FACS acquisition follow the steps below.
1. Collect 100 µl of WB from BM or 500 µl of WB from PB in a FACS tube.
2. Add 1 ml (BM) or 3 ml (PB) of cold RBC lysis buffer. Vortex the sample to allow efficient RBC lysis.
3. Leave the sample stands for 5 minutes at room temperature (RT).
4. Wash with 2 ml of PBS 1×.
5. Centrifuge for 5 minutes at 1500 rpm at RT and remove the supernatant.
6. Wash the sample with 1 ml of PBS-FACS. Centrifuge for 5 minutes at 1500-RPM RT and remove the supernatant.
7. Resuspend the cell pellet in 100 µl of PBS-FACS.
8. Add to the cell suspension the mix of fluorochrome-labelled antibodies (Table 2). Carefully mix by pipetting several times.
9. Incubate for 30 minutes at RT in the dark.
10. Wash with 2 ml of PBS-FACS.
11. Centrifuge for 5 minutes at 1500 rpm RT and remove the supernatant.
12. Resuspend the sample in 100 µl of PBS-FACS
13. Add 5 µl of propidium iodide at final concentration of 0.25 µg/ml. Mix the cell suspension.
14. Incubate for 15 minutes at RT in the dark.
15. Add 300 µl of PBS-FACS.
16. Keep the sample at +4° C. in the dark until the acquisition.
17. Acquire the sample using LSR-Fortessa (BD) cytometer

TABLE 2

Table summarising the antibodies marker specificity and their fluorochrome labels.

| Marker | Fluorochrome |
| --- | --- |
| CD3 | BV605 |
| CD56 | PE-Cy5 |
| CD14 | BV510 |
| CD33 | BB515 |
| CD61/41 | Pe-Cy7 |
| CD66b | BB515 |
| CD38 | BUV737 |
| CD45 | BUV395 |
| CD90 | APC |
| CD135 | PE |
| CD10 | BV786 |
| CD11c | BV650 |
| CD19 | APC-R700 |
| CD34 | BV421 |
| CD45RA | APC-Cy7 |
| CD7 | PerCP-Cy5.5 |
| CD71 | BV711 |

Flow Cytometric Data Acquisition

Single-coloured beads are acquired in order to set the PMT voltages and to create a compensation matrix (CM) to avoid spectral overlaps and unwanted fluorescence spill over. After CM generation, titration assay is required to define the best fluorochrome-labelled antibody concentration and fluorescent minus one (FMO) controls are run to set the correct positive gates for the down-stream data analyses. Rainbow beads (RB) calibration completes the instrument set up and RB acquisition is performed before each sample acquisition in order to provide reproducible instrument settings between different experiments. All samples were acquired through BD LSR-Fortessa (BD Bioscience) cytofluorimeter after Rainbow beads (Spherotech) calibration and raw data were collected through DIVA software (BD Biosciences). The data were subsequently analysed with FlowJo software Version 9.3.2 (TreeStar) and the graphical output was automatically generated through Prism 6.0c (GraphPad software).

Main Gating Strategy

Figure 6:
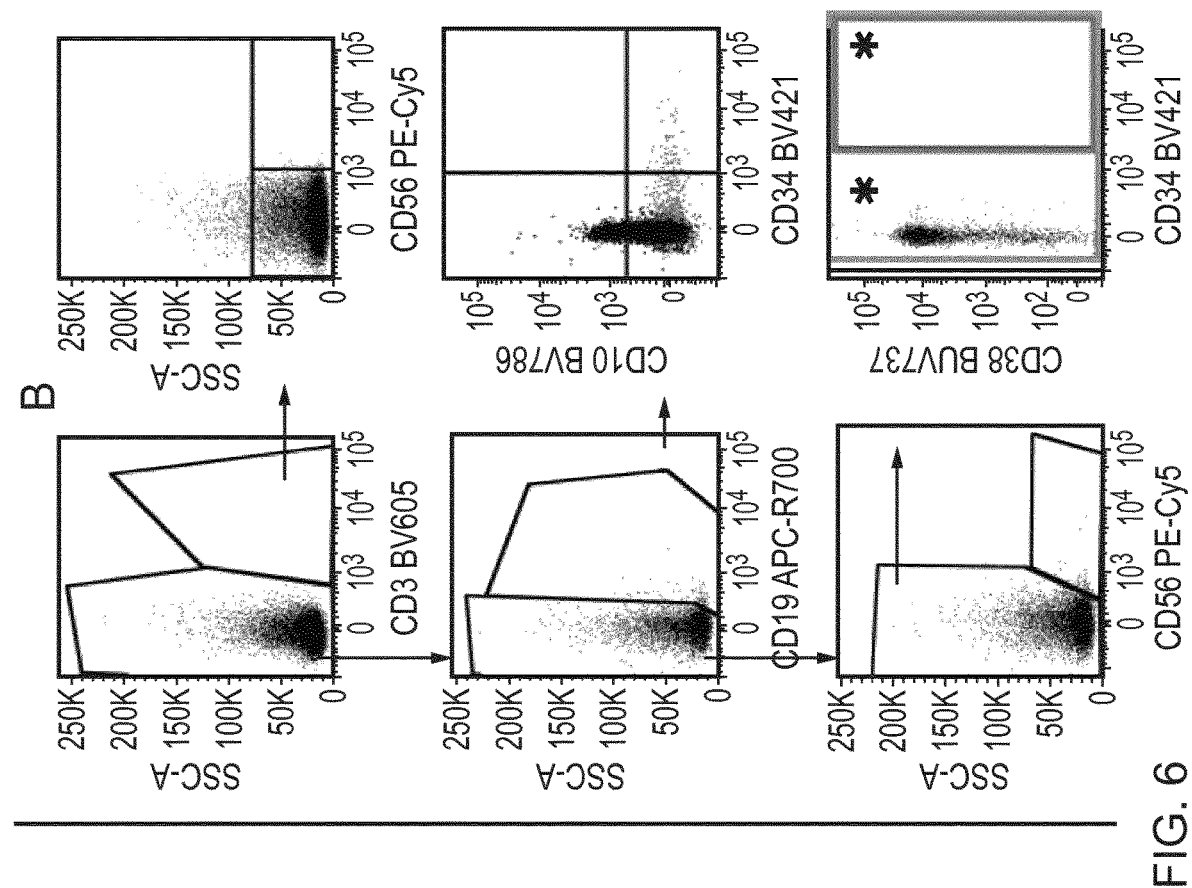
Figure 6:
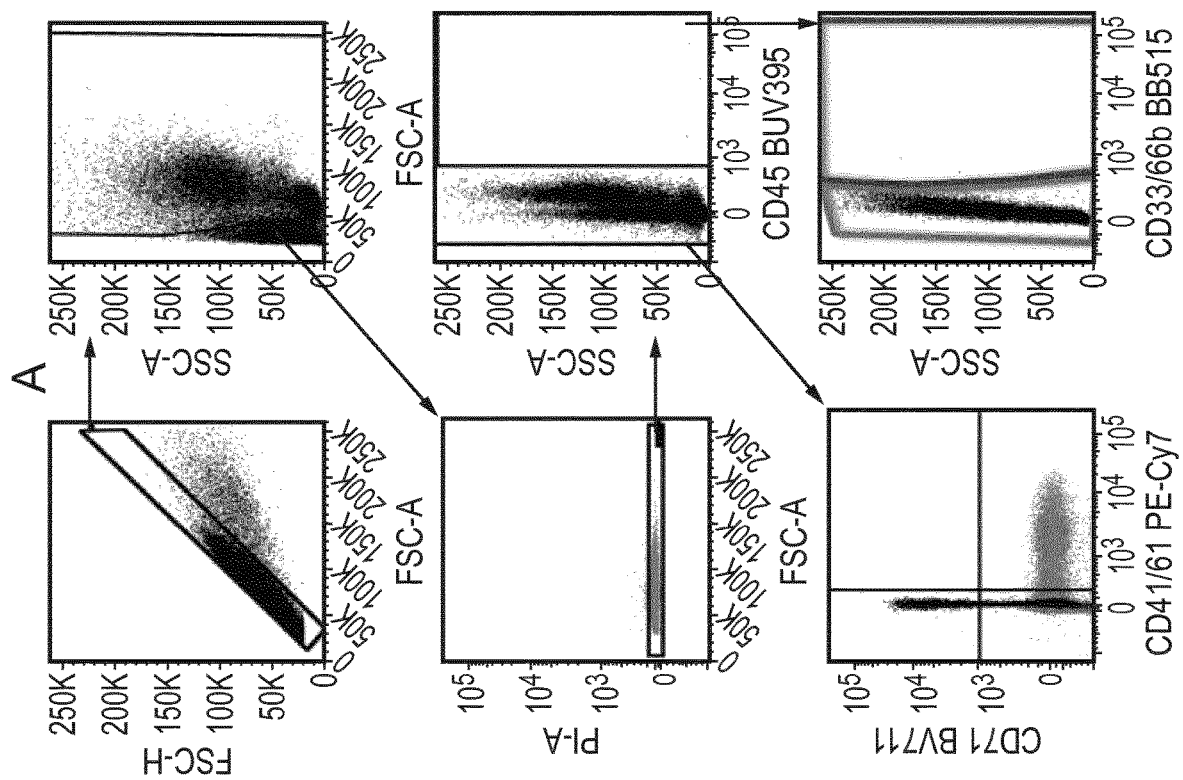
Figure 6:
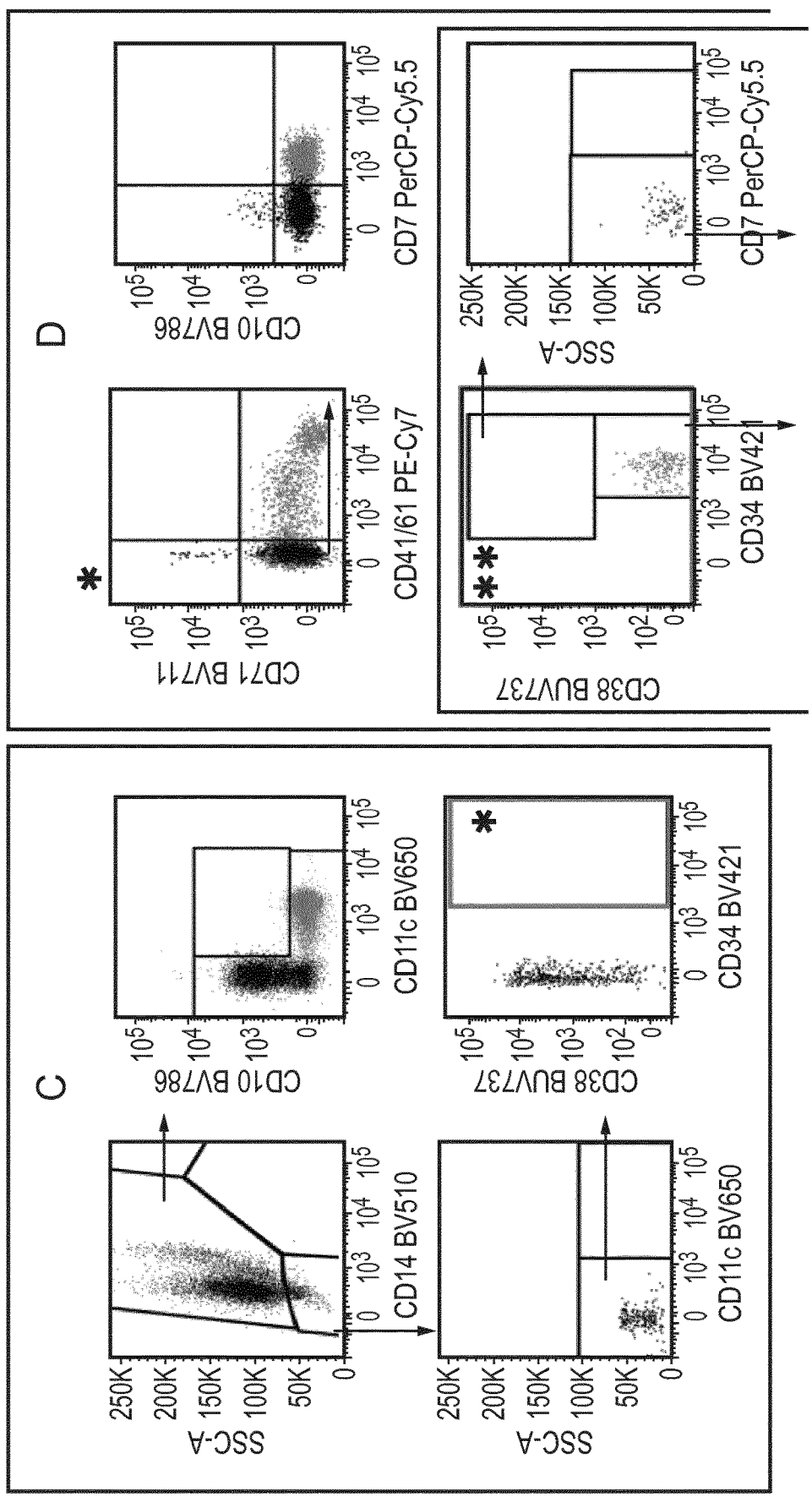
Figure 6:
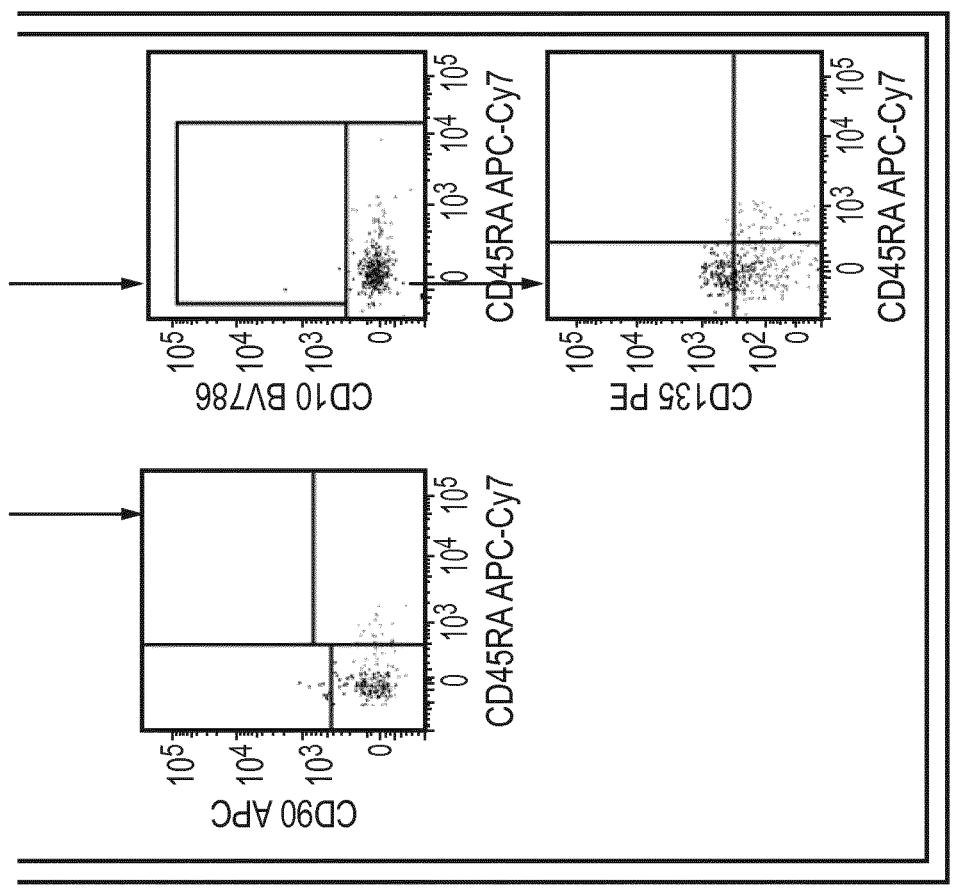
Figure 7:
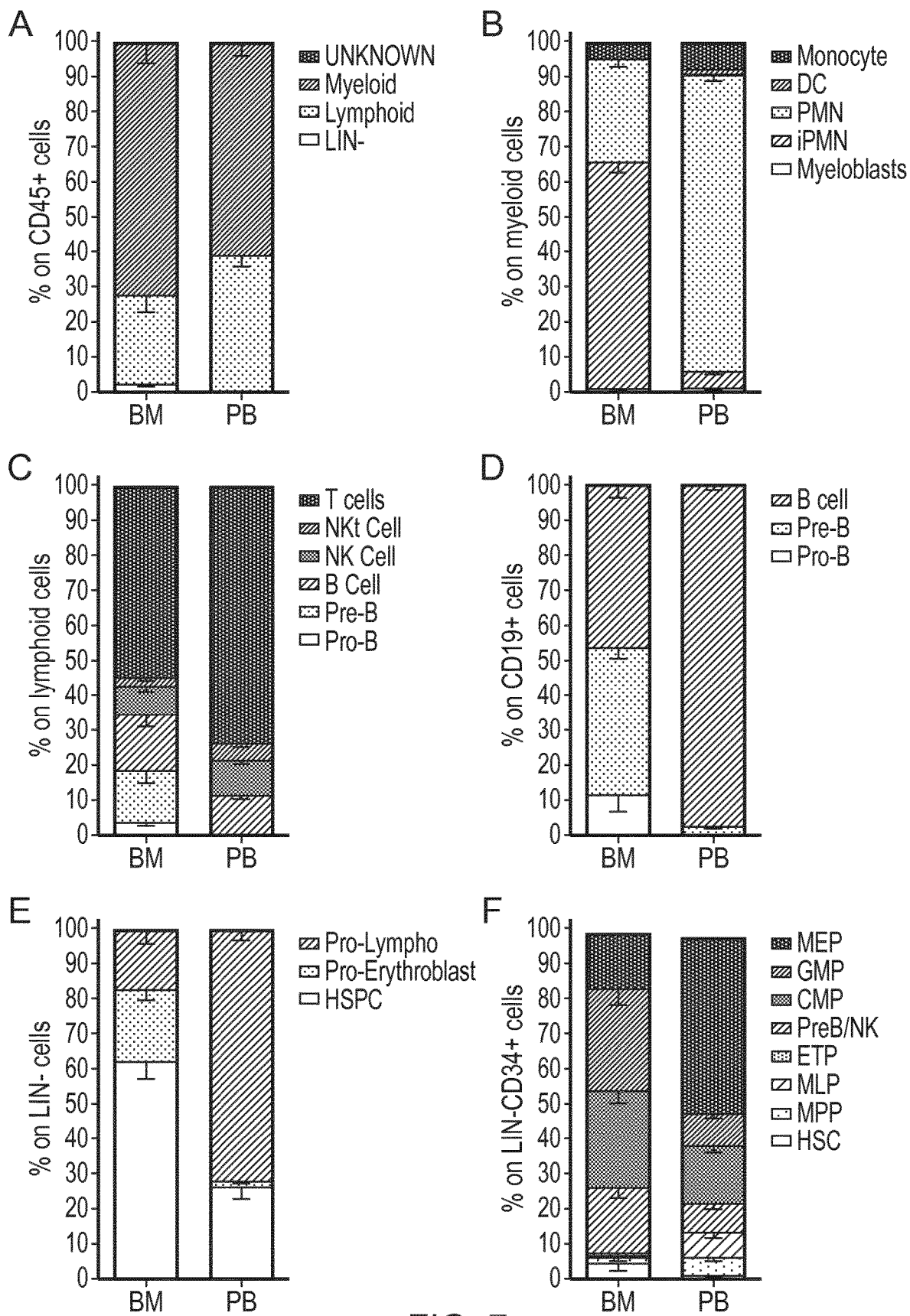

After data acquisition FCS files using are exported and analyzed using FlowJo (TreeStar) or similar software according to the following gating strategy (FIG. 6):

1. Create a dot plot FSC-H/FSC-A to identify single cells (G1).
2. Create on G1 a dot plot SSC-A/FSC-A to identify the cells-size population (G2).
3. Create on G2 a dot plot PI-A/FSC-A to select live cells (low PI-A) (G3). From now on each gate has to be set according to its respective FMO control.
4. Create on G3 a dot plot SSC-A/BUV395-A to evaluate the expression of CD45 maker and create a gate on negative (G4) and on positive events (G5).
5. Create on G4 a dot plot BV711-A/PE-Cy7-A to evaluate the expression of CD71 and CD41/61 markers. Create a gate on CD71+ (G6; Erythroblasts), CD41/61+ (G7; Platelets) and double negative events (G8).
6. Create on G5 a dot plot SSC-A/BB515-A to evaluate the expression of CD33/CD66b markers. Create a gate on negative (G9; not-myeloid cells) and positive events (G10; myeloid cells).
7. Create on G10 a dot plot SSC-A/BV510-A to evaluate the expression of CD14 marker and cell granularity (SSC-A). Create a gate on CD14+ (G11; Monocytes), on high granularity events (G12) and on negative events (G13).
8. Create on G12 a dot plot BV786-A/BV650-A to evaluate the expression of CD10 and CD11c markers and create a gate on double positive events (G14; PMN) and on remaining events (G15; iPMN).
9. Create on G13 a dot plot SSC-A/BV650-A to evaluate the expression of CD11c marker and create a gate on positive (G16; DC) and negative events (G17).
10. Create on G17 a dot plot BUV737-A/BV421-A to evaluate the expression of CD38 and CD34 markers. Create a gate on CD34 negative (G18; Myeloblasts) and CD34 positive events (G19; myeloid-committed progenitors).
11. Create on G9 a dot plot SSC-A/BV605-A to evaluate the expression of CD3 marker and create a gate on positive (G20) and negative events (G21).
12. Create on G20 a dot plot SSC-A/PE-Cy5-A to evaluate the expression of CD56 and create a gate on positive (G22; NKT) and negative events (G23; T cell).
13. Create on G21 a dot plot SSC-A/APC-R700-A to evaluate the expression of CD19 marker and create a gate on positive (G24; CD19+ lymphocytes) and negative (G25) events.
14. Create on G24 a dot plot BV785-A/BV421-A to evaluate the expression of CD10 and CD34 markers and create a gate on double positive (G26; Pro-B), double negative (G27; B cells), CD10+ only (G28; Pre-B) and CD34+only (G29) events.
15. Create on G25 a dot plot SSC-A/PE-Cy5-A to evaluate the expression of CD56 marker and create a gate on positive (G30; NK) and negative (G31; LIN−) events.
16. Create on G31 a dot plot BUV737-A/BV421-A to evaluate the expression of CD38 and CD34 markers and create a gate on CD34+ (G32) and CD34− (G33) events.
17. Create on G33 a dot plot BV711-A/PE-Cy7-A to evaluate the expression of CD71 and CD41/61 markers and create a gate on double negative (G34), CD71+ only (G35; Pro-erythroblasts) and CD41/61+ only (G36; Immature Platelets) events.
18. Create on G34 a dot plot BV785-A/PerCP-Cy5.5-A to evaluate the expression of CD10 and CD7 markers and create a gate on double negative (G37), CD10+ only (G38) and CD7+ only (G39) events. G38+G39: Pro-lymphocytes 19. Create on merged G19+G32 a dot plot BV785-A/CD421-A to evaluate the expression of CD38 and CD34 markers. All the events should be CD34+. Create a gate on CD38+ (G40) and CD38− (G41) events.
20. Create on G41 a dot plot APC-A/APC-Cy7-A to evaluate the expression of CD90 and CD45RA markers and create a gate on CD90+only (G42; HSC), double negative (G43; MPP) and CD45RA+ (G44; MLP) events.
21. Create on G40 a dot plot SSC-A/PerCP-Cy5.5-A to evaluate the expression of CD7 marker and create a gate on CD7+ (G45; ETP) and CD7− (G46) events.
22. Create on G46 a dot plot BV785-A/APC-Cy7-A to evaluate the expression of CD10 and CD45RA markers and create a gate on CD10+ (G47; Pre-B/NK) and CD10− (G48) events.
23. Create on G48 a dot plot PE-A/APC-Cy7-A to evaluate the expression of CD135 and CD45RA markers and create a gate on CD135+ only (G49; CMP), double positive (G50; GMP) and double negative (G51; MEP) events.
24. Create a table with the percentages of all gates on their paternal gate and calculate the overall percentages on the total CD45+ cells (gate G5).
25. Graphical output is generated with Prism 6.0c (GraphPad software) setting a layout with a "Part of Whole" ring plot for all cell populations, percentages on total CD45+ cells, and with a "Grouped" bar for HSPC subpopulations, percentages on total CD34+LIN− cells.

Alternative Gating Strategy

After data acquisition FCS files using are exported and analyzed using FlowJo (TreeStar) or similar software according to the following gating strategy:

1. Create a dot plot FSC-H/FSC-A to identify single cells (G1).
2. Create on G1 a dot plot SSC-A/FSC-A to identify the cells-size population (G2).
3. Create on G2 a dot plot PI-A/FSC-A to select live cells (low PI-A) (G3). From now on each gate has to be set according to its respective FMO control.
4. Create on G3 a dot plot BUV737-A/BV421-A to evaluate the expression of CD38 and CD34 markers and create a gate on negative (G4) and on positive events (G5).
5. Create on G5 a dot plot SSC-A/BUV395-A to evaluate the expression of CD45 maker. Create a gate on CD45 negative (G6) and CD45 positive events (G7).
6. Create on G7 a dot plot SSC-A/BB515-A to evaluate the expression of CD33/CD66b markers. Create a gate on negative (G8; not-myeloid progenitors) and positive events (G9; myeloid progenitors).
7. Create on G9 a dot plot SSC-A/BV510-A to evaluate the expression of CD14 marker and cell granularity (SSC-A). Create a gate on CD14+ (G10), on high granularity events (G11) and on negative events (G12).
8. Create on G11 a dot plot BV786-A/BV650-A to evaluate the expression of CD10 and CD11c markers and create a gate on double positive events (G13) and on remaining events (G14).
9. Create on G12 a dot plot SSC-A/BV650-A to evaluate the expression of CD11c marker and create a gate on positive (G15) and negative events (G16).
10. Create on G16 a dot plot BUV737-A/BV421-A to evaluate the expression of CD38 and CD34 markers. Create a gate on CD34 positive events (G17; myeloid-committed progenitors). Check that all the events in this dot plot follow into the G17 gate.
11. Create on G8 a dot plot SSC-A/BV605-A to evaluate the expression of CD3 marker and create a gate on positive (G18) and negative events (G19).
12. Create on G18 a dot plot SSC-A/PE-Cy5-A to evaluate the expression of CD56 and create a gate on positive (G20) and negative events (G21).

13. Create on G19 a dot plot SSC-A/APC-R700-A to evaluate the expression of CD19 marker and create a gate on positive (G22) and negative (G23) events.

14. Create on G22 a dot plot BV785-A/BV421-A to evaluate the expression of CD10 and CD34 markers and create a gate on double positive (G24; Pro-B), and CD34+ only (G25) events. Check that all the events in this dot plot follow into G24 or G25 gates.

15. Create on G23 a dot plot SSC-A/PE-Cy5-A to evaluate the expression of CD56 marker and create a gate on positive (G26) and negative (G27) events.

16. Create on G27 a dot plot BUV737-A/BV421-A to evaluate the expression of CD38 and CD34 markers and create a gate on CD34+ (G28, LIN− progenitors). Check that all the events in this dot plot follow into the G28 gate.

17. Create on merged G17+G28 a dot plot BV785-A/CD421-A to evaluate the expression of CD38 and CD34 markers. All the events should be CD34+. Create a gate on CD38+ (G29) and CD38− (G30) events.

18. Create on G30 a dot plot APC-A/APC-Cy7-A to evaluate the expression of CD90 and CD45RA markers and create a gate on CD90+only (G31; HSC), double negative (G32; MPP) and CD45RA+ (G33; MLP) events.

19. Create on G29 a dot plot SSC-A/PerCP-Cy5.5-A to evaluate the expression of CD7 marker and create a gate on CD7+ (G34; ETP) and CD7− (G35) events.

20. Create on G35 a dot plot BV785-A/APC-Cy7-A to evaluate the expression of CD10 and CD45RA markers and create a gate on CD10+ (G36; Pre-B/NK) and CD10− (G37) events.

21. Create on G37 a dot plot PE-A/APC-Cy7-A to evaluate the expression of CD135 and CD45RA markers and create a gate on CD135+ only (G38; CMP), double positive (G39; GMP) and double negative (G40; MEP) events.

22. Create a table with the percentages of all gates on their paternal gate and calculate the overall percentages on the total CD34+ cells (gate G5).

23. Graphical output is generated with Prism 6.0c (GraphPad software) setting a layout with a "Part of Whole" ring plot for all cell populations, percentages on total CD34+ cells.

Example 2

Characterization BM and PB Samples Isolated from Healthy Donors

To test the efficiency of a method according to the present invention for successfully identifying blood hematopoietic cell subtypes and for reproducibly determining their relative frequency in human BM and PB, 5 BM and 14 PB WB samples from 19 adult (Ad) healthy donors (HD) were analysed (FIGS. 1B-E and 7, and Tables 3-4).

TABLE 3

Frequencies of bone marrow and peripheral blood hematopoietic cell subtypes in healthy donors as a percentage of total CD45+ cells. Average percentages ± Standard Deviations of hematopoietic cell frequencies on total CD45− (erythroblasts) and on total CD45+ (leukocytes) cells. (* = p <0.05;  = p<0.01; * = p <0.001; Mann-Whitney Test).

|  | HD BM n = 5 |  | HD PB n = 14 |
|---|---|---|---|
| % ON CD45− |  |  |  |
| ERYTHROBLAST | 84.1 ± 8.3 | *** | 0.14 ± 0.18 |
| % ON CD45+ |  |  |  |
| MYELOID | 71.5 ± 11.9 | ns | 60.4 ± 12.4 |
| iPMN | 46.6 ± 11.3 | *** | 2.9 ± 1.3 |
| PMN | 20.6 ± 2.5 | *** | 51 ± 11.4 |

TABLE 3-continued

Frequencies of bone marrow and peripheral blood hematopoietic cell subtypes in healthy donors as a percentage of total CD45+ cells. Average percentages ± Standard Deviations of hematopoietic cell frequencies on total CD45− (erythroblasts) and on total CD45+ (leukocytes) cells. (* = p <0.05;  = p<0.01; * = p <0.001; Mann-Whitney Test).

|  | HD BM n = 5 |  | HD PB n = 14 |
|---|---|---|---|
| MONOCYTE | 3.2 ± 1 | * | 5.5 ± 1.8 |
| DC | 0.3 ± 0.1 | ns | 0.4 ± 0.2 |
| MYELOBLAST | 0.7 ± 0.3 | ns | 0.7 ± 0.3 |
| LYMPHOID | 25.3 ± 10.7 | * | 38.8 ± 12.2 |
| T CELL | 12.9 ± 4.4 | ** | 28.9 ± 10 |
| NKt CELL | 0.5 ± 0.3 | ** | 1.7 ± 0.9 |
| NK CELL | 2.4 ± 1.8 | ns | 3.8 ± 1.7 |
| CD19 +CELL | 9.6 ± 6 | ns | 4.4 ± 2.1 |
| B CELL | 4.7 ± 3.2 | ns | 4.3 ± 2.1 |
| Pre-B | 4.2 ± 2.7 | *** | 0.1 ± 0.1 |
| Pro-B | 0.7 ± 0.5 | **** | 0 |
| IMMATURE CELL | 2.2 ± 0.9 | * | 0.19 ± 0.07 |
| PRO-LYMPHOCYTE | 0.4 ± 0.2 | * | 0.14 ± 0.06 |
| PRO-ERYTHROBLAST | 0.5 ± 0.2 | *** | 0.003 ± 0.004 |
| HSPC | 1.3 ± 0.6 | *** | 0.044 ± 0.013 |

TABLE 4

Frequencies of bone marrow and peripheral blood hematopoietic subtypes in healthy donors by relative compartment. Average percentages ± standard deviations of hematopoietic subtypes in the major hematopoietic compartments. (* = p <0.05;  = p <0.01; * = p <0.001; Mann-Whitney Test).

|  | HD BM n = 5 |  | HD PB n = 14 |
|---|---|---|---|
| % ON MYELOID (CD45+CD33+CD66b+Lin+) |  |  |  |
| iPMN | 64.6 ± 6.2 | *** | 4.7 ± 1.8 |
| PMN | 29.3 ± 4.6 | *** | 84.3 ± 4.6 |
| MONOCYTE | 4.6 ± 1.4 | ** | 9.2 ± 2.8 |
| DC | 0.4 ± 0.3 | ns | 0.7 ± 0.3 |
| MYELOBLAST | 1.1 ± 0.4 | ns | 1.1 ± 0.7 |
| % ON LYMPHOID (CD45+CD33−CD66b−Lin+) |  |  |  |
| T CELL | 55.2 ± 16.4 | * | 74.2 ± 6.1 |
| NKt CELL | 2.3 ± 1.4 | ns | 4.6 ± 2.6 |
| NK CELL | 8.3 ± 4.1 | ns | 10.1 ± 4.4 |
| CD19+ CELL | 34.2 ± 14.6 | 11 ± 3.7 |  |
| B CELL | 16.2 ± 7.2 | ns | 10.8 ± 3.6 |
| Pre-B | 14.9 ± 7.8 | *** | 0.2 ± 0.2 |
| Pro-B | 3.1 ± 1.7 | **** | 0 |
| % ON CD19+ CELLS (CD45+CD33−CD66b−CD19+) |  |  |  |
| B CELL | 46.5 ± 8.4 | *** | 98 ± 1.1 |
| Pre-B | 42.2 ± 6.6 | *** | 2 ± 1.4 |
| Pro-B | 11.3 ± 10.4 | *** | 0 |
| % ON IMMATURE CELL (CD45+Lin−) |  |  |  |
| PRO-LYMPHOCYTE | 17.7 ± 9.8 | *** | 72.6 ± 12.4 |
| PRO-ERYTHROBLAST | 20.6 ± 6 | *** | 1.7 ± 2 |
| HSPC | 61.7 ± 10.9 | *** | 25.7 ± 12.7 |

The different cellular composition between BM and PB was evident starting from the evaluation of the CD45 marker. In the BM sample the CD45+ fraction contained cell subtypes with more diversified levels of CD45 expression as compared to the PB sample where the vast majority of the cells is CD45$^{high}$ due to their mature differentiation state. In the CD45− fraction of the BM a substantial number of CD71+ erythroblasts were identified (on average 84.1% of CD45− cells), which conversely were almost undetectable in the PB samples (on average 0.03% of CD45− cells; p<0.001 Mann-Whitney test). The CD45+ cells were divided according to the expression of CD33 and CD66b markers in myeloid (CD45+/CD33+/CD66b+) and non-myeloid (CD45+/CD33−/CD66b−) populations.

Within the myeloid compartment we distinguished monocytes (SSC-A$^{mid}$/CD14+) and granulocytes (SSC-A$^{high}$/CD14−). The granulocytes were then further dissected into two populations with different degree of maturation: mature PMN (CD10+/CD11c+) and Immature PMN (iPMN; CD10− and/or CD11c−). In the SSC-A$^{low}$/CD14− fraction DC were identified by the expression of CD11c while the negative events were divided into myeloid precursors (Myeloblast; CD34−) and myeloid-committed progenitors (CD34+) (Table 1). As expected, a higher relative contribution of iPMN in the BM with respect to PB samples was observed (on average on CD45+ cells, iPMN: 46.6% in BM vs 2.9% in PB p<0.001; Mann-Whitney test). However, no any differences in the relative frequencies of myeloblasts in the myeloid compartment were observed (FIG. 7B and Table 3-4).

Within the non-myeloid compartment T-cells (CD3+/CD56−), NKT cells (CD3+/CD56+), B-cells (mature: CD19+/CD10−/CD34−; Pre-B cells: CD19+/CD10+/CD34− and Pro-B cells: CD19+/CD10+/CD34+), NK cells (CD3−/CD19−/CD56+) and LIN-CD34+ cells were discriminated (Table 1). It was observed that mature T-cells and NKT cells were significantly more abundant in PB samples (on average on total CD45+ cells, T 28.9% and NKT cells 1.7%) than in BM samples (on average on total CD45+ cells, T-cells 12.9% and NKT cells 0.5%) (BM vs. PB T-cells: p<0.1; BM vs. PB NKT cells: p<0.01; Mann-Whitney test; Table 3-4). Moreover, in accordance with what was expected from the biology of B cell differentiation, specifically and only immature B-cells could be identified in the BM samples (on average on lymphoid cells, Pre-B 14.9% and Pro-B 3.1%; FIG. 7C-D and Table 3-4).

After exclusion of LIN+ cells on the basis of CD33, CD66b, CD14, CD11c, CD3, CD19 and CD56 markers, LIN− compartment was evaluated. Among CD45+/LIN−/CD34− cells we distinguished pro-erythroblasts (CD71+), immature platelets (CD41/61+) and in the CD71− and CD41/61− compartment two lymphoid-committed subsets were identified (CD10+ or CD7+) (Table 1). As expected, a higher frequency of immature LIN− cells in BM with respect to PB samples were observed (on average on CD45+ cells 2.2% in BM vs. 0.19% in PB; p<0.05 Mann-Whitney test; FIG. 7A and Table 3-4). Interestingly, pro-erythroblasts were found only in the BM samples (on average on CD45+LIN− cells: 20.6% in BM vs. 1.7% in PB; p<0.001 Mann-Whitney test; FIG. 7E and Table 3-4).

The CD45+/LIN−/CD34+ cells and CD45+/CD33+CD66b+/CD34+ populations were then pooled in order to analyse the entire HSPC compartment. The most primitive subsets (CD34+/CD38−) as HSC (CD90+/CD45RA−), MPP (CD90−/CD45RA−) and MLP (CD45RA+) were identified. Committed progenitors (CD34+/CD38+) could be divided into ETP (CD7+), Pre-B/NK (CD7−/CD10), CMP (CD7−/CD10−/CD135+/CD45RA−), GMP (CD7−/CD10−/CD135+/CD45RA+) and MEP (CD7−/CD10−/CD135−/CD45RA−) (Table 1). Importantly, through using the protocol of Example 1 circulating HSPC in PB could be detected (on average 25.7% of CD45+/LIN− cells, Table 3-4) although, as expected, at lower level with respect to their BM counterpart (on average 61.7% of CD45+/LIN− cells; BM vs. PB=p<0.001 Mann-Whitney test, Table 3-4).

The complete list of BM and PB cell population frequencies and comparative statistical test results are reported in Tables 3-4.

In summary, by using the protocol of according to the present invention it was possible to univocally classify 23 different hematopoietic cell subtypes covering on average 99.8% of the subtypes present in the BM samples and 99.6% of the subtypes present in the PB samples.

Example 3

Validation by Morphological Assays

Figure 2B:
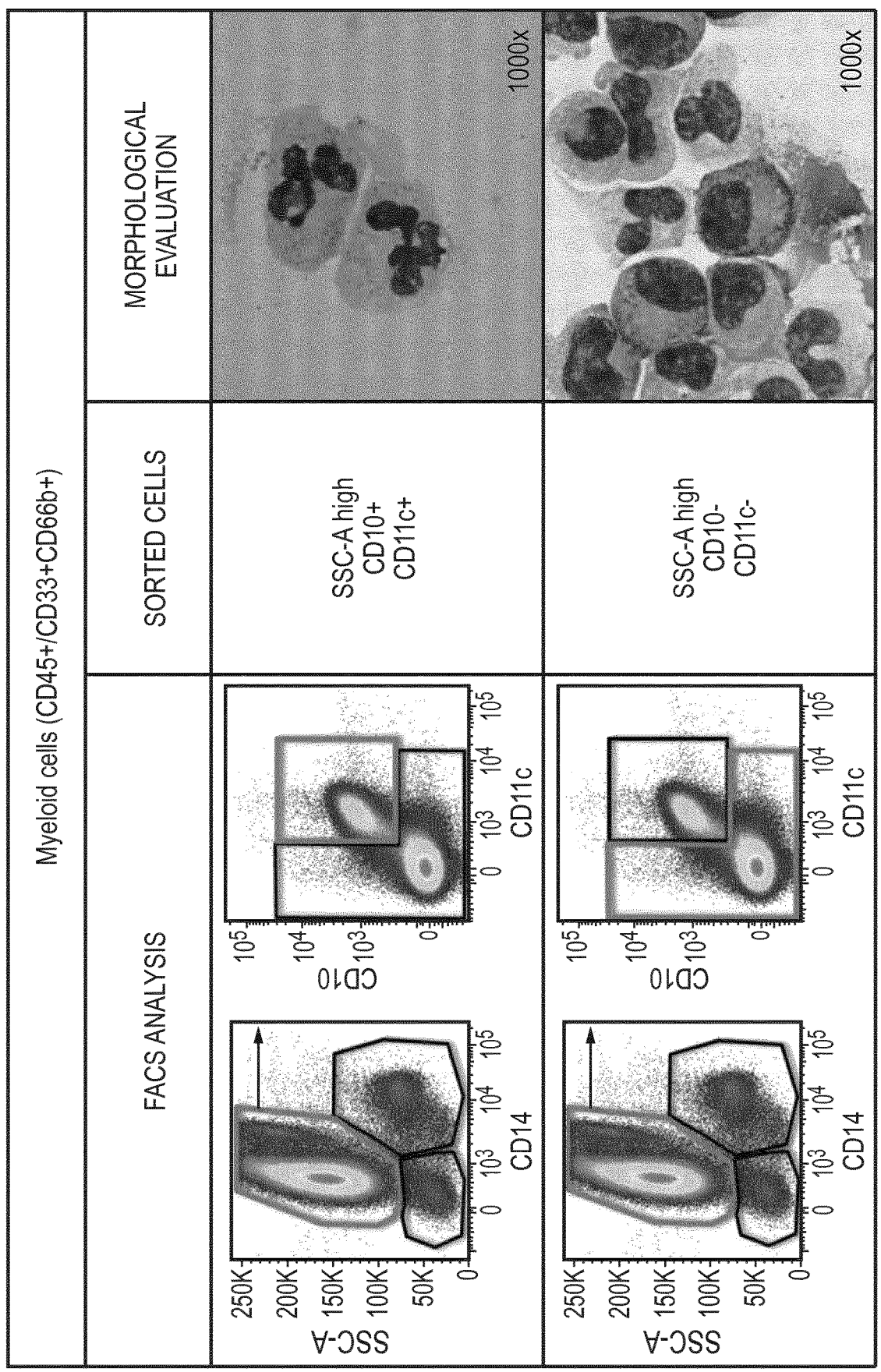
Figure 2B:
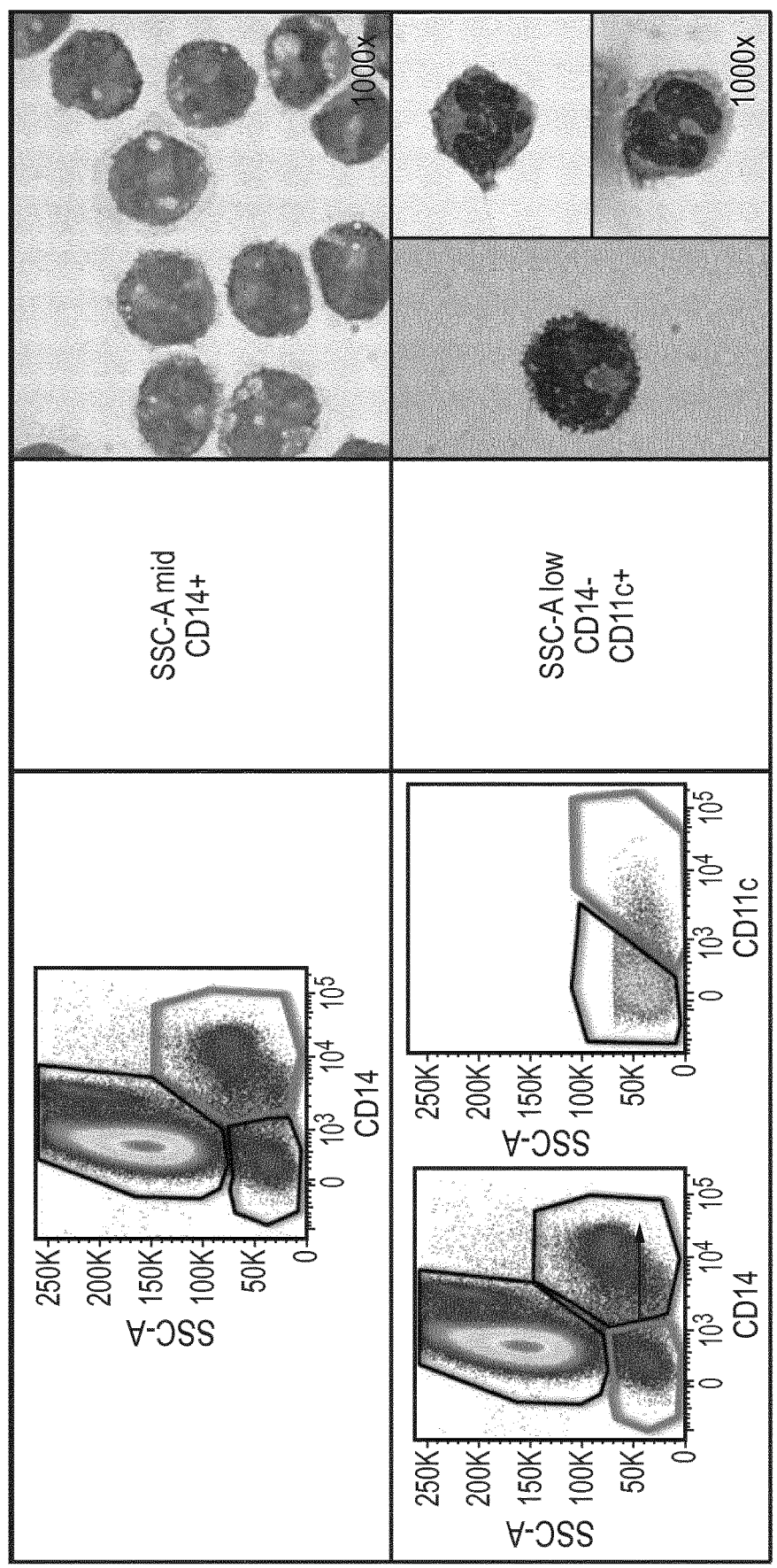
Figure 2C:
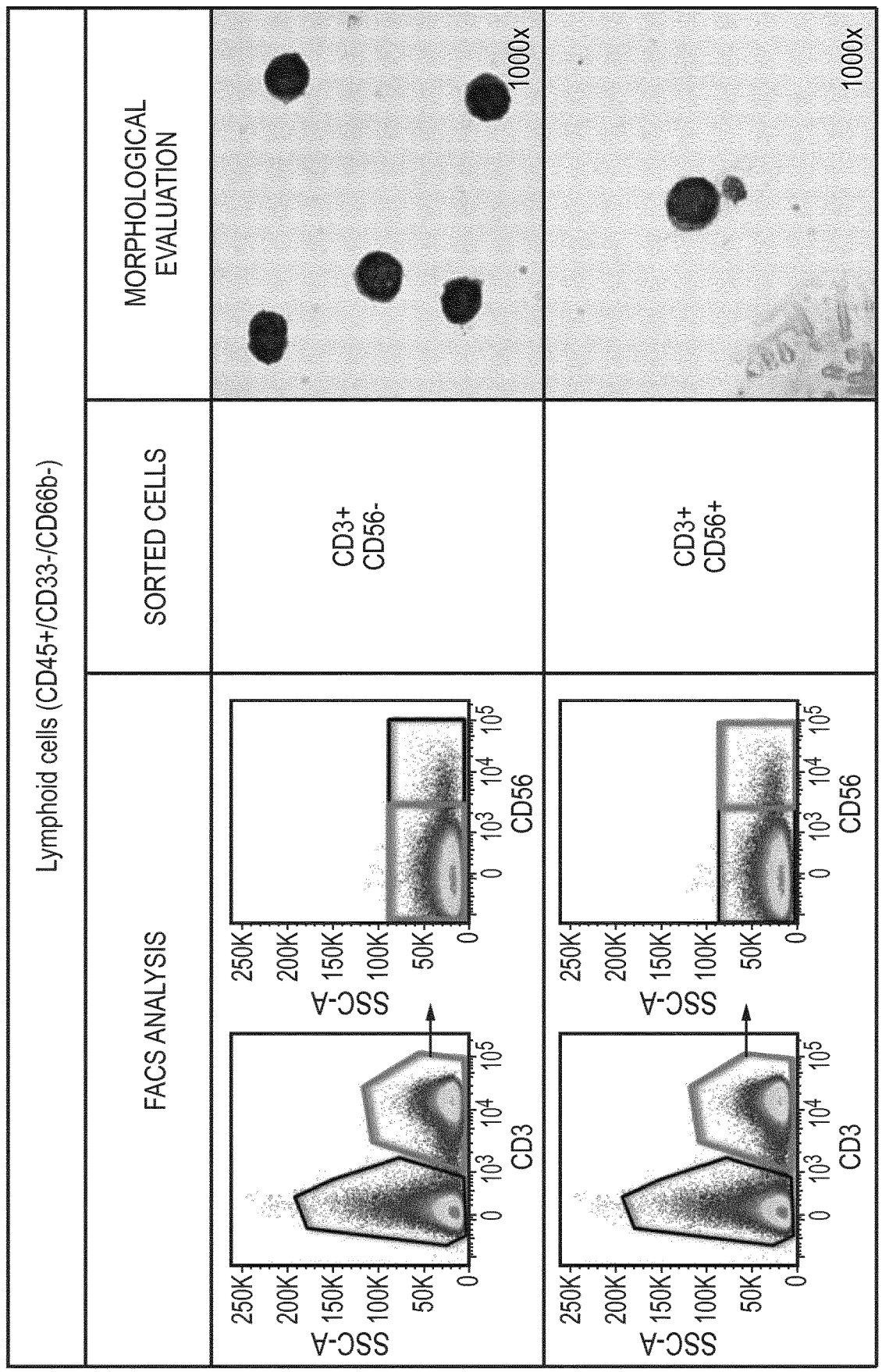
Figure 2C:
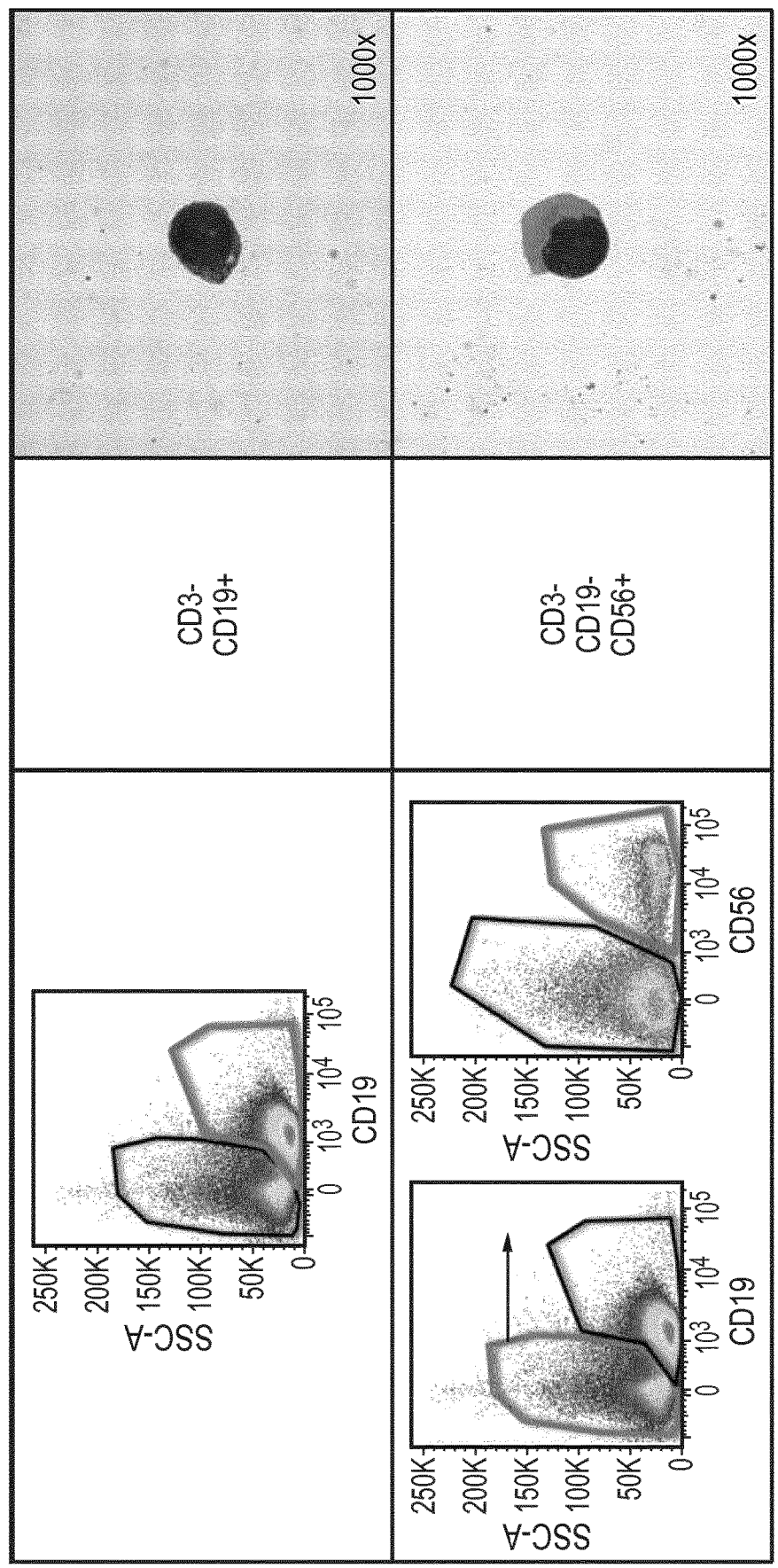
Figure 2D:
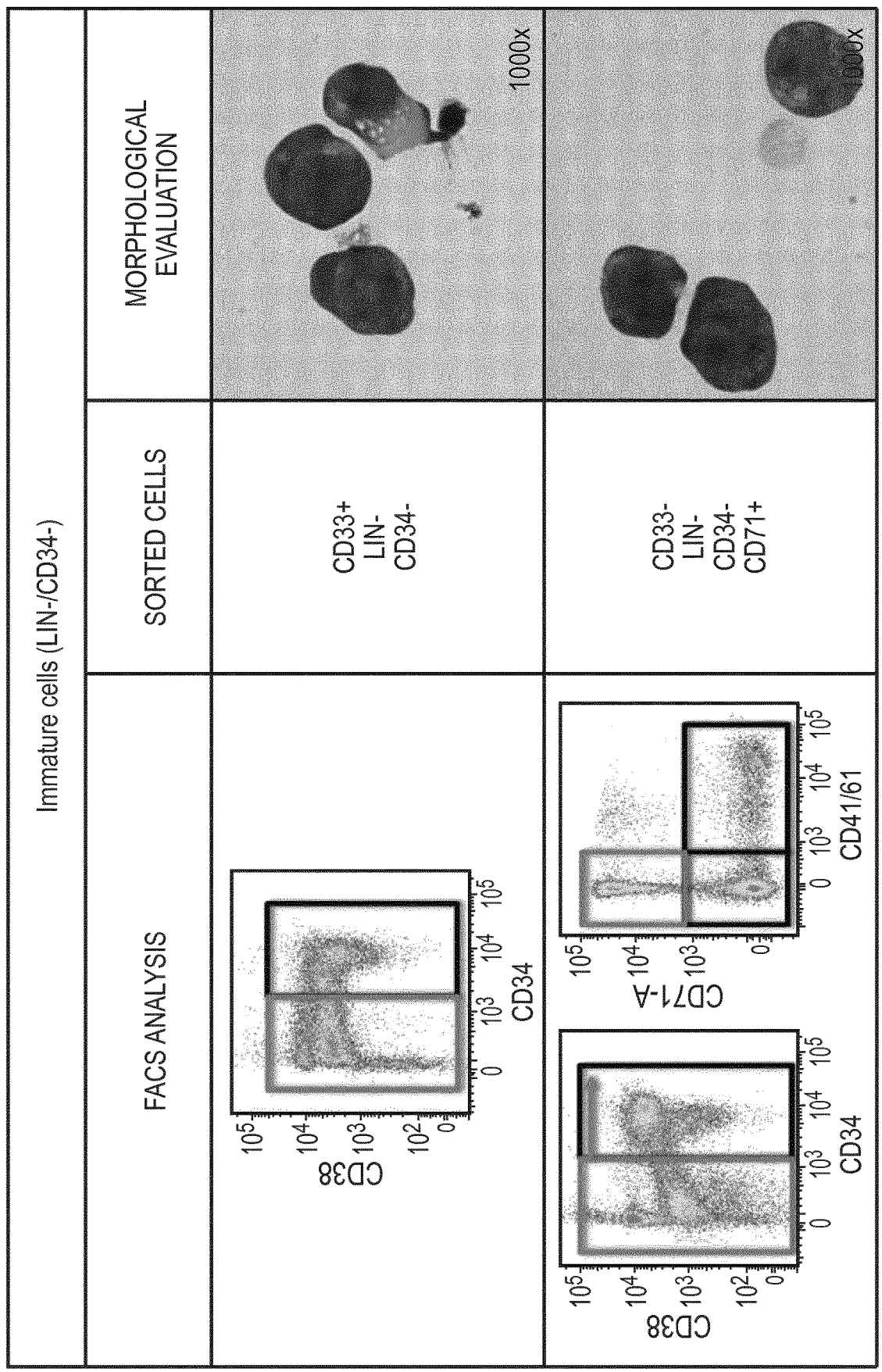
Figure 2D:
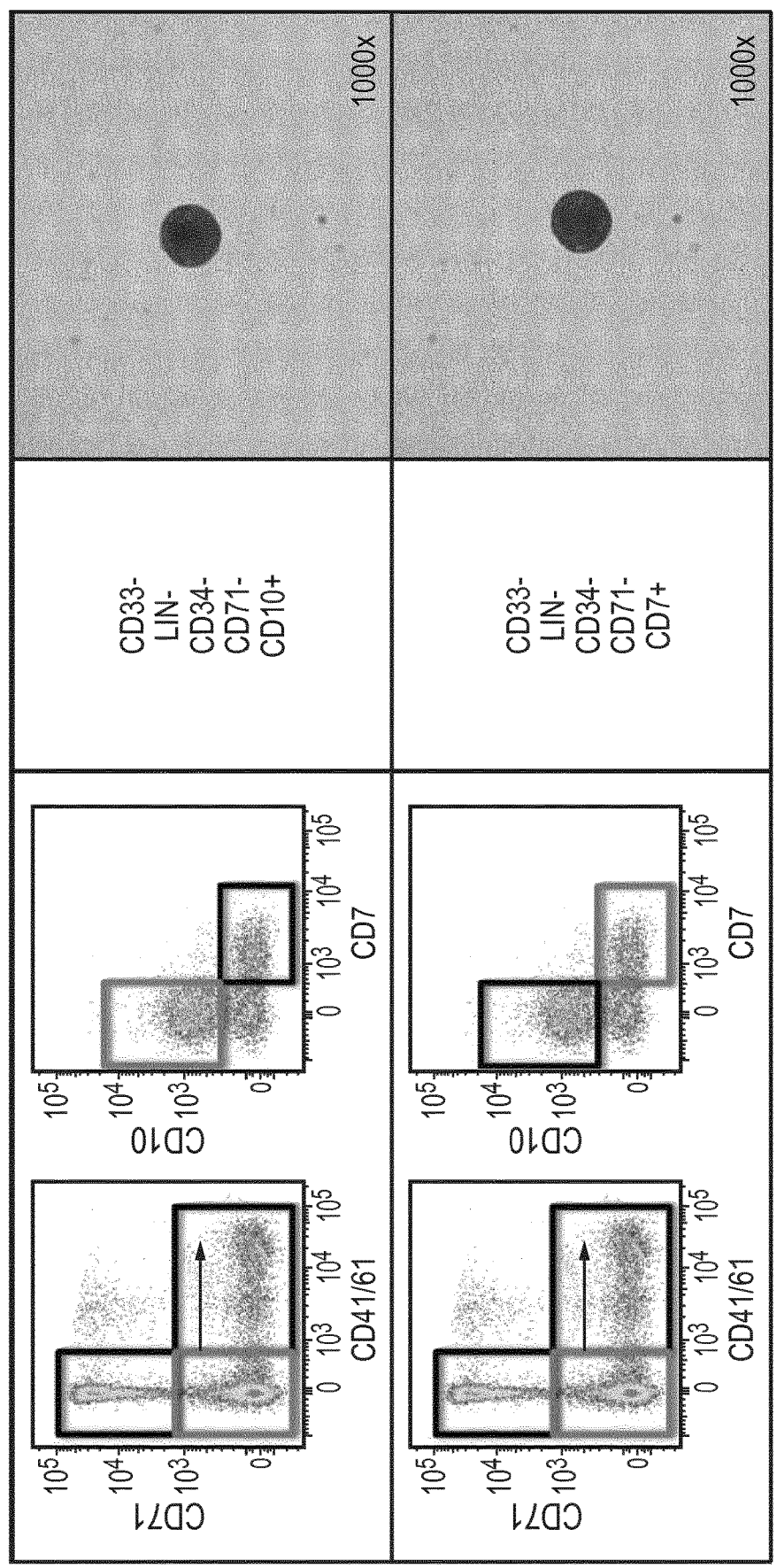

To test whether the protocol according to the present invention was able to properly identify each hematopoietic cell subtype, five independent FACS sorting experiments were performed. The same gating strategy set out in Example 1 was used to isolate different putative cell subpopulations from BM, since BM is a source with the most diverse composition of hematopoietic cell subtypes. Then the morphology of sorted cells was analysed in blind tests to assess whether it was matching their original categorization (FIG. 2B-D). The list of markers used for the five FACS sorting is reported in FIG. 2A and the details of cell isolation and morphological evaluation protocol are described in the material and methods section.

Importantly, morphological evaluation of all sorted myeloid and lymphoid lineages confirmed that the results of the phenotypic characterization performed through using the protocol according to the present invention were correct—see FIG. 2B-C. Notably, the morphological validation of the protocol allowed for the characterization of cell subtypes that are poorly described at present.

Indeed, two additional blood cell subpopulations defined as by the phenotypes CD45+/CD33−CD66b−/LIN−/CD34−/CD71−/CD10+ and CD45+/CD33−CD66b−/LIN−/CD34−/CD71−/CD7+ were identified. Originally it was speculated that these subsets belonged to the lymphoid compartment due to the presence of CD10 and CD7 markers on their surface. However, upon morphological evaluation it was actually confirmed that these cells displayed a lymphoid-like appearance being small round cells with a thin rim of cytoplasm (FIG. 2D).

Notably, use of a protocol according to the present invention has revealed that, despite having a unequivocal phenotypic definition (Table 1), the iPMN compartment seems actually composed by a morphologically mixed population of immature granulocytes at different stages of differentiation (FIG. 2B).

Example 4

Comparison of the Relative Frequency of Hematopoietic Cell Subtypes Present in Whole Blood Samples from Paediatric Healthy Donors and Patients with PID Having validated the capability of the protocol of Example 1 to properly identify the different cell subpopulations in normal BM and PB from HD, the efficacy of the protocol for detecting known aberrant hematopoietic cell compositions in patients with haematological disorders was evaluated. To this aim, the protocol of Example 1 was performed on samples from 28 individuals affected by different diseases, including immunodeficiencies (WAS, ADA-SCID, CGD), MLD and hematological tumours (ALL, AML and MM)—see Tables 5 and 6.

TABLE 5

Clinical features of the WAS, ADA-SCID, CGD and MLD patients.

| PATIENT | AGE AT ONSET (months) | SEX | AGE AT ANALYSES (years) |
|---|---|---|---|
| WAS Pt1 | 24 | M | 34 |
| WAS Pt2 | 7 | M | 14 |
| WAS Pt3 | 12 | M | 3.5 |

TABLE 5-continued

Clinical features of the WAS, ADA-SCID, CGD and MLD patients.

| PATIENT | AGE AT ONSET (months) | SEX | AGE AT ANALYSES (years) |
|---|---|---|---|
| WAS Pt4 | 2 days | M | 2.5 |
| WAS Pt5 | 1 | M | 25 |
| WAS Pt6 | 95 | M | 27 |
| ADA-SCID Pt1 | 1.75 | M | 5 |
| ADA-SCID Pt2 | 2 | M | 0.9 |
| ADA-SCID Pt3 | 1 | F | 0.7 |
| ADA-SCID Pt4 | 3 | M | 9 |
| ADA-SCID Pt5 | 3 | F | 5 |
| ADA-SCID Pt6 | 15 days | M | 0.7 |
| ADA-SCID Pt7 | 2 | M | 0.7 |
| MLD Pt1 | Pre-symptomatic | M | 0.6 |
| MLD Pt2 | Pre-symptomatic | M | 0.6 |
| MLD Pt3 | Pre-symptomatic | F | 0.9 |
| MLD Pt4 | Pre-symptomatic | F | 1 |
| MLD Pt5 | Pre-symptomatic | M | 1 |
| MLD Pt6 | Pre-symptomatic | M | 0.6 |
| CGD | 132 | M | 33 |

TABLE 6

Clinical features of the leukemic patients.

| PATIENT | DIAGNOSIS and CLINICS | % BLASTS MORPHOLOGY | % BLASTS CYTOMETRY | SEX | AGE AT ANALYSES (years) |
|---|---|---|---|---|---|
| AML-1 | AML at diagnosis | 98 | 93 | M | 36 |
| AML-2 | AML at relapse | 81 | 66 | M | 48 |
| AML-3 | AML at diagnosis | 58 | 53 | F | 22 |
| AML-4 | AML at diagnosis | 72 | 65 | M | 70 |
| AML-5 | AML post-chemotherapy | 16 | 9.9 | M | 69 |
| AML-6 | AML post-chemotherapy | N/A | 6.2 | M | 69 |
| ALL | ALL-B post-BMT and post-chemotherapy | N/A | 10 | M | 24 |
| MM | MM at diagnosis | 41 | 30 | M | 84 |

Given that the age of an individual physiologically affects the composition of the hematopoietic population, BM samples from five pediatric (Ped) HD in addition to our cohort of adult HD were analysed in order to further assess the reproducibility of our technology and to obtain age-matched reference datasets for comparing HD vs. patients' samples. Although a similar cellular distribution among the different leukocyte compartments in Ped HD and Ad HD was observed (FIGS. 3B, and 8A-B), as expected differences were observed for the lymphoid compartment where, relative to the Ad HD, Ped HD had a higher frequency of mature (50.5% vs 39% CD19+ cells on total lymphocytes) and immature B cells (28.5% vs 17.4% Pre-B cells on CD19+ lymphocytes) (FIG. 8D-E; Tables 7 and 8).

TABLE 7

Relative frequencies of bone marrow subpopulations in healthy donors and patients as a percentage of total CD45+ cells. Average percentage ± standard deviations for BM hematopoietic cells in adult and pediatric healthy donors and in MLD, WAS and ADA-SCID and CGD affected individuals.

| | AD HD n = 5 | PED HD n = 5 | MLD n = 6 | vs PED HD | WAS n = 6 | vs HD | ADA-SCID n = 7 | vs PED HD | CGD n = 1 |
|---|---|---|---|---|---|---|---|---|---|
| % ON CD45− | | | | | | | | | |
| ERYTHROBLAST | 84.1 ± 8.3 | 85.6 ± 2.4 | 55.3 ± 14.2 | ** | 45.7 ± 36.4 | * | 62.6 ± 22 | * | 17.7 |
| % ON CD45+ | | | | | | | | | |
| MYELOID | 71.5 ± 11.9 | 70.3 ± 8 | 58.1 ± 7.9 | ns | 79.8 ± 7.9 | ns | 66 ± 12.2 | ns | 86.4 |
| iPMN | 46.6 ± 11.3 | 43.4 ± 10.1 | 39.6 ± 7.2 | ns | 33.3 ± 10.6 | * | 36.9 ± 11.4 | ns | 52.2 |
| PMN | 20.6 ± 2.5 | 22.2 ± 3.2 | 11.9 ± 2.7 | ** | 38.1 ± 14.1 | * | 22.8 ± 9.9 | ns | 32.4 |
| MONOCYTE | 3.2 ± 1 | 3.4 ± 0.8 | 5 ± 1.9 | ns | 7.3 ± 2.3 | *** | 5.1 ± 1.8 | ns | 1.3 |
| DC | 0.3 ± 0.1 | 0.2 ± 0.1 | 0.3 ± 0.1 | ns | 0.2 ± 0.2 | ns | 0.3 ± 0.1 | ns | 0 |
| MYELOBLAST | 0.7 ± 0.3 | 1 ± 0.3 | 1.2 ± 0.5 | ns | 0.8 ± 0.4 | ns | 0.9 ± 0.5 | ns | 0.4 |
| LYMPHOID | 25.3 ± 10.7 | 26.7 ± 7.9 | 36.9 ± 8.6 | ns | 18.2 ± 7.3 | ns | 27.8 ± 9.4 | ns | 13.1 |
| T CELL | 12.9 ± 4.4 | 11.7 ± 5.8 | 15 ± 7.1 | ns | 9.4 ± 4.7 | ns | 6.3 ± 5 | ns | 8.1 |

TABLE 7-continued

Relative frequencies of bone marrow subpopulations in healthy donors and patients as a percentage of total CD45+ cells. Average percentage ± standard deviations for BM hematopoietic cells in adult and pediatric healthy donors and in MLD, WAS and ADA-SCID and CGD affected individuals.

|  | AD HD n = 5 | PED HD n = 5 | MLD n = 6 | vs PED HD | WAS n = 6 | vs HD | ADA-SCID n = 7 | vs PED HD | CGD n = 1 |
|---|---|---|---|---|---|---|---|---|---|
| NKt CELL | 0.5 ± 0.3 | 0.3 ± 0.2 | 0.1 | ** | 0.3 ± 0.4 | ns | 0.2 ± 0.3 | ns | 0.3 |
| NK CELL | 2.4 ± 1.8 | 1.3 ± 0.7 | 1.6 ± 0.7 | ns | 3.7 ± 3.3 | ns | 2 ± 1.6 | ns | 0.6 |
| CD19+ CELL | 9.6 ± 6 | 13.4 ± 4.5 | 20.2 ± 5.2 | ns | 4.7 ± 2.3 | * | 19.4 ± 12.2 | ns | 4.1 |
| B CELL | 4.7 ± 3.2 | 4.7 ± 1.4 | 6.4 ± 2.3 | ns | 3.1 ± 1.5 | ns | 1.5 ± 1.5 | * | 4.0 |
| PRE-B | 4.2 ± 2.7 | 7.6 ± 3.7 | 12 ± 5.5 | ns | 1.3 ± 0.9 | ** | 15.2 ± 9.3 | ns | 0.0 |
| PRO-B | 0.7 ± 0.5 | 1.1 ± 0.6 | 1.7 ± 0.8 | ns | 0.3 ± 0.2 | * | 2.6 ± 2.4 | ns | 0.0 |
| IMMATURE CELL | 2.2 ± 0.9 | 2.1 ± 0.3 | 3.9 ± 1.4 | ns | 1.2 ± 0.7 | * | 4.1 ± 3.1 | ns | 0.4 |
| PRO-LYMPHOCYTE | 0.4 ± 0.2 | 0.3 ± 0.1 | 1 ± 0.7 | * | 0.5 ± 0.4 | ns | 1.1 ± 1.6 | ns | 0.0 |
| PRO-ERYTHROBLAST | 0.5 ± 0.2 | 0.7 ± 0.2 | 0.4 ± 0.1 | ns | 0.1 ± 0.1 | *** | 0.3 ± 0.2 | * | 0.3 |
| HSPC | 1.3 ± 0.6 | 1.2 ± 0.2 | 2.6 ± 1.0 | ** | 0.6 ± 0.4 | ** | 2.7 ± 2.1 | ns | 0.1 |
| CD38− | 0.11 ± 0.17 | 0.08 ± 0.03 | 0.15 ± 0.05 | ns | 0.03 ± 0.03 | ns | 0.08 ± 0.07 | ns | 0.01 |
| CD38+ | 1.20 ± 0.44 | 1.05 ± 0.17 | 2.41 ± 0.92 | ** | 0.54 ± 0.32 | ** | 2.58 ± 2.08 | ns | 0.11 |

TABLE 8

Relative frequencies of bone marrow haematopoietic cell subtypes in healthy donors and patients by specific compartment. Average percentages ± standard deviations of hematopoietic subpopulations in the major hematopoietic compartments for all groups of individuals analyzed.

|  | AD HD n = 5 | PED HD n = 5 | MLD n = 6 | vs PED HD | WAS n = 6 | vs HD | ADA-SCID n = 7 | vs PED HD | CGD n = 1 |
|---|---|---|---|---|---|---|---|---|---|
| % ON MYELOID (CD45+CD33+CD66b+LIN+) | | | | | | | | | |
| IPMN | 64.6 ± 6.2 | 61.1 ± 9.2 | 67.8 ± 5 | ns | 42.3 ± 14.4 | ** | 55.3 ± 12.4 | ns | 60.4 |
| PMN | 29.3 ± 4.5 | 32.1 ± 7.3 | 20.5 ± 3.5 | ** | 47.1 ± 15.4 | ns | 34.4 ± 12 | ns | 37.5 |
| MONOCYTE | 4.5 ± 1.4 | 4.9 ± 1.5 | 8.9 ± 4.1 | * | 9.1 ± 2.7 | ** | 8.2 ± 4.1 | ns | 1.6 |
| DC | 0.4 ± 0.3 | 0.4 ± .02 | 0.6 ± 0.2 | ns | 0.3 ± 0.2 | ns | 0.5 ± 0.3 | ns | 0 |
| MYELOBLAST | 1.1 ± 0.4 | 1.5 ± 0.4 | 2.2 ± 1.2 | ns | 1.1 ± 0.6 | ns | 1.5 ± 1.1 | ns | 0.5 |
| % ON LYMPHOID (CD45+CD33+CD66b+LIn+) | | | | | | | | | |
| T CELL | 55.2 ± 16.4 | 43.3 ± 12.4 | 39.7 ± 10.8 | ns | 52.6 ± 17 | ns | 27.2 ± 25.6 | ns | 61.9 |
| NKt CELL | 2.3 ± 1.4 | 1.2 ± 0.4 | 0.3 ± 0.1 | ** | 1.5 ± 1.2 | ns | 0.9 ± 1.3 | ns | 2.7 |
| NK CELL | 8.3 ± 4.1 | 5 ± 2 | 4.5 ± 2 | ns | 20 ± 15.5 | ** | 6.9 ± 4.8 | ns | 4.5 |
| CD19 + CELL | 34.2 ± 14.6 | 50.5 ± 14.5 | 55.6 ± 11.9 | ns | 25.5 ± 7.7 | * | 65.1 ± 29 | ns | 31 |
| B CELL | 16.2 ± 7.2 | 18.1 ± 5.5 | 17.3 ± 3.7 | ns | 17.1 ± 6.4 | ns | 4.9 ± 3.3 | ** | 30.9 |
| PRE-B | 14.9 ± 7.8 | 28.5 ± 14 | 33.4 ± 14.7 | ns | 7.2 ± 4.3 | ** | 51.3 ± 22.1 | ns | 0.1 |
| PRO-B | 3.1 ± 17 | 3.9 ± 2 | 5 ± 2.4 | ns | 1.6 ± 1.3 | * | 8.9 ± 7.2 | ns | 0.0 |
| % ON CD19+CELLS (CD45+CD33−CD66b+CD19+) | | | | | | | | | |
| B CELL | 46.5 ± 8.4 | 38.5 ± 17 | 33.2 ± 12.5 | ns | 67.8 ± 21.9 | * | 8.1 ± 4 | ** | 99.8 |
| PRE-B | 42.2 ± 6.6 | 53.9 ± 15 | 57.8 ± 12.8 | ns | 26.2 ± 16.9 | * | 79.4 ± 3.5 | ** | 0.2 |
| PRO-B | 11.3 ± 10.4 | 7.6 ± 2.2 | 9 ± 4.5 | ns | 6.1 ± 5.3 | ns | 12.6 ± 6.6 | ns | 0.0 |
| % ON IMMATURE CELL (CD45+Lln−) | | | | | | | | | |
| PRO-LYMPHOCYTE | 17.7 ± 9.8 | 15.4 ± 5.4 | 23.4 ± 10.9 | ns | 37.5 ± 13.7 | ** | 26.5 ± 19.8 | ns | 4.1 |
| PRO-ERYTHROBLAST | 20.6 ± 6 | 30.9 ± 7.2 | 9.8 ± 3.9 | ** | 17.1 ± 17.8 | ns | 8.4 ± 3 | ** | 64.8 |
| HSPC | 61.7 ± 10.9 | 53.7 ± 6.2 | 66.8 ± 10.8 | ns | 45.5 ± 13.1 | ns | 65.1 ± 18.6 | ns | 31.1 |
| % ON HSPC (CD45+Lln−CD34+) | | | | | | | | | |
| CD38− | 5.4 ± 6.5 | 6.9 ± 2.3 | 5.9 ± 2 | ns | 4.4 ± 1.7 | ns | 3.5 ± 3.1 | ns | 6.8 |
| HSC | 4 ± 4.4 | 2.7 ± 0.9 | 1.3 ± 0.6 | * | 1.8 ± 0.6 | ns | 0.7 ± 0.6 | ** | 3.6 |
| MPP | 1.7 ± 2.2 | 3.1 ± 2.5 | 3.5 ± 1.3 | ns | 1.4 ± 1.1 | ns | 1.7 ± 1.6 | ns | 2.8 |
| MLP | 0.7 ± 0.7 | 1.1 ± 0.8 | 1.2 ± 0.7 | ns | 1.1 ± 1 | ns | 1 ± 1.3 | ns | 0.4 |
| CD38+ | 91.8 ± 6.1 | 90.3 ± 1.9 | 92.8 ± 3 | ns | 93.7 ± 3.5 | ns | 95.9 ± 2.6 | ns | 93 |
| ETP | 0.6 ± 1 | 0.2 ± 0.1 | 1.3 ± 1.7 | ns | 0.2 ± 0.3 | ns | 0.6 ± 1 | ns | 0.1 |
| PRE-B/NK | 18.6 ± 6.2 | 25.7 ± 11.7 | 46.7 ± 11.6 | * | 27 ± 14 | ns | 44.6 ± 12.4 | * | 3.1 |
| CMP | 27.7 ± 7.5 | 23.4 ± 11.3 | 10.7 ± 3 | * | 21.1 ± 8.3 | ns | 16.6 ± 6.5 | ns | 60.6 |
| GMP | 29.3 ± 10.3 | 28.3 ± 5 | 27.9 ± 10.3 | ns | 30.5 ± 7.1 | ns | 29.1 ± 7.1 | ns | 23.5 |
| MEP | 15.6 ± 8.3 | 12.7 ± 5.5 | 6.3 ± 3.9 | * | 14.8 ± 9.9 | ns | 5 ± 2.5 | * | 5.6 |

The protocol of Example 1 was then applied to BM samples collected from 7 adenosine deaminase deficient severe combined immunodeficient (ADA-SCID) patients, 6 Wiskott Aldrich Syndrome (WAS) affected individuals (3 pediatric and 3 adult). These are two patients with primary immunodeficiency PID whose defects were well characterized in previous studies comprising altered or partially impaired hematopoiesis. ADA-SCID patients exhibit central and peripheral B cell tolerance defects having higher levels of immature CD19+CD10+ B cells in BM and being almost depleted of mature B cells (CD19+) with respect to age matched healthy donors. Instead, the absence of functional WAS protein, causative of the WAS disease, critically affects B cell differentiation, with a decreased frequency of immature B cells and a premature egress of immature B cells from the BM. Upon analyzing BM samples from ADA-SCID and WAS individuals, a reduction of the lymphoid compartment in both types of PID patients with respect to the healthy donor controls was confirmed, as shown in FIG. 3C.

Figure 8:
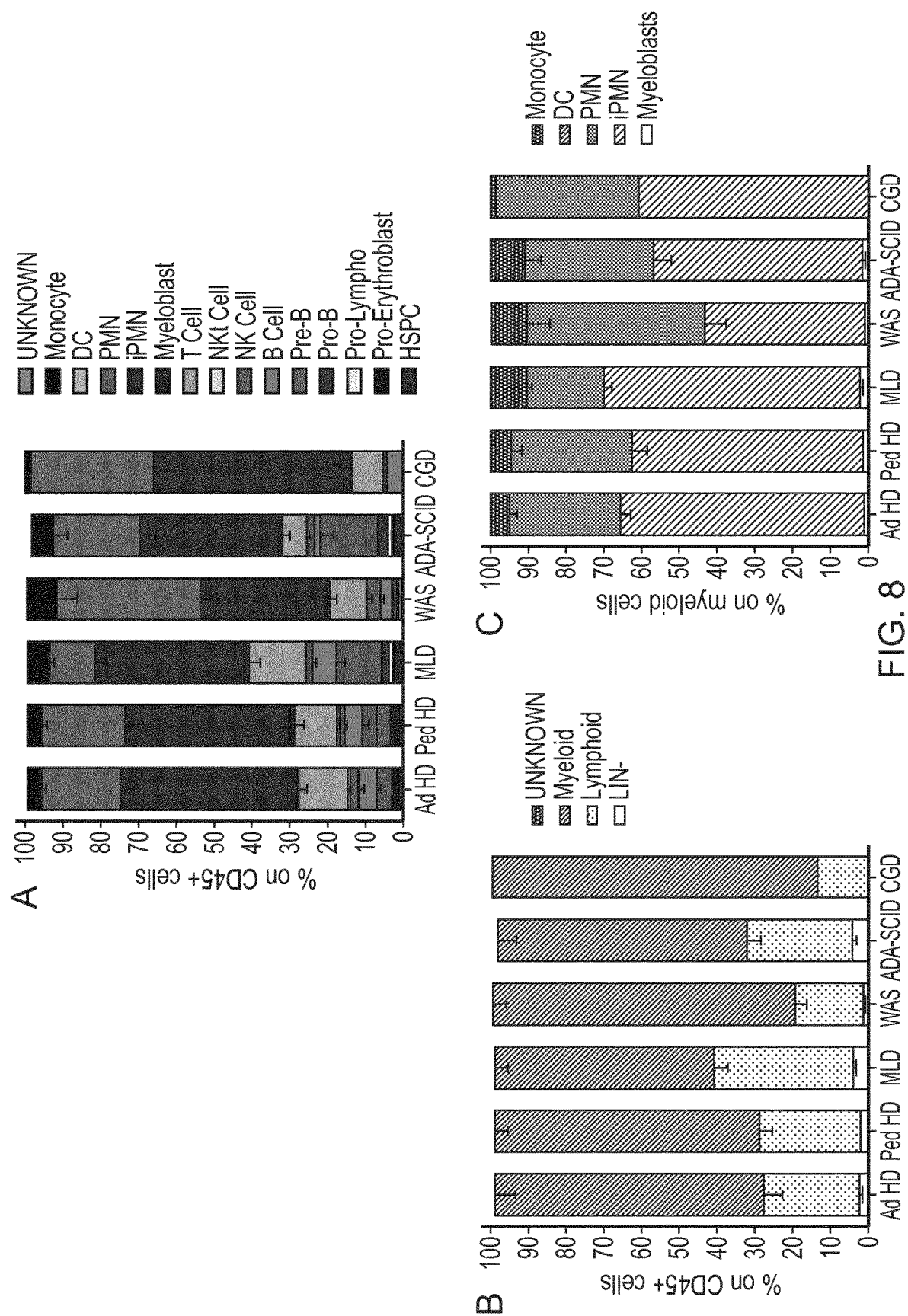
Figure 8:
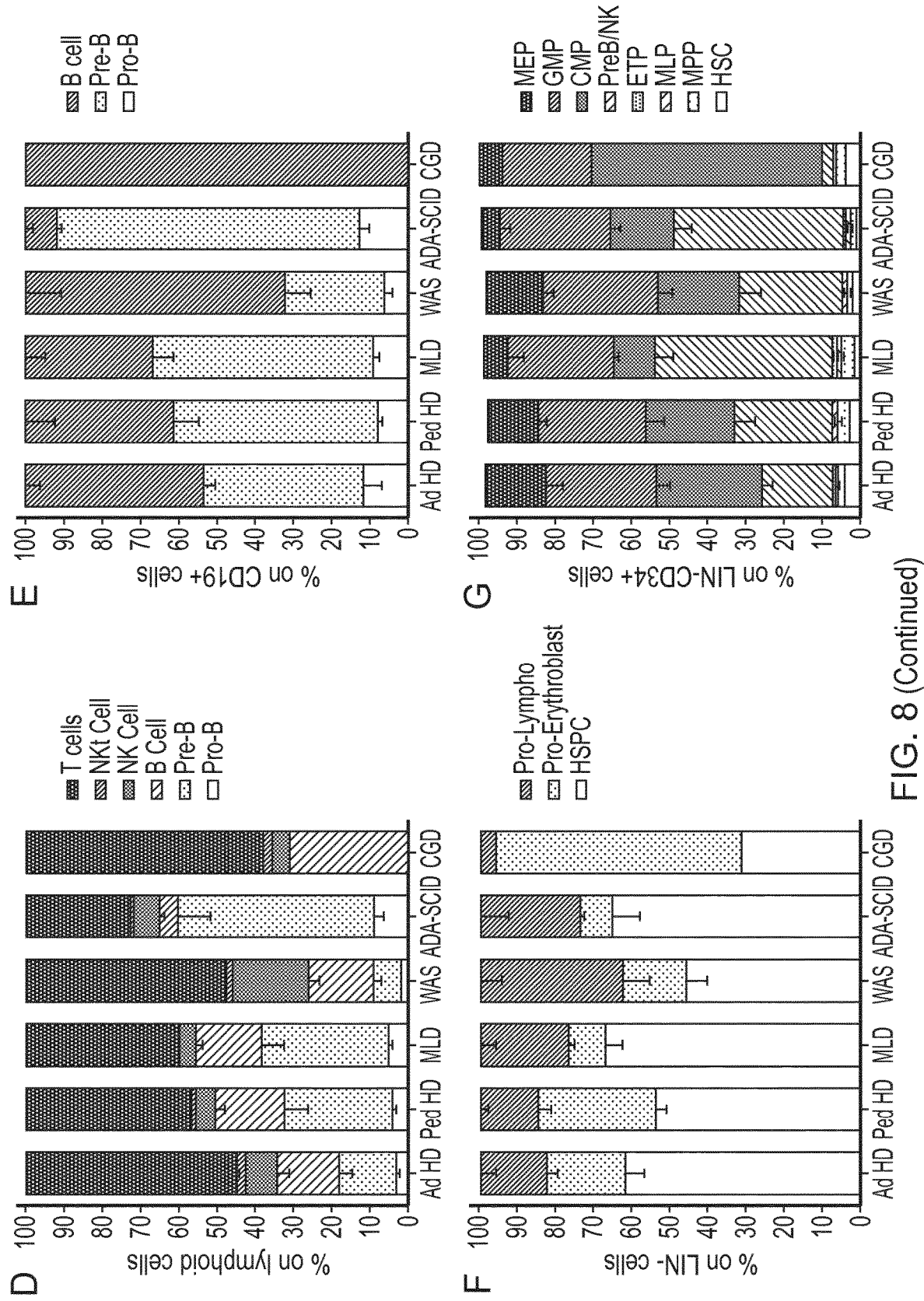
Figure 9A:
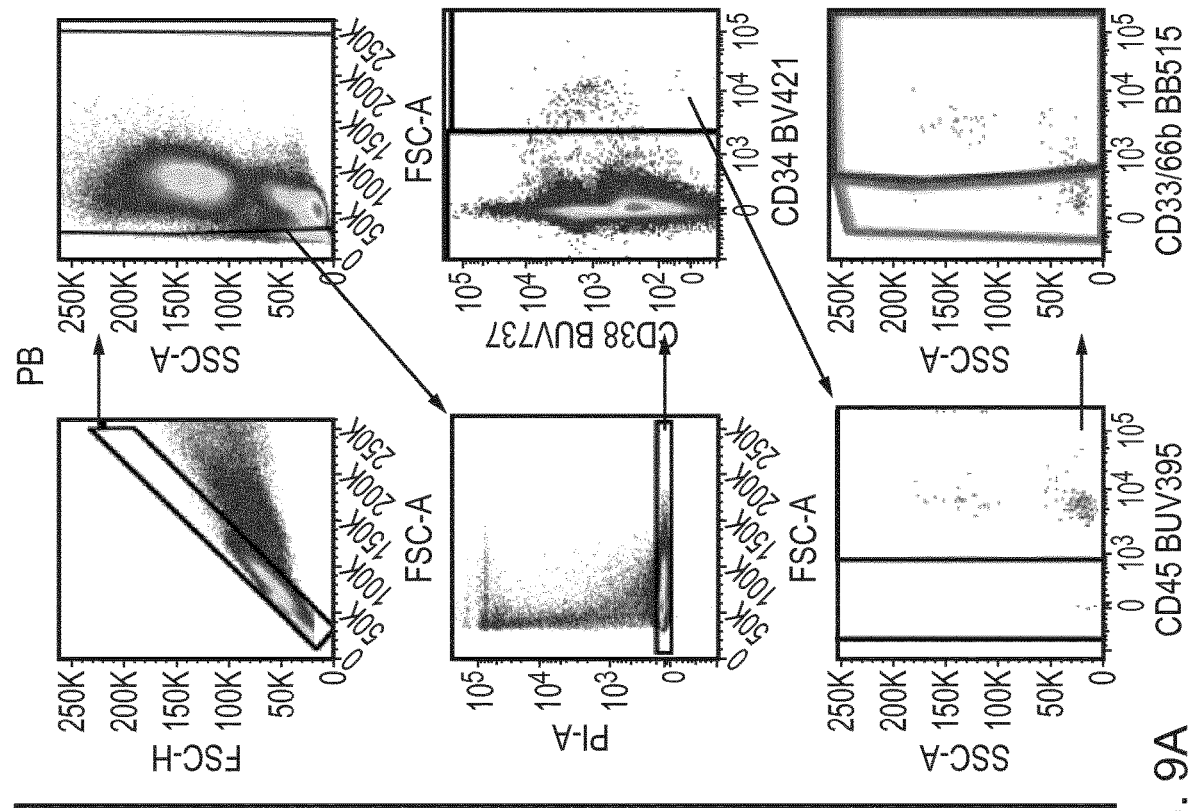
Figure 9A:
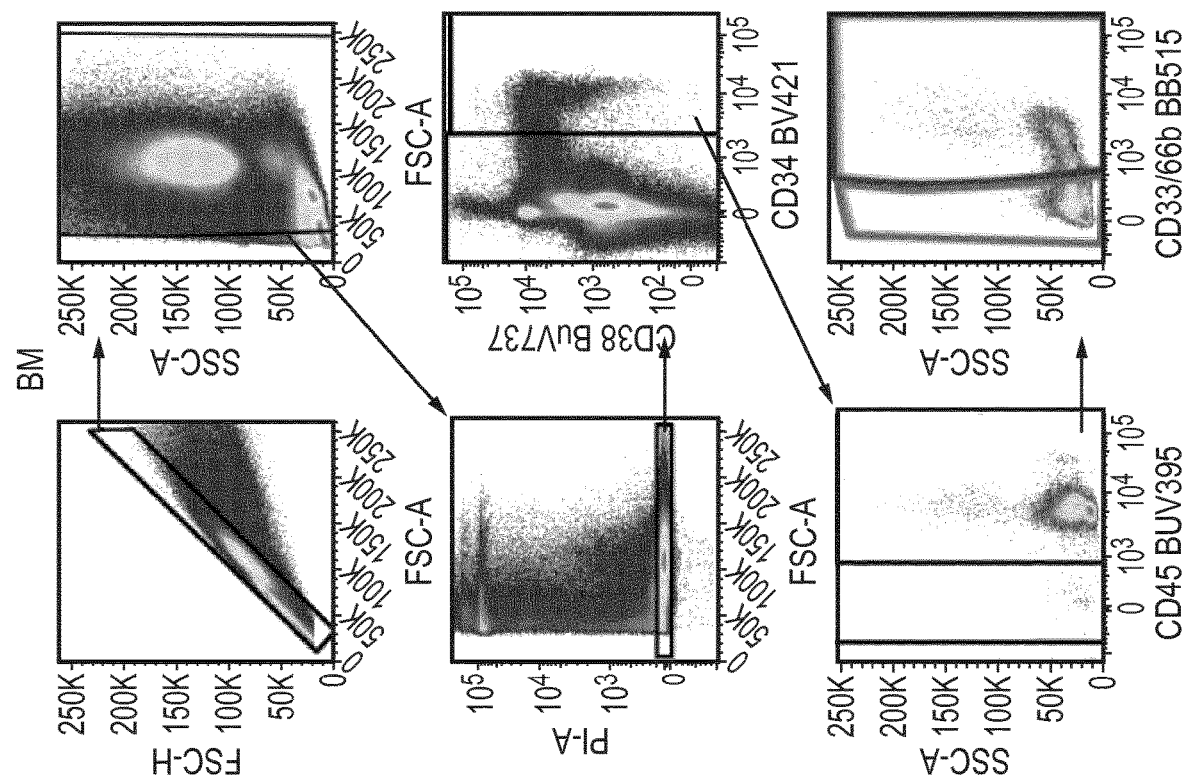
Figure 9B:
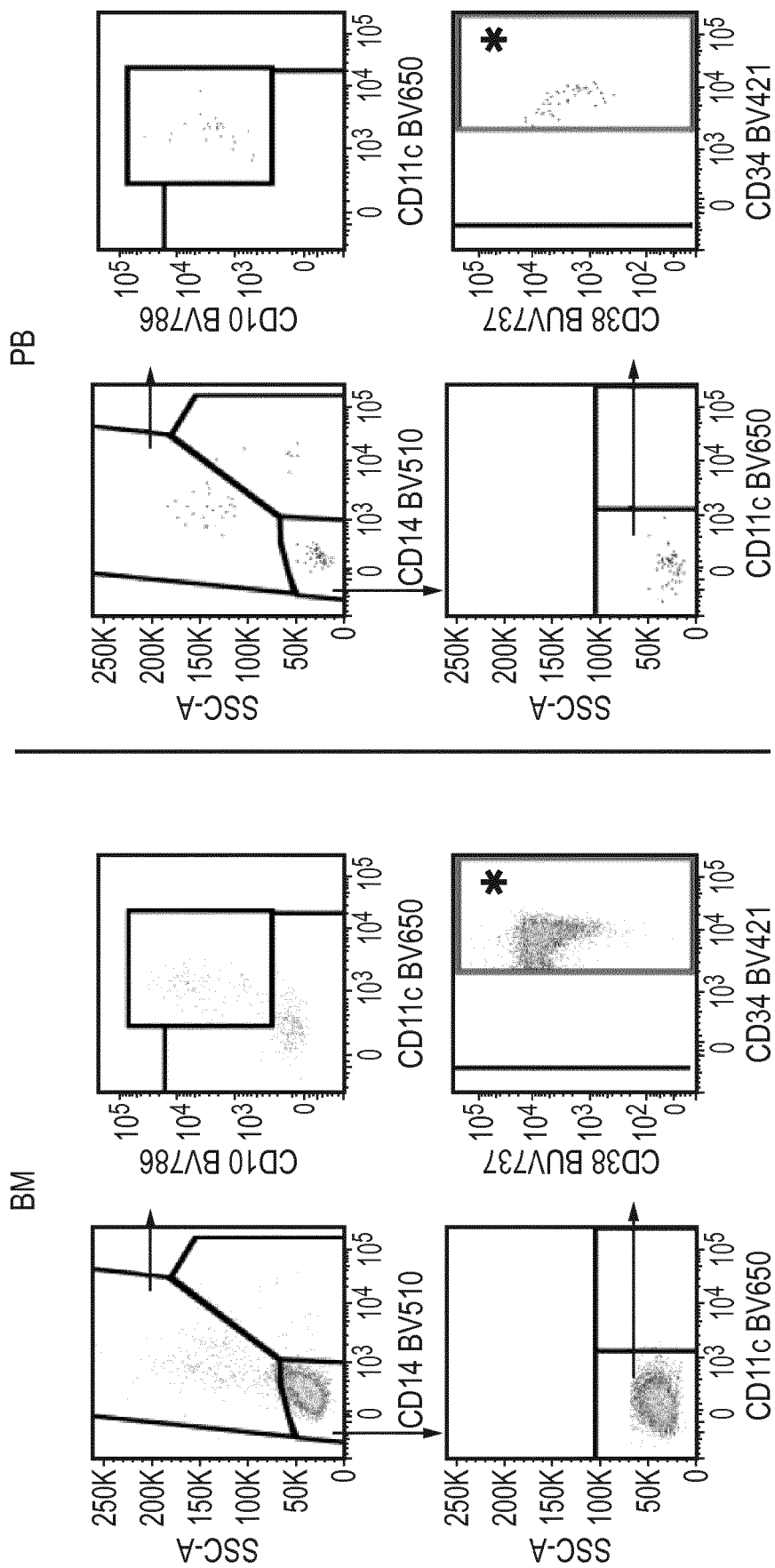
Figure 9C:
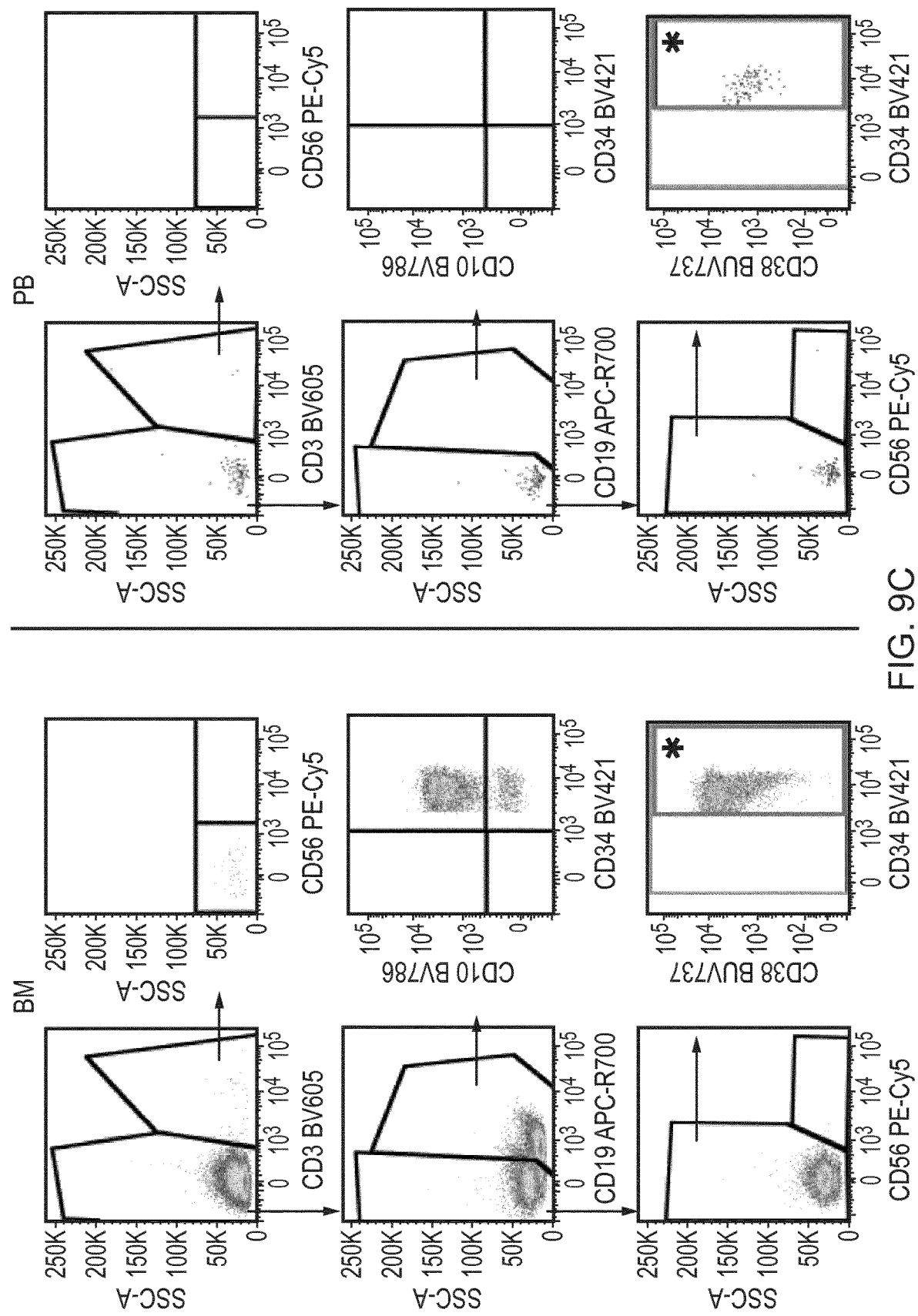
Figure 9D:
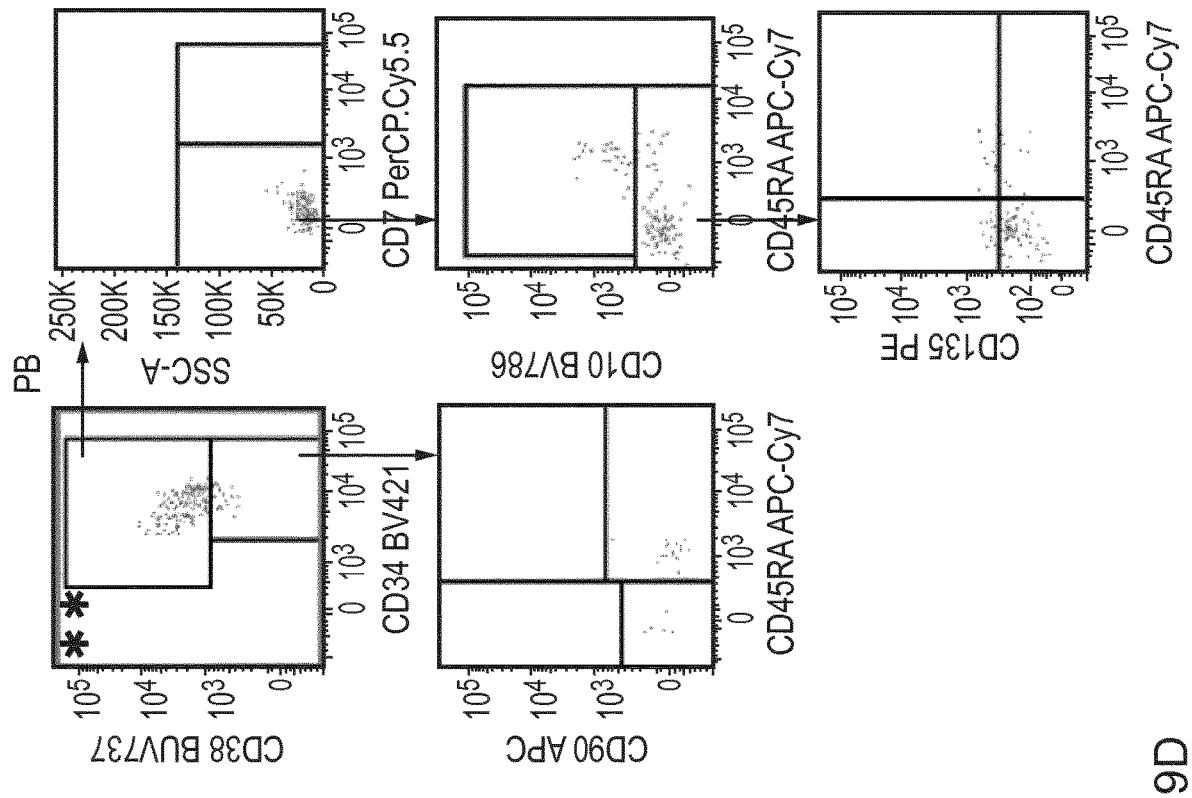
Figure 9D:
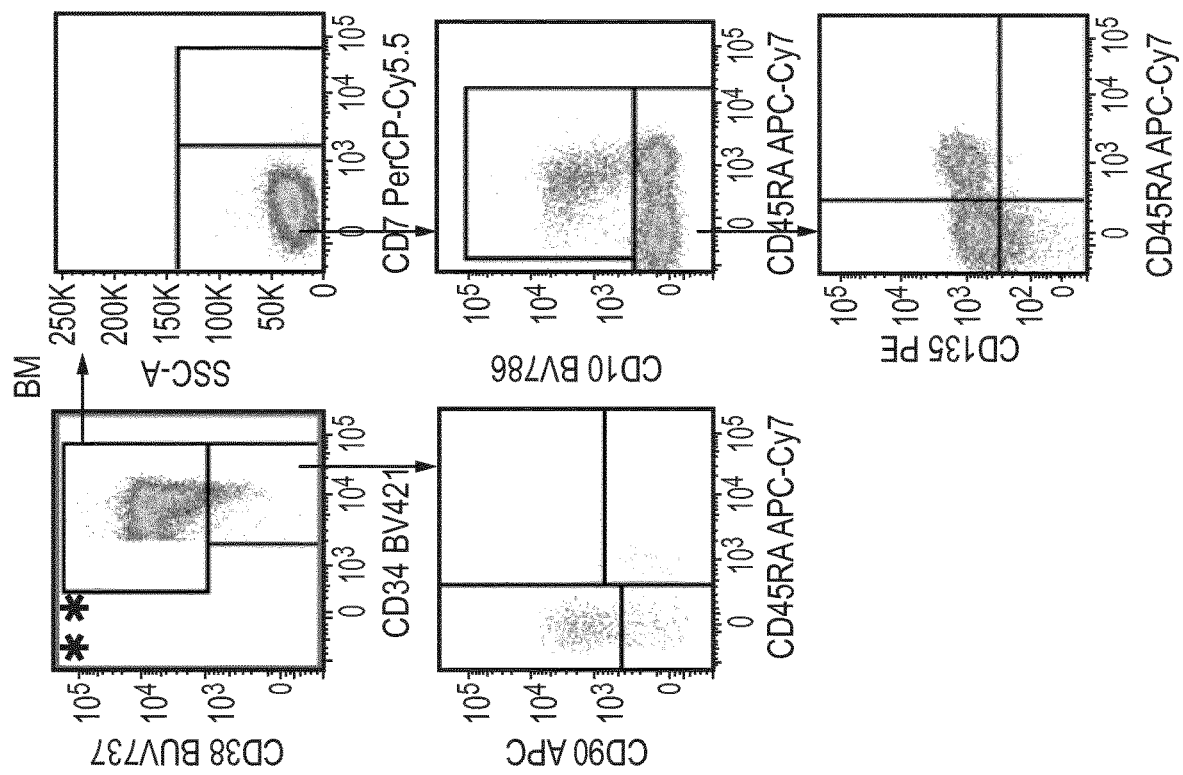

Crucially, the method of the present invention was remarkably efficient in highlighting the unbalanced composition of B-cell compartment in ADA-SCID and WAS patients. In particular, the present invention made it possible in pediatric ADA-SCID patients to observe abnormal population frequencies in line with the characteristic block in B-cell maturation. These patients display a higher content of immature B-cells with respect to age-matched HD (5) (79.4% vs. 53.9% of PreB cells in ADA-SCID and Ped HD respectively. p<0.01 Mann-Whitney test; FIG. 3C and FIG. 8D-E; Tables 7-8) and lower frequencies of mature B cells when calculated on CD19+ cells, on total lymphocytes and on CD45+ cells. In our mixed adult and pediatric WAS patients population, the protocol highlighted the expected lower frequency of the CD19+ lymphocytes (4.7% vs. 11.5% CD19+ cells on total CD45+ cells, p<0.05 Mann-Whitney test) and of the immature Pre-B cell subset within the lymphoid compartment (7.2% vs. 21.7% on total lymphoid cells, p<0.01 Mann-Whitney test; FIG. 3C, FIG. 8D-E; Tables 7-8), as compared to the HD group (Ad+Ped). Importantly, as the protocol allows concomitantly analyzing all major blood cell populations, we were able to retrieve novel information on the BM of PID patients. We could unveil a relative higher percentage of monocytes (7.3% vs. 3.3% on total CD45+ cells; p<0.001 Mann-Whitney test;) and NK cells (20% vs. 6.7% on total lymphoid cells; p<0.01 Mann-Whitney test;) (FIG. 3C, FIG. 8C-D; Tables 7-8) and a reduced HSPC content (0.6% vs. 1.3% on total CD45+ cells; p<0.01 Mann-Whitney test; FIG. 3C, FIG. 8A and Tables 7-8) in our cohort of WAS subjects with respect to HD, while in ADA-SCID patients we found a significant decrease of primitive HSC with respect to Ped HD (0.7% vs. 2.7% of HSC on HSPC in ADA-SCID and Ped HD respectively; p<0.01 Mann-Whitney test; FIG. 3C, FIG. 8G and Tables 7-8). We also exploited the protocol to analyze a BM sample of a patient affected by Chronic Granulomatous Disease (CGD), a PID in which myeloid cells are unable to kill bacteria through phagocytosis. Differently from ADA-SCID and WAS immunedeficiencies where lymphoid subsets are the most impaired subpopulations, CGD patients display defects in myeloid cell function. This characteristic appears evident when we analyzed BM sample from a CGD patient. Indeed we found a relative expansion of myeloid subsets, with the vast majority of mature CD45+ cells belonging to myeloid compartment (iPMN and PMN) (FIG. 3C, FIG. 8A-C and Tables 7-8). Moreover, we observed that also HSPC are mainly composed by myeloid progenitors (CMP and GMP) with a marked absence of PreB/NK progenitors, resulting in the loss of Pre-B and Pro-B lymphocytes (FIG. 3C, FIGS. 8D, E and G; Tables 7-8).

As additional controls of non-hematological diseased individuals, the BM composition of 6 pre-symptomatic metachromatic leuko-dystrophy (MLD) patients was analysed. MLD is an inherited lysosomal storage disease caused by arylsulfatase A (ARSA) deficiency and no hematopoietic alterations have been described for pre-symptomatic MLD individuals. As depicted in FIG. 3D, it was observed that MLD patients have a blood cell composition similar to Ped HD, with only a slightly higher contribution of CD19+ lymphocytes probably due to the very young age of these individuals (20.2% in MLD vs. 13.4% in Ped HD of CD19+ cells on CD45+ cells; Table 7-8).

Example 5

Analyses of Acute Myeloid and Lymphoid Leukemia Samples

Figure 4:
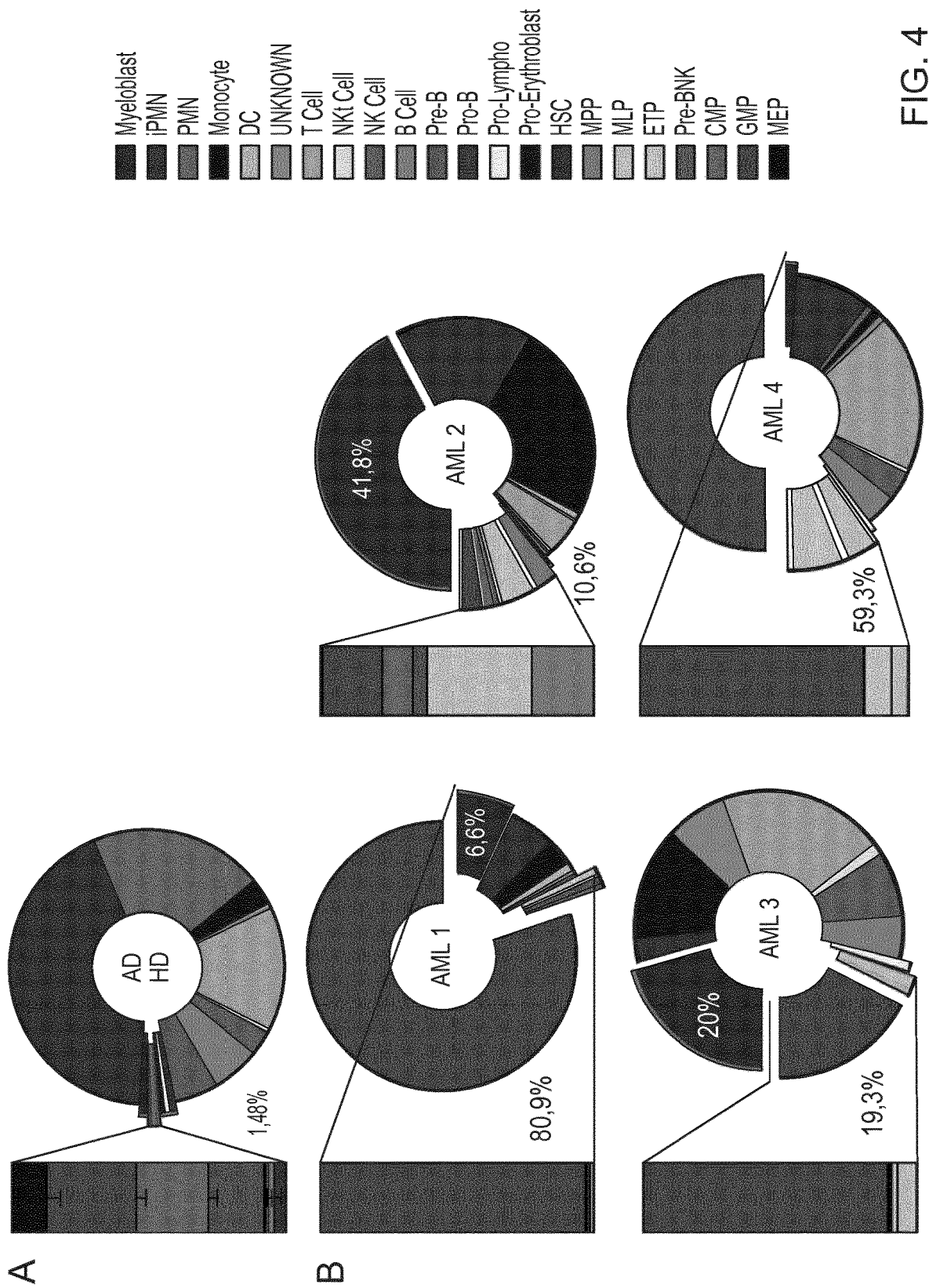
Figure 4:
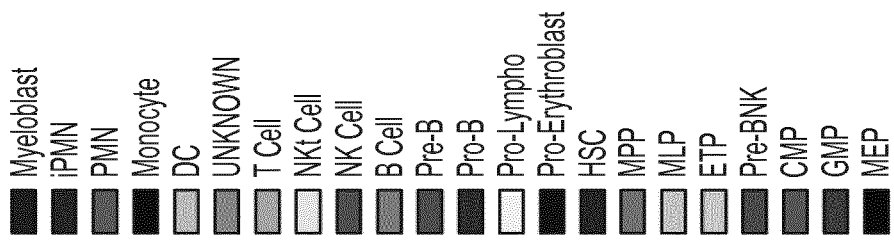
Figure 4:
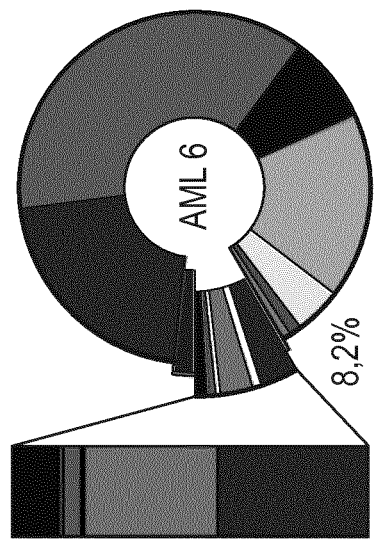
Figure 4:
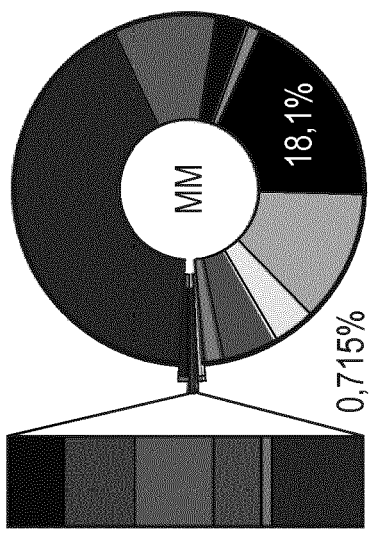
Figure 4:
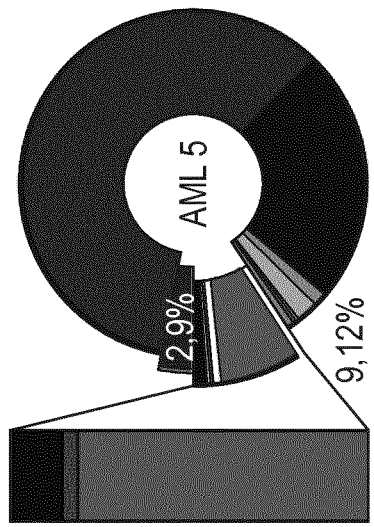
Figure 4:
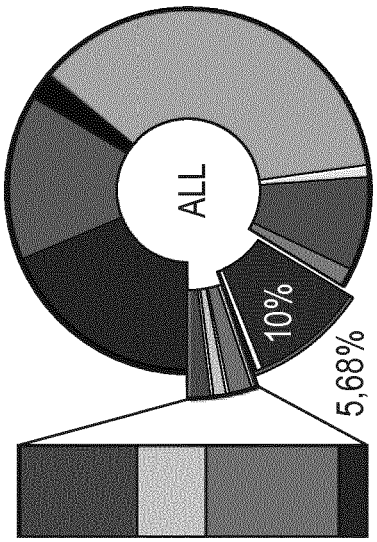
Figure 5:
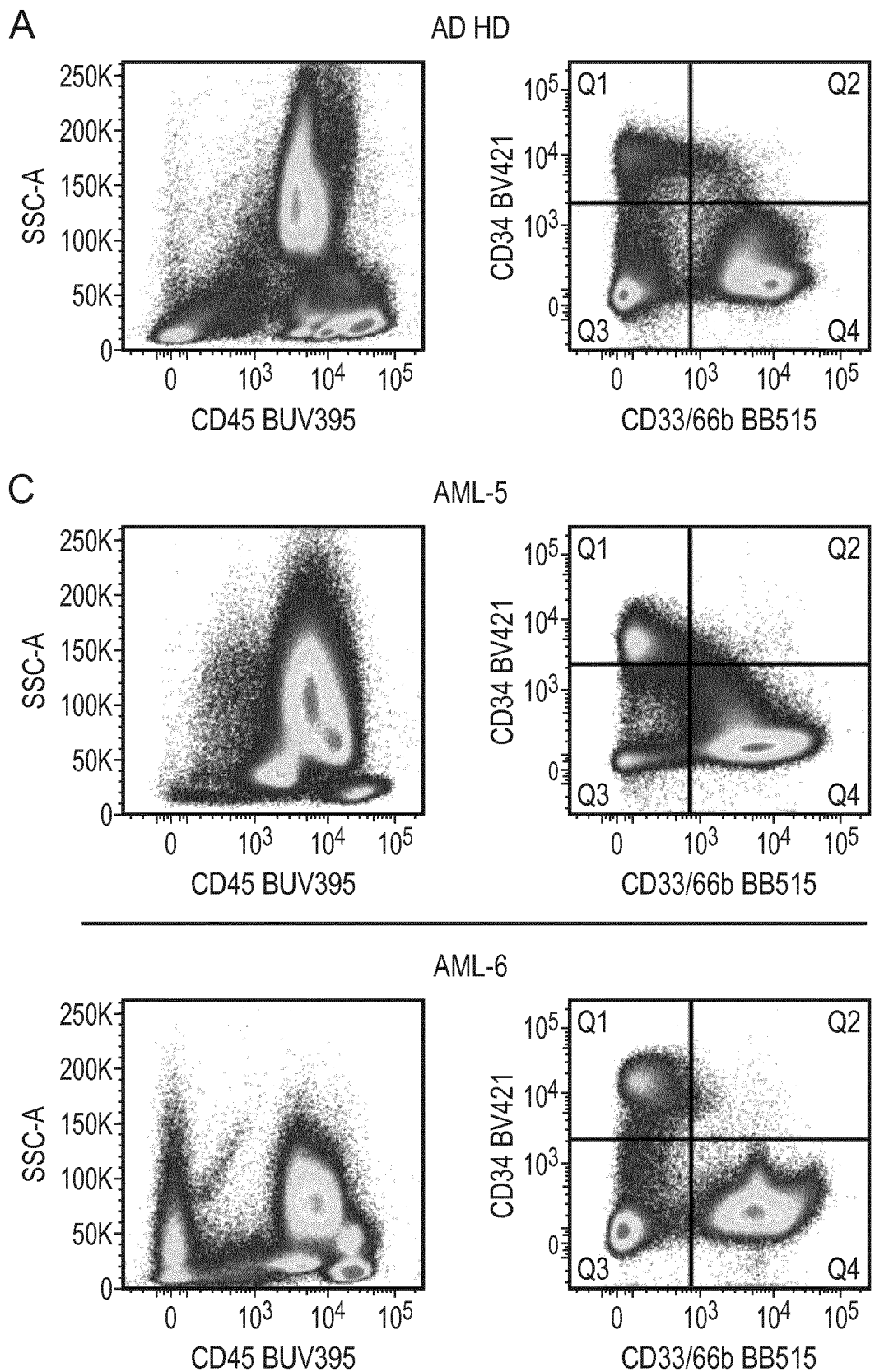
Figure 5:
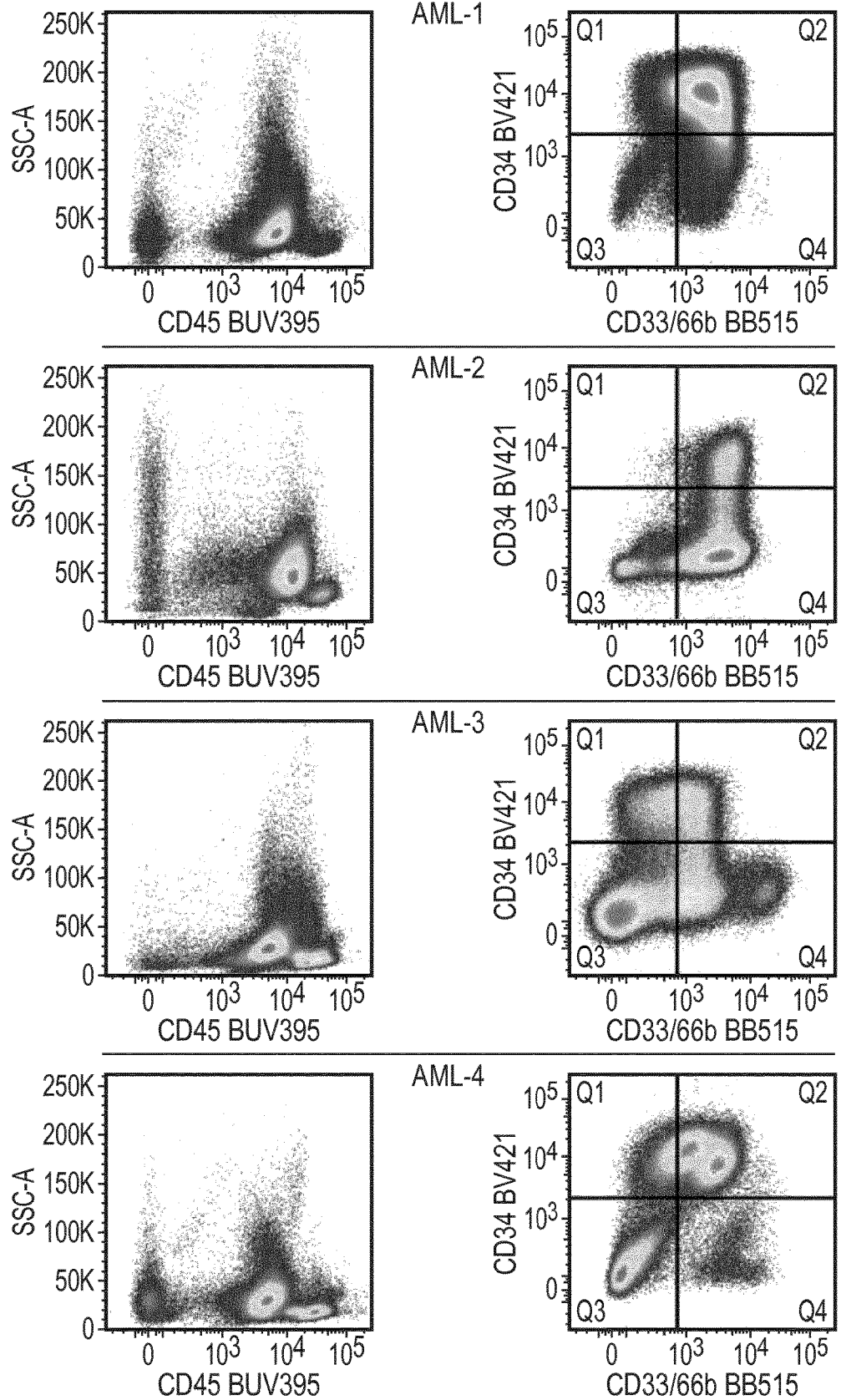
Figure 5:
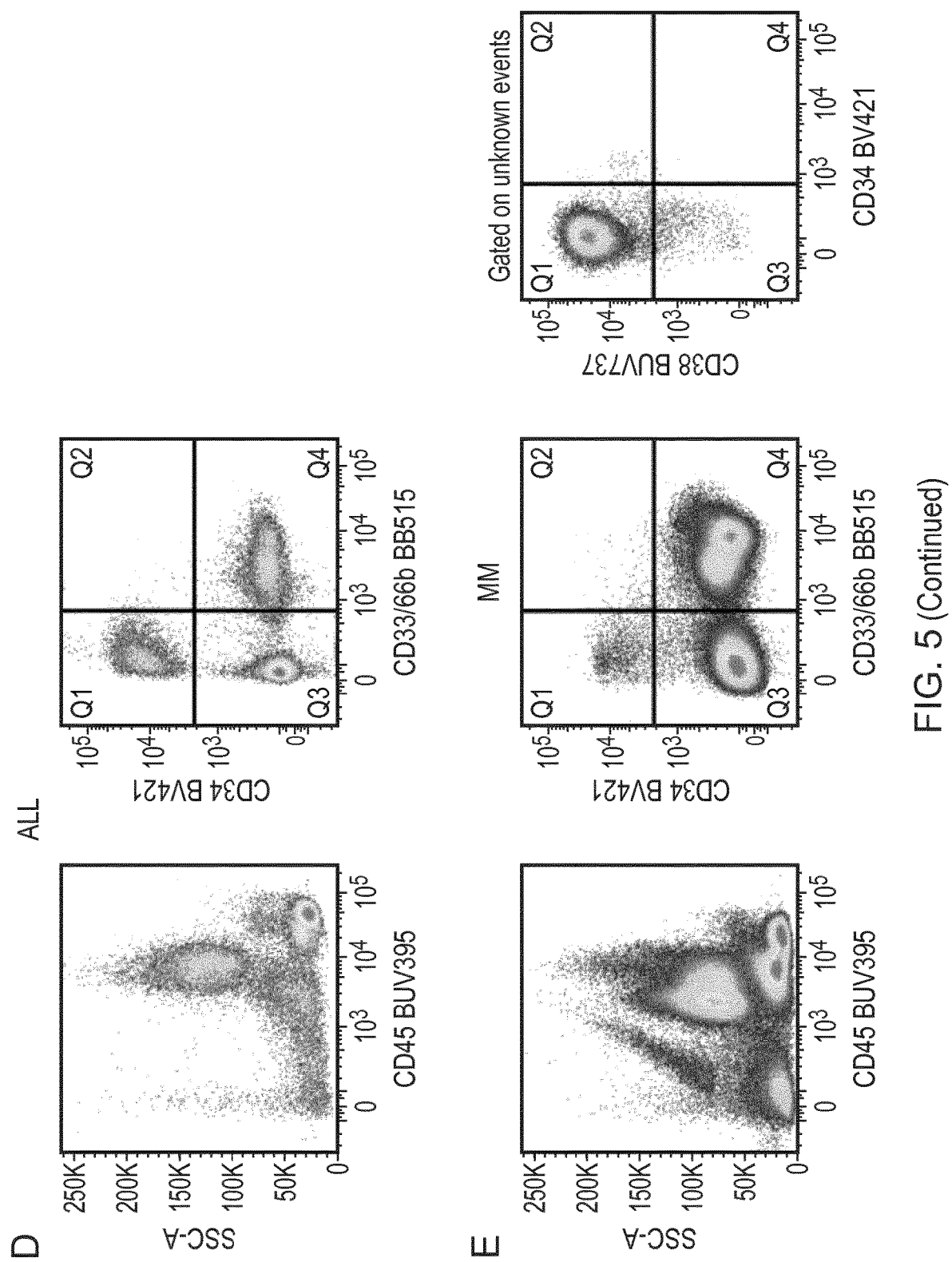

In order to provide a qualitative assessment on the capability of the methods according to the present invention to detect unbalances in the hematological tumors, the efficacy the protocol was test on four BM samples from patients with acute lymphoid leukemia (ALL; n=1) and acute myeloid leukemia (AML; n=6) (FIGS. 4-5 and Table 6). BM samples from patients at diagnosis/relapse were analysed, where the expanded clones accounted for the 80-90% of the analysed materials, and 3 BM samples from patients after chemotherapy, in which only a residual fraction of the aberrant clone was detectable.

As shown in FIG. 4, use of the present invention highlighted abnormal compositions of hematopoietic compartment and the presence of immature blasts displaying low levels of CD45 marker in all the BM samples analysed (FIGS. 4-5). Indeed, it was possible to discriminate between myeloid and lymphoid leukemia according to the accumulation of blasts bearing myeloid (AML-1-3, FIG. 4B-C) or lymphoid (ALL, FIG. 4D) markers. The classification of myeloid or lymphoid leukemia was achieved by analysing the expression of CD33 in combination with CD34 marker (FIG. 5). While in the HD the two major branches of hematopoietic differentiation were identified (FIG. 5A, immature not-myeloid-biased [Q1] and immature myeloid-biased [Q2] progenitors mature not-myeloid cells [Q3] and mature myeloid cells [Q4]).

In the acute leukemic samples a skewing towards a single differentiation pathway and an accumulation of a particular stage of maturation was observed. Furthermore, given the high number of markers and cell subtypes concomitantly detectable by using a method according to the present invention, the level of differentiation of the aberrant leukemic clones could be assessed. In particular, by analysing the composition of the two acute myeloid leukemia samples, it was observed that AML-1 and AML-4 showed an accumulation of a less differentiated "GMP-like" population while AML-2 and AML-3 displayed more mature myeloblast-like phenotype (FIG. 4B).

Furthermore, to evaluate the sensitivity of the protocol, 3 samples from patients after treatments expected to bear approximately 10% residual leukemic blasts, according to previous standard diagnostic tests, were analysed (Table 6). As shown in FIG. 4C-D, by using a protocol according to the present invention it was possible to detect aberrant blood composition in these samples. Importantly, the frequency of putative blasts, measured through Whole Blood Dissection (WBD), was in good accordance with the previous diagnosis (12%, 8.2% and 15.7% of CD45+ cells in AML-5, AML-6 and ALL, respectively).

Figure 3:
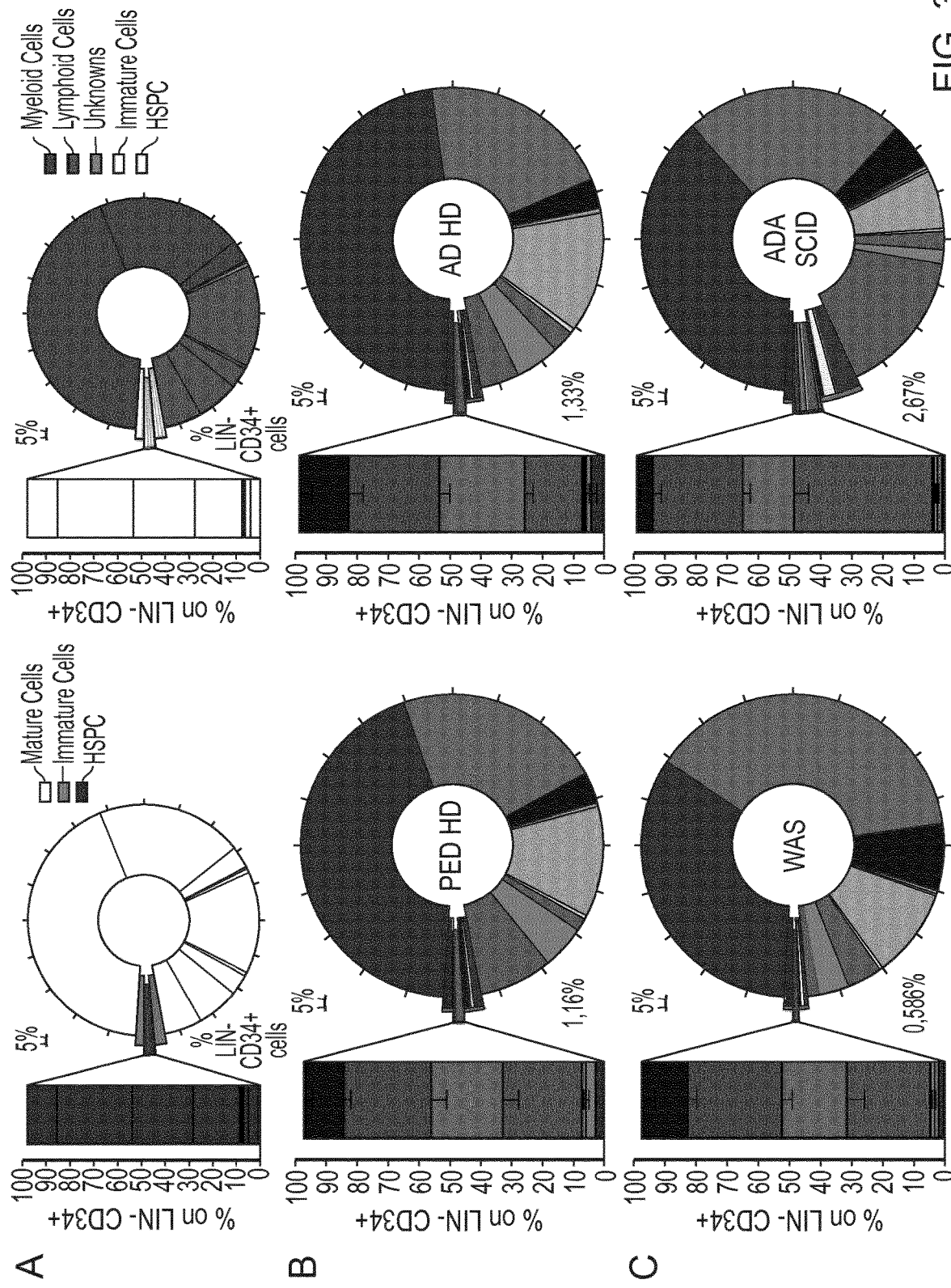
Figure 3:
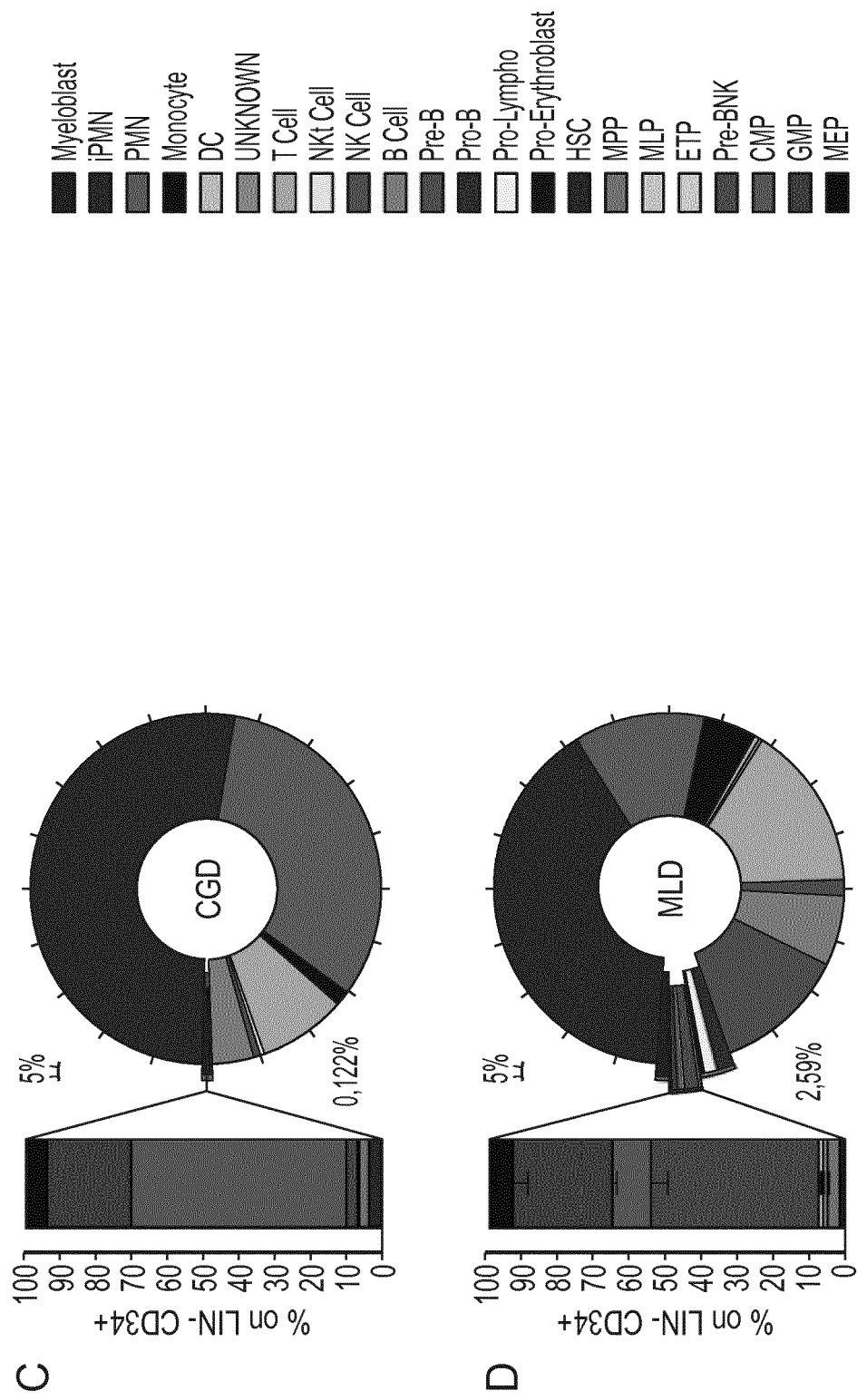

Finally, we had the opportunity to analyze the BM of a patients newly diagnosed with a low-differentiated Multiple Myeloma (MM). Interestingly, as shown in FIG. 4E, we could detect a population of cells constituting 19.3% of total BM belonging to the fraction of unassigned events which usually represents on average only 0.2% of a normal BM sample (FIG. 3 and FIG. 8A). Strikingly by characterizing this population for the expression of all the other protocol markers we found that the 93.8% of these events were highly positive for the CD38 marker (FIG. 5E). This suggests that, through the protocol, we most likely identified an accumulation of infiltrating plasmablasts (commonly identified as $CD45^{mid}$ $CD38^{high}$) in the BM of this individual which accounted for 18.1% of the total CD45+ cells.

Example 6

Figure 10:
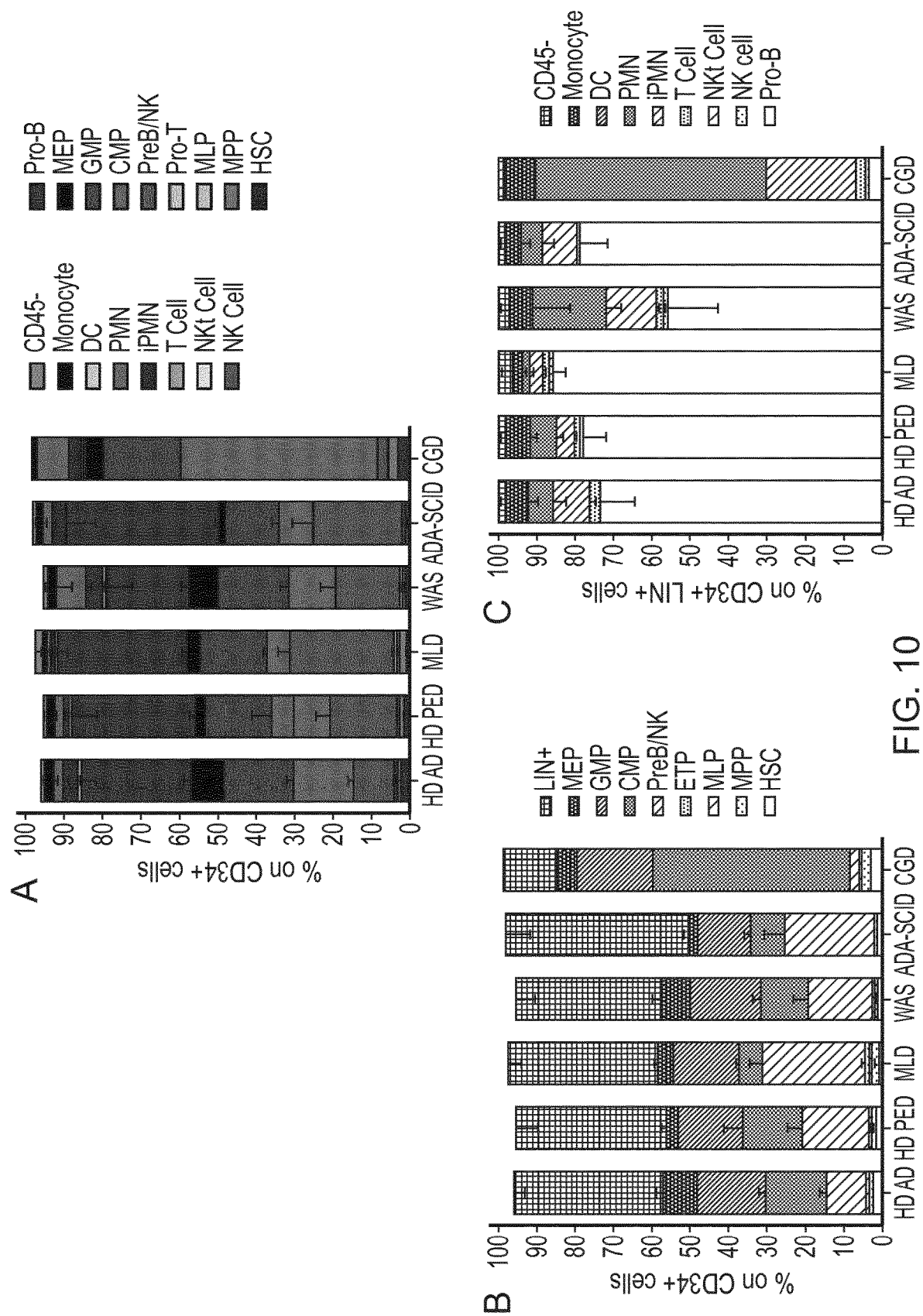

Focusing on HSPC: an Alternative Gating Strategy for Whole Blood Dissection (WBD) Protocol HSPC represent a fundamental cell source widely exploited in clinics, given their fundamental role in the maintenance of the hematopoietic homeostasis. Thus, over the years particular attention was given to study in depth the biology of HSPC subpopulations and their maintenance upon stressed conditions, such as transplantations or gene therapy. Moreover, the characterization of HSPC in diseased state or during different stages of life would allow unveiling functional defects requiring correction. In order to focus on HSPC subpopulations, we adapted our protocol gating strategy to assess the composition of CD34+ cells in both PB and BM samples (FIG. 9). After gating on live cells, we identified CD34+ population, enriched for hematopoietic progenitors. We then applied the same gates and population marker definitions used in the classical gating strategy (FIG. 1 and Table 1) to analyze the composition of all the LIN+CD34+ and HSPC subsets. With the aim to characterize CD34+ cells in our cohort of healthy donors and patients, we exploited the adapted gating strategy to analyze the same BM samples previously described (FIG. 3 and FIG. 10). As expected, Pro-B cells constitute the vast majority of LIN+ CD34+ cells in all the groups, except for the CGD patient that displays a LIN+CD34+ compartment mainly composed by iPMN and PMN (FIG. 10).

Example 7

Precision Count Beads™ Allow Absolute Quantification of Cells Analyzed through Whole Blood Dissection (WBD)

Figure 11:
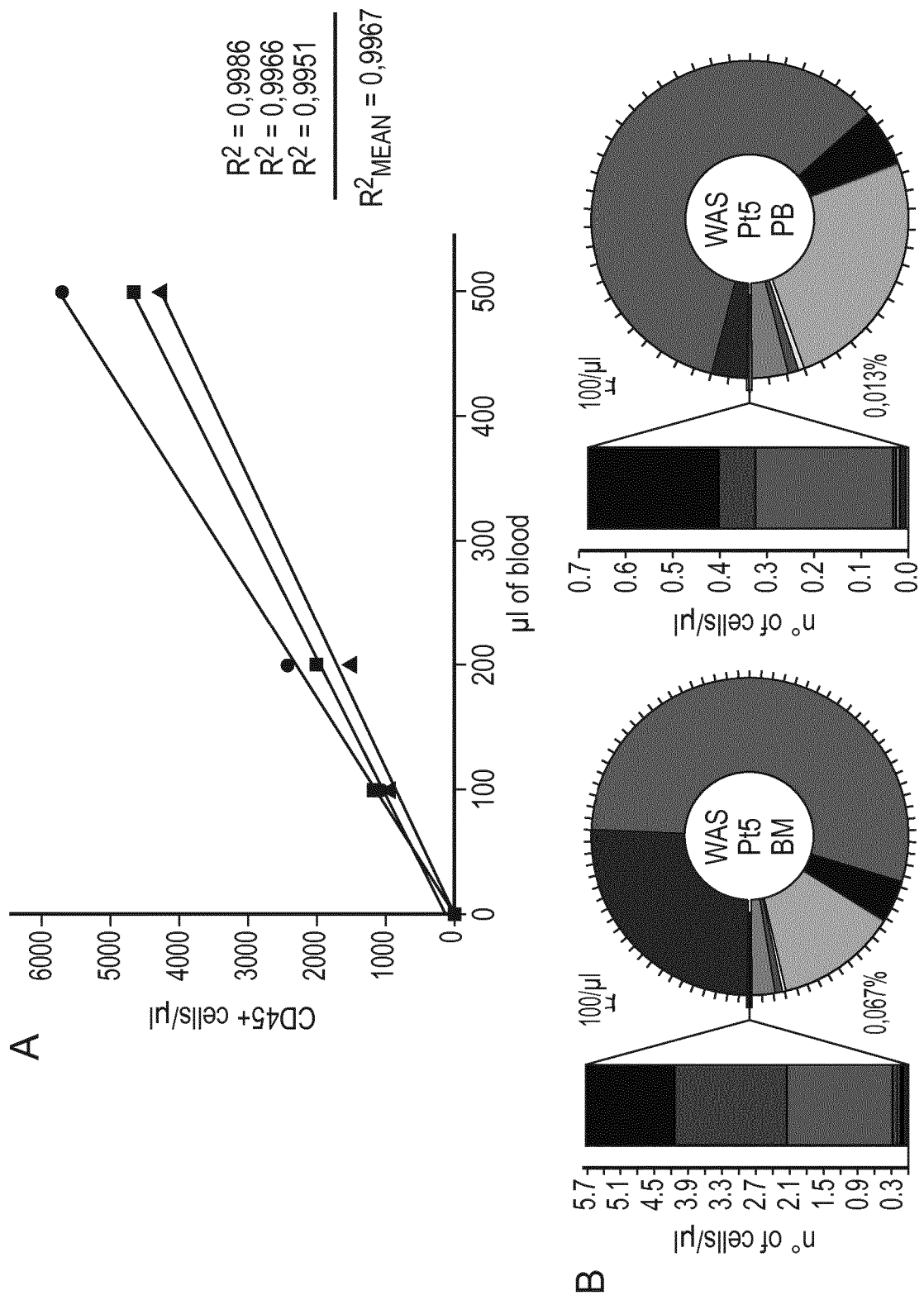
Figure 11:
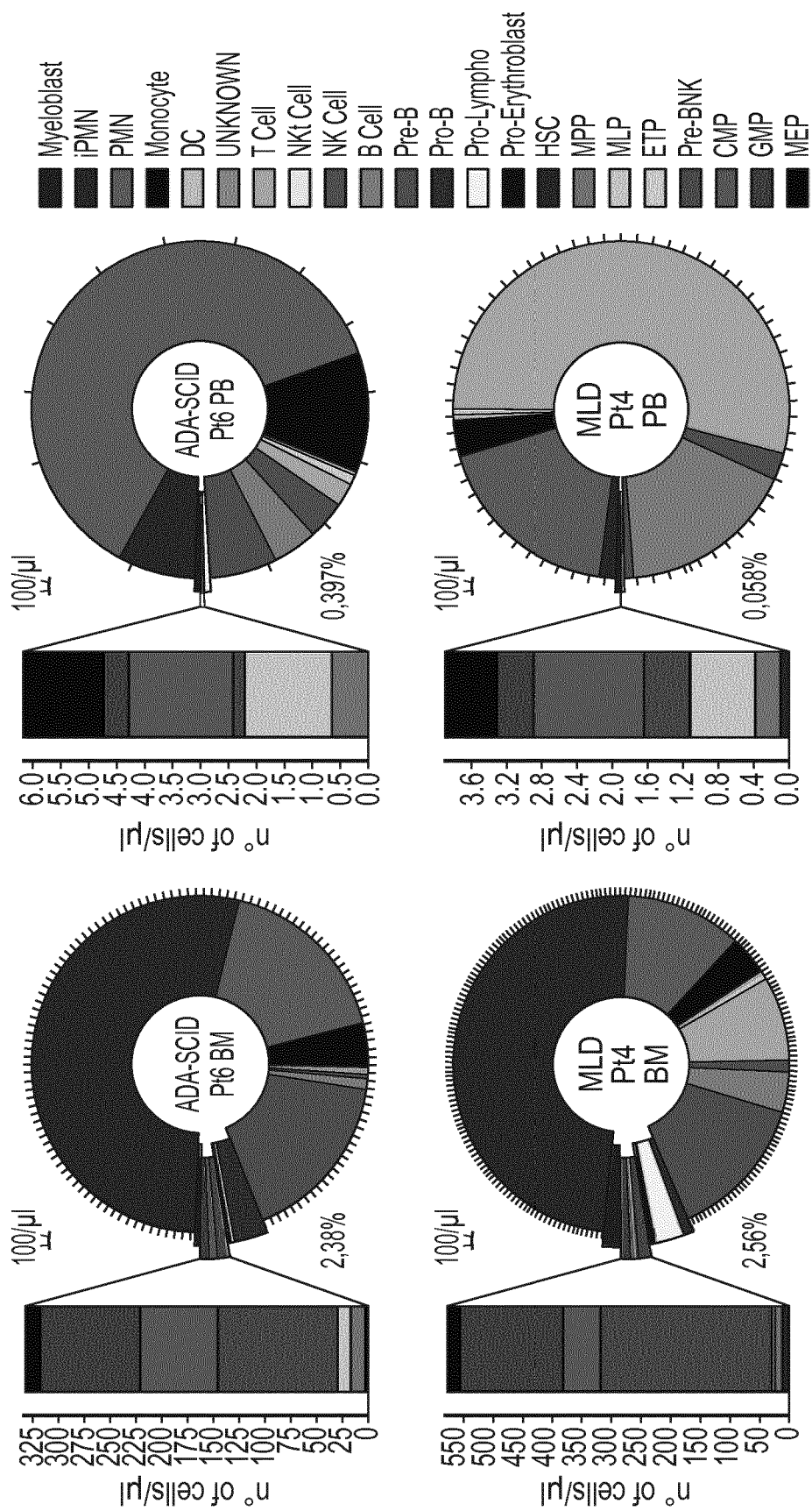

In order to improve our analysis from a quantitative point of view, we tested the addition of Precision Count Beads™ to allow the absolute quantification of the different hematopoietic subpopulations identified. We evaluated the reliability of our cell count by performing serial dilutions of 3 HD PB into PBS. As shown in FIG. 11A, we found a significant linear regression ($R^2 > 0.99$) of the cell count obtained in all the 3 biological replicates.

We also analyzed both PB and BM samples from the same patients in 5 ADA-SCID, 2 WAS and 3 MLD affected individuals. The diverse cell count and composition obtained are in line with the expected differences in the two blood sources (FIG. 11B), thus, proving that the protocol of the invention can provide not only qualitative evaluation but also absolute number quantification of cell subpopulations composing a given blood sample.

Example 8

Analyses of Human Graft in Xeno-Transplanted Mice

Given the protocol's human-specific design, we identified the human-in-mouse transplantation setting as one of the most relevant applications of the invention. With the aim to evaluate the feasibility of using the protocol of the invention in xenografts, we transplanted human cord-blood (CB) derived HSPC into sub-lethally irradiated NSG mice (n=3 NSG and n=3 SGM3). NSG mice are known to preferentially support the B-cell lymphoid differentiation and SGM3 mice were developed in order to overcome such limitation, allowing also the differentiation of myeloid cells. We analyzed the human hematopoietic cells into PB after 6 (FU1) and 13 weeks (FU2) (FIG. 12A). At week 16 (FU3) surviving mice were euthanized and PB, SPL and BM were collected (FIG. 12A-B). As shown in FIG. 12C, we were able to detect human cells at the different follow-up with high specificity since we did not detect any unspecific binding of human antibodies in PB of untreated mice. Through the protocol of the invention we could evaluate the level of engraftment in PB in all the time-points analyzed and the different content of human cells in the different blood/cell sources. Analyzing the engraftment over time, although we observed a decrease in the percentage of human cells in the PB of transplanted mice, the absolute number of human cells appeared to increase during time, thus suggesting that the lowering of human cell content in terms of percentages is due to the take over of murine hematopoiesis (FIG. 12D).

Figure 12:
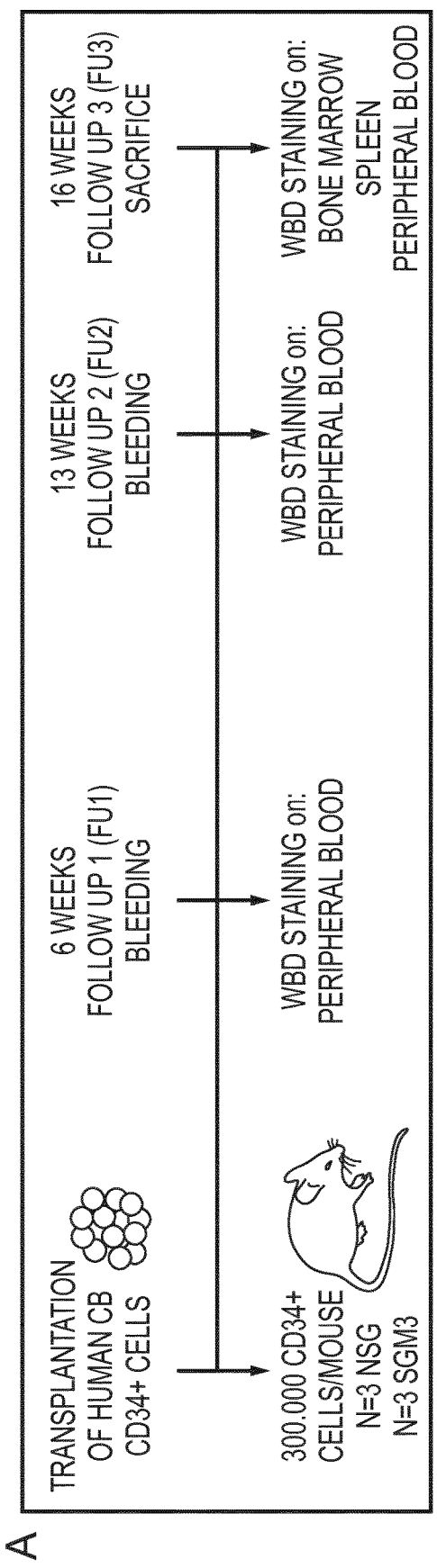
Figure 12:
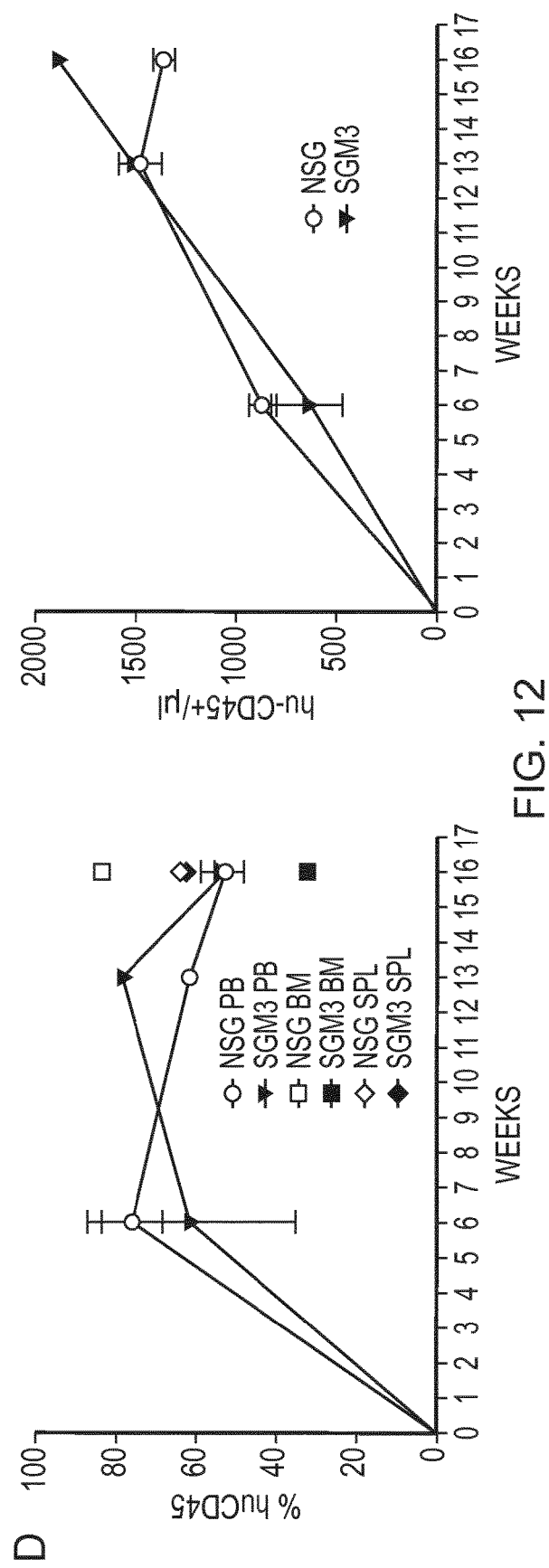
Figure 12:
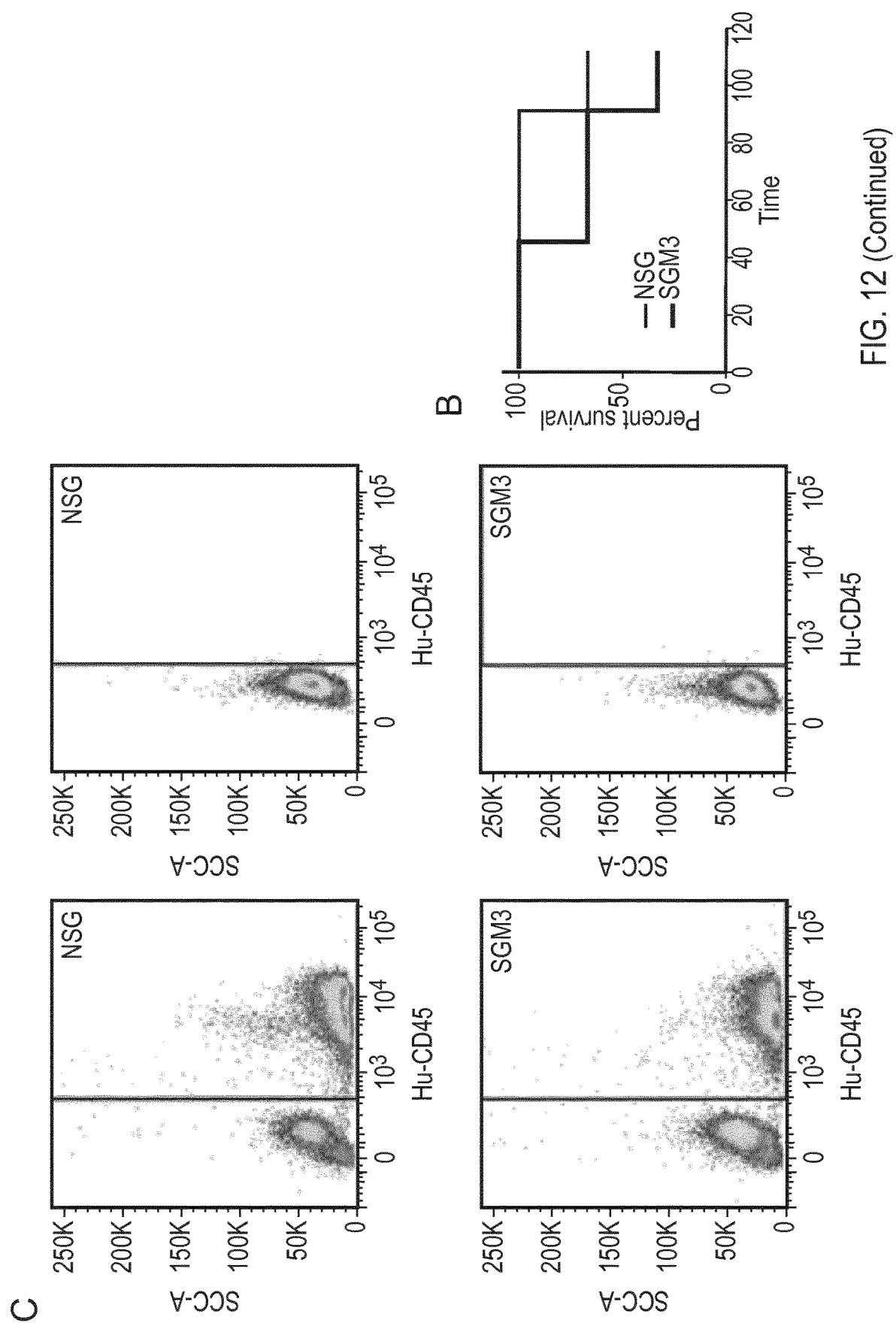
Figure 12:
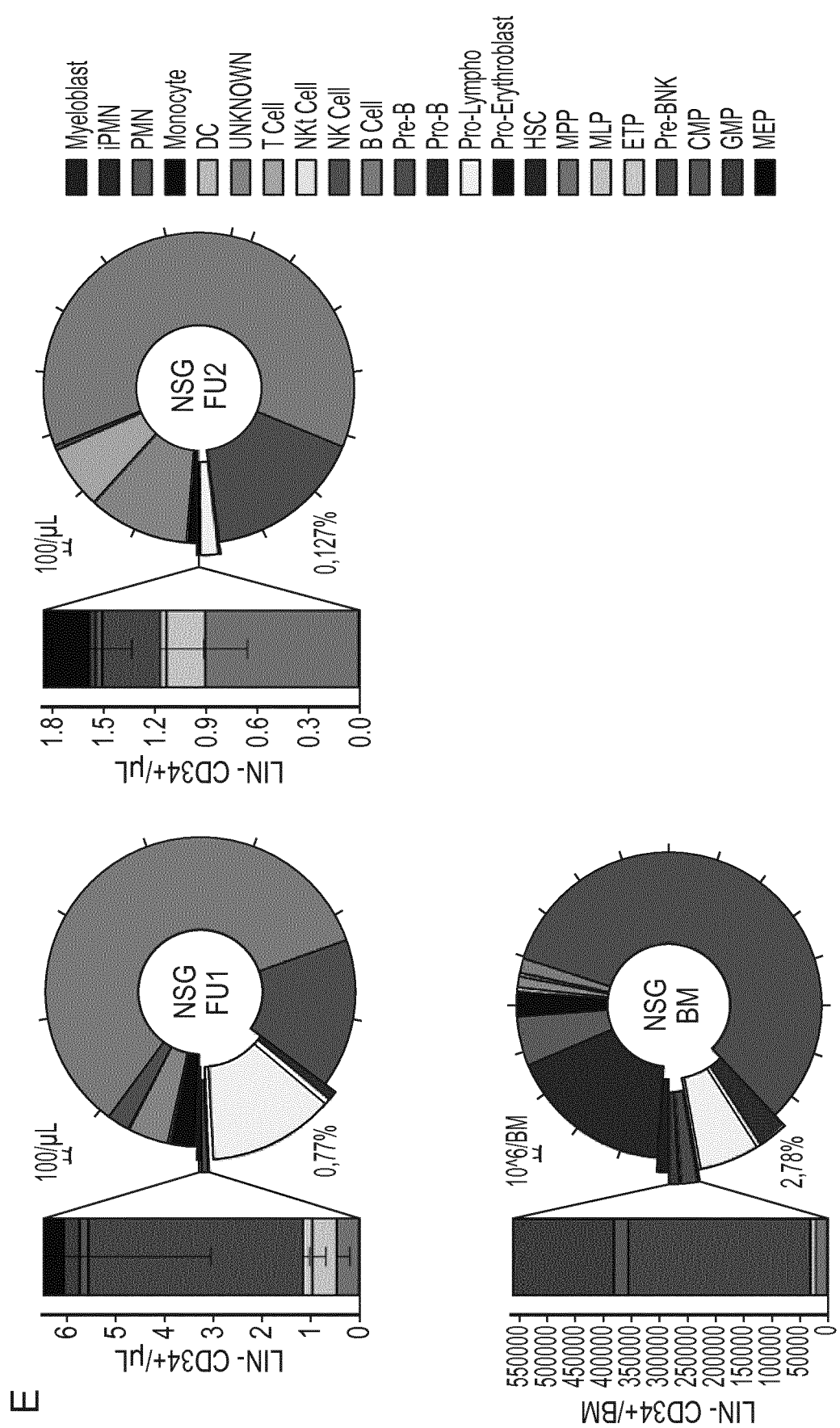
Figure 12:
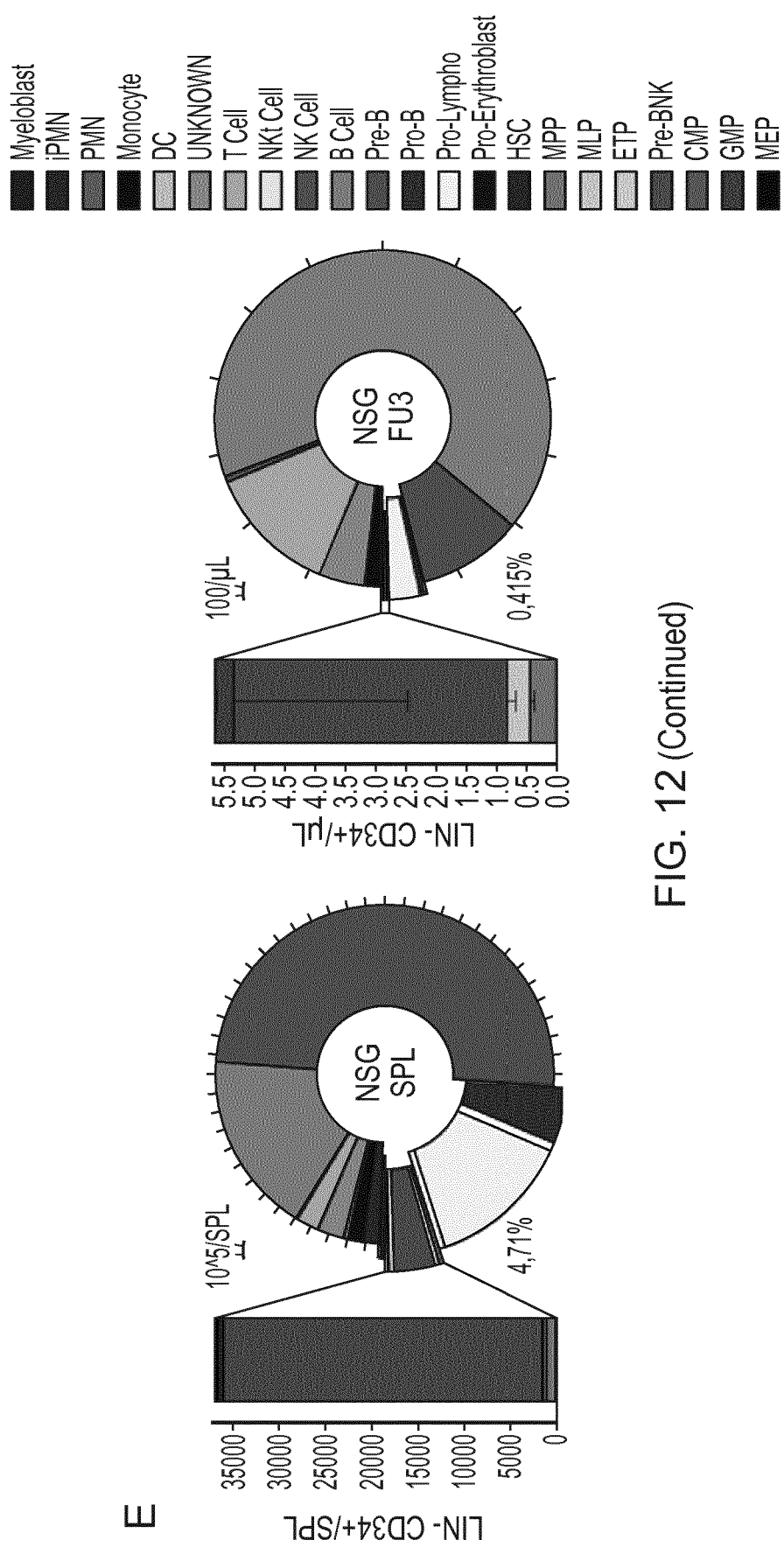
Figure 12:
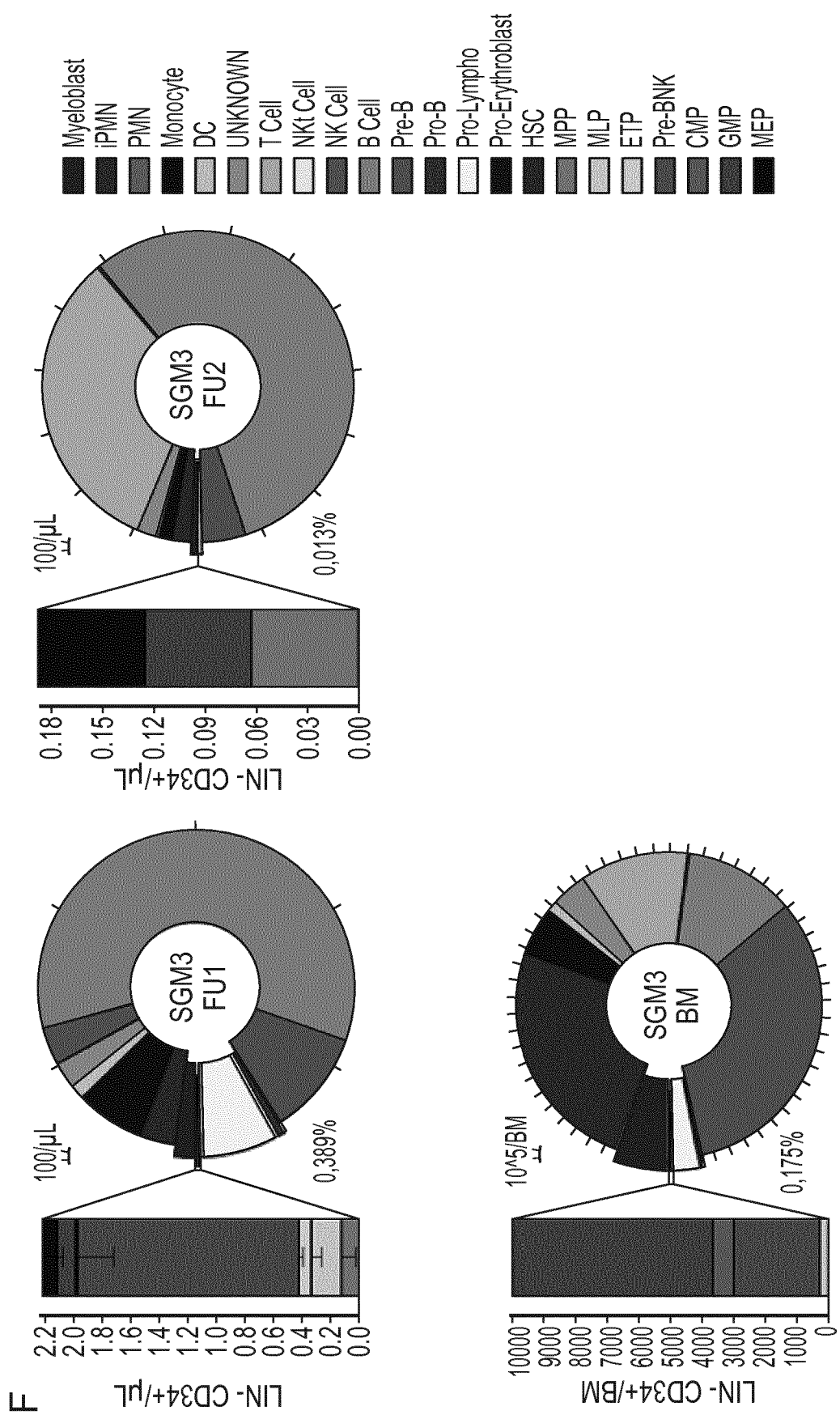
Figure 12:
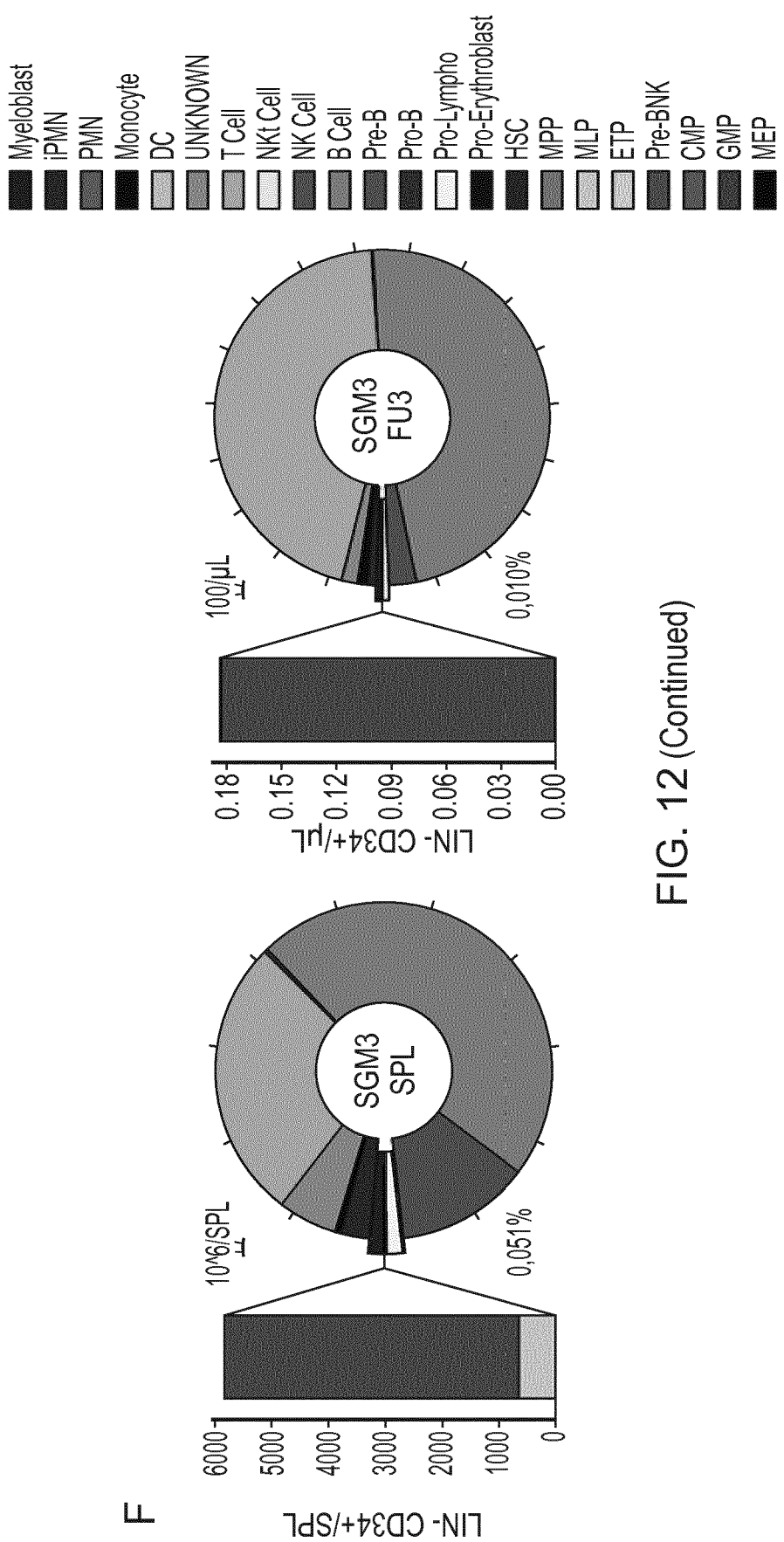
Figure 13:
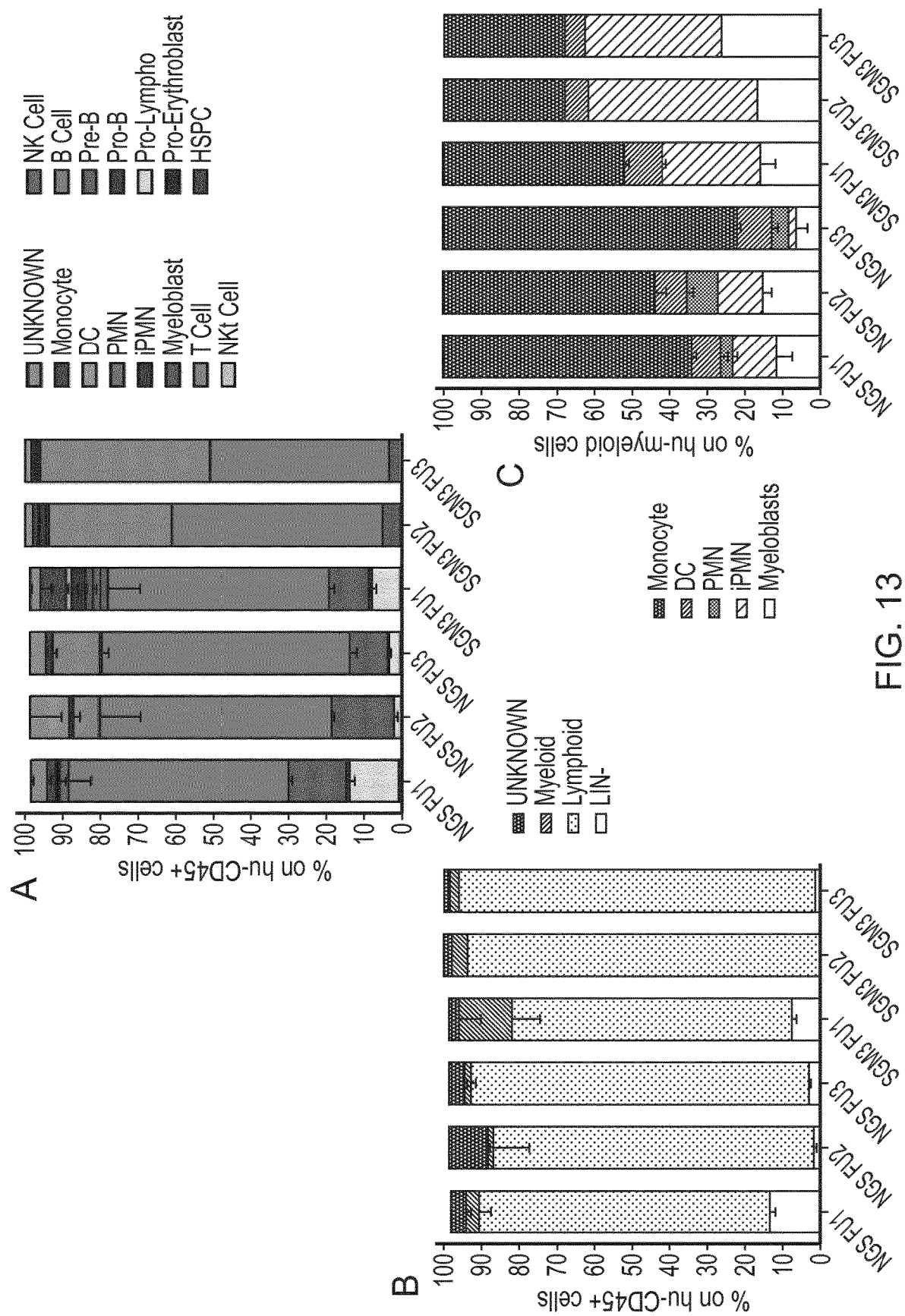
Figure 13:
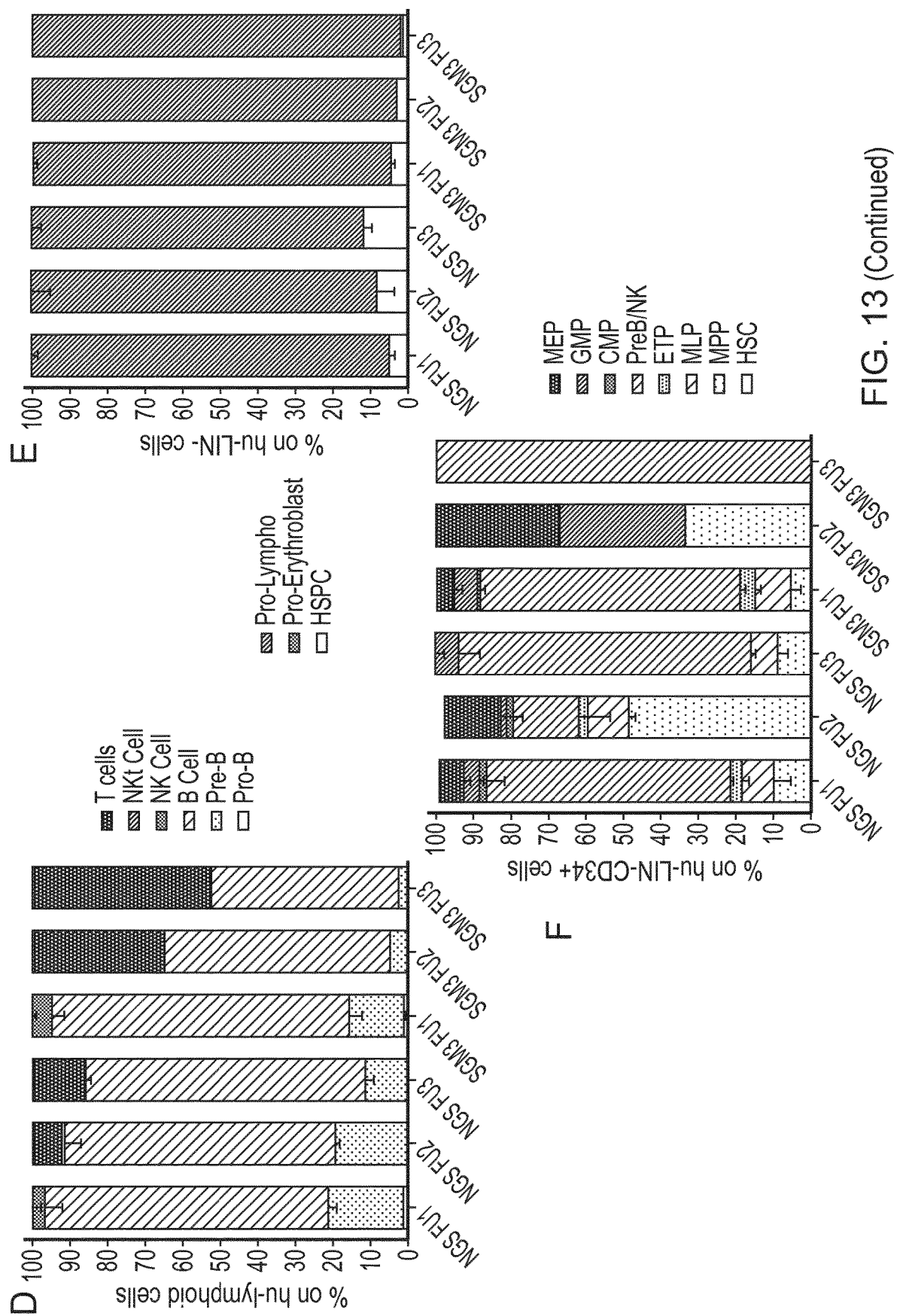
Figure 14:
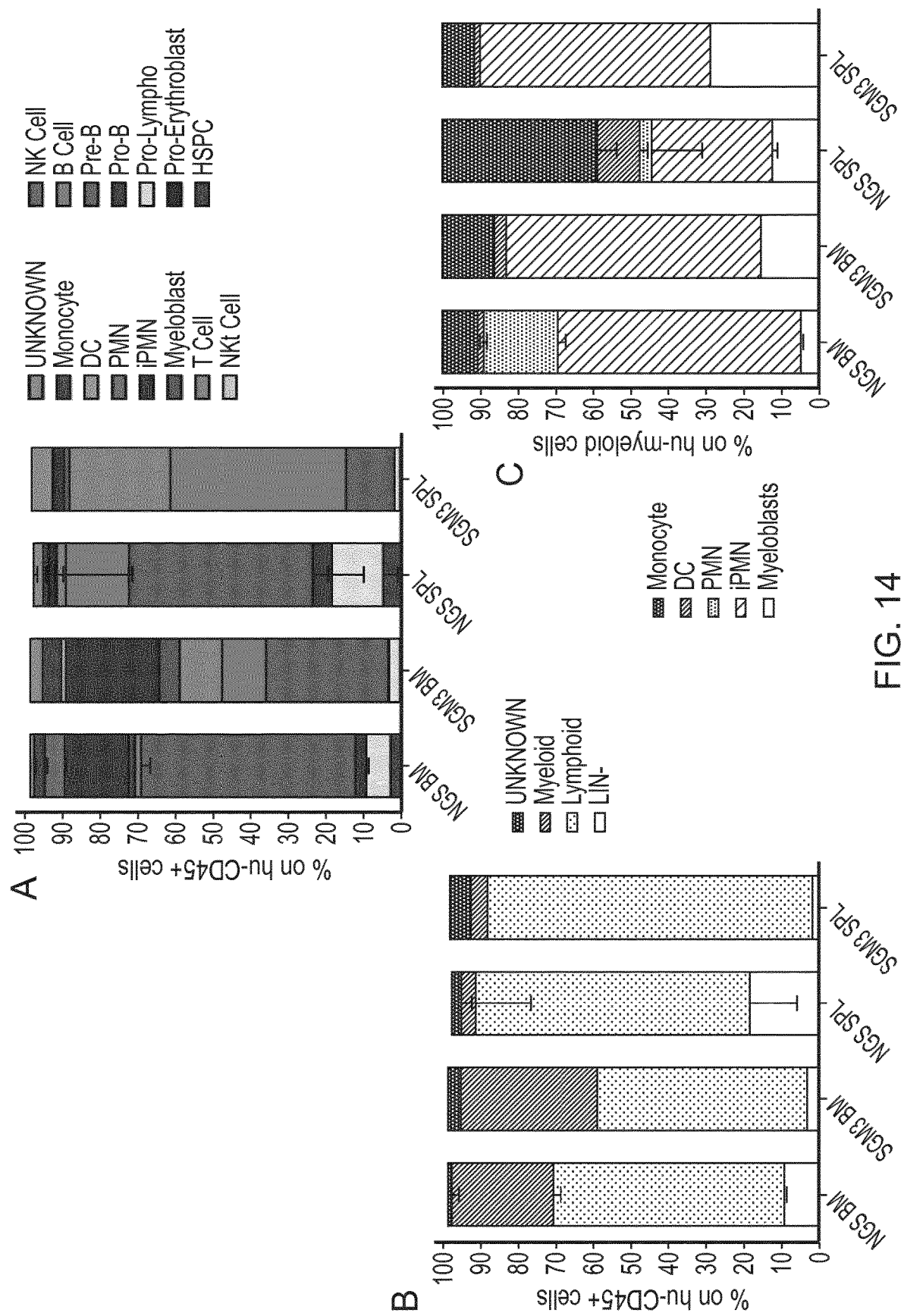
Figure 14:
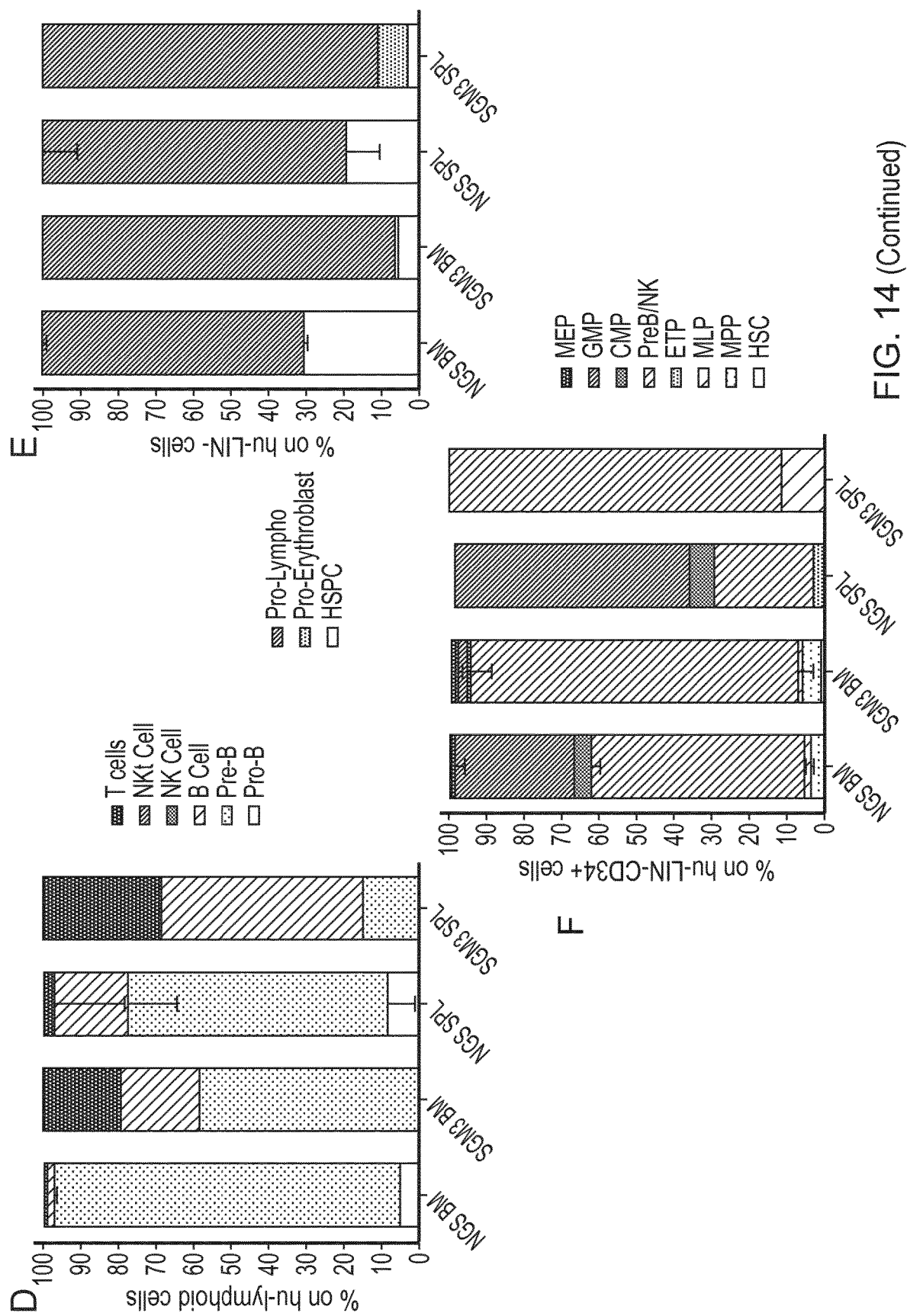
Figure 15:
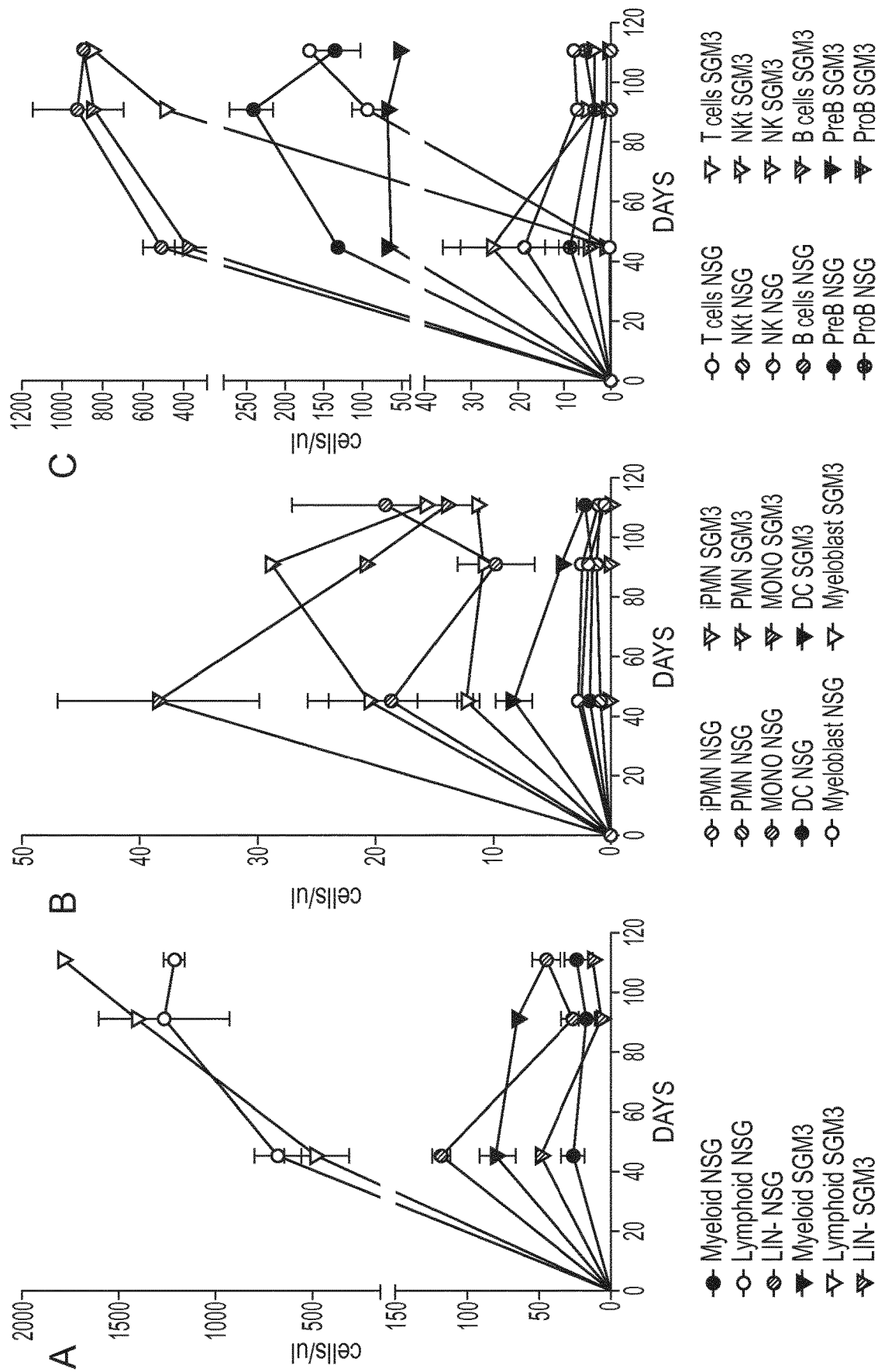

The protocol of the invention allows comprehensively investigating the dynamics of hematopoietic reconstitution in PB of transplanted mice without the requirement of high amounts of blood sample. Indeed we could assess the output of engrafted HSPC in both mouse models, with the expected higher short-term myeloid output in the SGM3 mice with respect to classical NSG mice (FIG. 12-14), and the recovery of B and T lymphocytes. Focusing on the HSPC compartment, through the protocol of the invention we estimated also the contribution of circulating HSPC and the HSPC composition in the BM of mice at sacrifice (FIGS. 13F and 14F). Importantly, the addition of count beads in the protocol's design allows retrieving information on the hematopoietic cell dynamics not only as relative frequencies but also as absolute numbers, increasing the power of the protocol's application in the xeno-transplant (FIG. 12D and FIG. 15).

Example 9

Another important aspect of the Whole Blood Dissection (WBD) technology is its possible use as a starting analysis for additional characterisation of specific cell compartments. For example, the T cell lymphocytes comprise several sub-populations with diverse immunological functions. Thus, in order to have an immunological perspective of a blood sample without losing the comprehensiveness offered by WBD, we designed an additional panel of marker-fluorochromes starting from the same gating strategy and markers used in the WBD setting for the identification of the lymphoid compartment.

Figure 16:
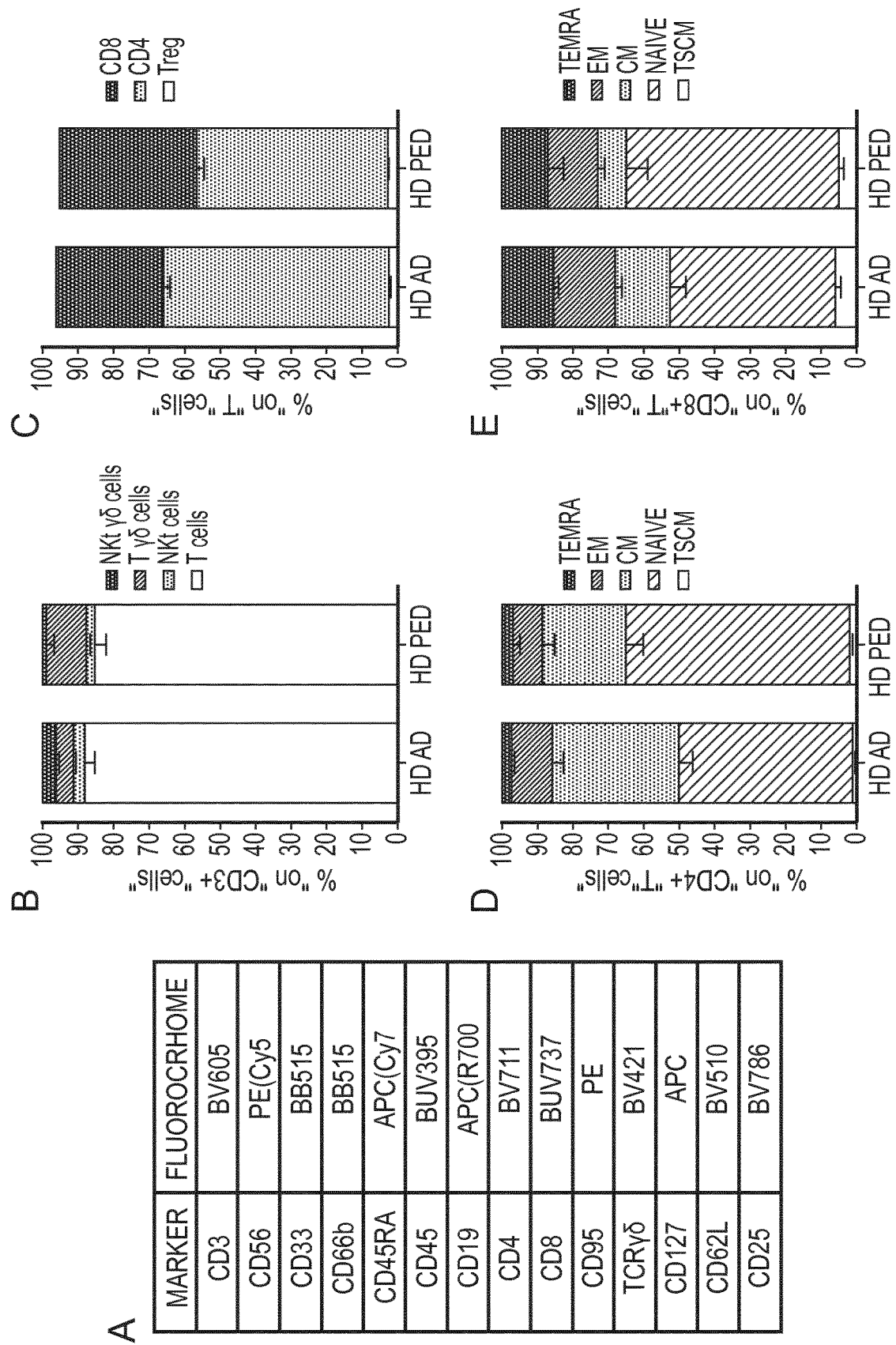

As shown in FIG. 16 we could discriminate B cells, T cells and NKt cells in the lymphoid compartment and additional T cell sub-populations (Treg, CD4+ T cells and CD8+ T cells) and their differentiation state (Naïve, Memory) in Ad and Ped HD.

Since we started from the same gates identified for WBD, we could also assess the absolute number and the frequency for the total sample of each sub-population by combining the information derived from WBD and from this additional staining.

Example 10

Study Design and Materials and Methods
Study Design

For phenotypic analyses of BM and PB from healthy donors (HD), the sample size was determined by the number of adult and paediatric HD for whom excess material was available after informed consent for a research protocol approved by the Ethical Committee at San Raffaele Scientific Institute. It was aimed to collected samples from at least four different healthy donors for each group. Samples from Wiskott-Aldrich Syndrome (WAS), adenosine deaminase deficiency severe combined immunodeficiency (ADA-SCID), and Metachromatic leukodystrophy (MLD) patients were collected, after informed consent, for diagnostic purposes at Ospedale San Raffaele in Milan.

All untreated patients for whom in vivo biological material was available during years 2015-2016 was characterized. Technically validated results were always included to the analyses and no exclusion criteria for outliers were applied. The haematologist involved in the morphological evaluation of sorted blood cell subpopulations was blinded to the cell type analyzed.

Patients' and Healthy Donors' Characteristics

The groups of adult and paediatric HD consisted of five adult HD (Ad HD) and five pediatric HD (Ped HD), with an average age of 25 years and 10 years respectively. The group of ADA-SCID patients consisted of seven ADA-SCID affected individuals (average age=3 years). Six WAS subjects with different ages (range: 2.5-34 years) and disease phenotype were also analysed. The group of MLD patients consisted of six pre-symptomatic late-infantile pediatric patients (range: 7-11 months).

For additional details on patients' characteristics see also Table 5.

Four samples from leukemic patients were analysed: acute myeloid lukemia (AML) patient 1 was analysed at diagnosis (93% of blasts); AML patient 2 was analysed at relapse (66% of blasts). AML patient 3 and the acute lymphoblastic lukemia (ALL) patient were analysed after chemotherapy (9.9% and 10% of blasts respectively) (see also Table 6). Biological samples were obtained from patients, with approval of the San Raffaele Scientific Institute's Ethics Committee and consent from parents or subjects.

Cell Staining and Data Acquisition

Peripheral blood and bone marrow aspirate were collected using vacutainers containing K2EDTA 5.4 mg (Becton Dickinson (BD) Vacutainer®; REF no. 8019839). Cell staining, data acquisition and analyses were performed according to the protocol of Example 1. In brief, after RBC lysis, the samples were labelled with fluorescent antibodies against CD3, CD56, CD14, CD61/41, CD135, CD34, CD45RA (Biolegend) and CD33, CD66b, CD38, CD45, CD90, CD10, CD11c, CD19, CD7 and CD71 (BD Biosciences). Titration assays were performed to assess the best antibody concentration. After surface marking, the cells were incubated with propidium iodide (Biolegend) to stain dead cells. All samples were acquired through BD LSR-Fortessa (BD Bioscience) cytofluorimeter after Rainbow beads (Spherotech) calibration and raw data were collected through DIVA software (BD Biosciences).

Cell Sorting and Morphological Evaluation

To isolate the different hematopoietic cell subtypes for morphological validation we set up five different sorting strategies. Sorting 1 was performed to isolate T, NKT, NK and all CD19+ cells. Sorting 2 was performed to isolate mature B cells, Pre-B and Pro-B precursors. Sorting 3 was performed to isolate PMN, iPMN, Monocytes and DCs. Sorting 4 was performed to isolate erythroblasts and myeloblasts. Sorting 5 was performed to isolate pro-erythroblasts and lymphoid-committed progenitors (Pro-Lymphocytes). The list of the markers used in each sorting panel is shown on FIG. 2A.

Morphological validation was performed on BM samples from HD. The samples were prepared according to the steps 1-12 described in the of Example 1, except that for sorting 3 as monocytes are very sensitive to manipulations and their isolation required a different protocol.

The monocyte isolation protocol required, after the lysis step, two rounds of platelets elimination through centrifugation at 160 rcf RT for 10 minutes. Additionally, in order to keep the monocytes alive, the WS buffer instead of PBS-FACS for all the steps and we worked on ice. All the samples were FACS-purified by MoFlo-XDP cell sorter (Beckman Coulter). The cells were immobilized immediately after sorting onto glass microscope slides by cytospin (Cytospin3, Shandon) centrifugation and then coloured with May-Grunwald/Giemsa (Sigma) staining. Images were collected using Axioskop40 microscope and AxioCam MRc5 camera and analysed through Axiovision 4.8 Software (Zeiss). Morphological evaluation was performed in blind by a specialized hematologist.

Precision Count Beads Validation

To allow the quantification of cells composing the analyzed samples, 50 µl of Precision Count Beads™ (Biolegend) were added before the lysis step.

According to the following formula it is possible to calculate the cell count of the sample analyzed (Cs), when the starting amount of blood sample (Vs), beads solution (Vb), the concentration of beads (Cb), the number of cell (Es) and beads (Eb) events acquired are known.

$$C_s = \frac{V_b \times E_s}{V_s \times E_b} \times C_b$$

To validate the use of Count Beads for the absolute cell number measurement, we performed on 3 Healthy Donor PB samples, whole blood PB serial dilution into PBS adding the same amount of Count Beads and we calculated the $R^2$ of the linear regression.

Human-In-Mouse HSPC Transplantations

NOD.Cg-Prkdc$^{scid}$ II2rg$^{tm1Wjl}$/SzJ (NSG) mice and NOD-scid II2rg$^{null}$-3/GM/SF (SGM3) mice were purchased from the Jackson Laboratory (Charles River Italia, Lecco, Italy) and maintained in specific pathogen-free conditions at Charles River Animal Facility. Human CD34+ cord blood (CB)-derived cells were used for in vivo analysis due to the low number of cells required to generate engraftment. Frozen CB CD34+ cells (Lonza) were thawed and resuspended in sterile PBS without Calcium and Magnesium (Gibco) to a final concentration of $3 \times 10^6$ cells/ml. 8-week old NSG (n=3) and 3SGM (n=3) mice were sub-lethally irradiated at 175 RAD, 3 hours prior to transplant. 300.000 CD34+ cells/mouse were administered in the tail vein and peripheral blood was collected at 6 weeks (FU1) and 13 weeks (FU2) after transplant. At 16 weeks (FU3) mice were euthanized and peripheral blood, spleen (SPL) and bone marrow were collected. PB, SPL and BM samples were lysed using Ammonium Chloride solution (ACK) lysis buffer (STEM-CELL) and stained according to the protocol of Example 1. Before the addition of the human antibodies mix, lysed samples were incubated with mouse purified Rat anti-mouse CD16/CD32 (mouse BD Fc Block™) solution (BD Bioscience) for 10 minutes at room temperature, to avoid unspecific binding to murine cells.

Statistical Analysis

Statistical analyses were performed with Prism 6.0c (GraphPad software). Data are shown as mean±S.E.M., unless otherwise specified. Tables displaying hematopoietic cell subtype frequencies report mean±S.D. Analytical tests for statistical significance among groups employed Mann-Whitney test (P values are specified in each figure legend).

Discussion

As several human blood disorders are associated with an unbalanced distribution of hematopoietic cells in both PB and BM, the generation of tools for the analysis of the hematopoietic system composition remains one crucial goal to understand the causes of haematological diseases, to design novel therapeutic approaches and to test their efficacy. A 17-multiparametric assay has been developed in the past for analyzing in detail PB mature cells. However this earlier protocol could not discriminate progenitor cells and therefore its application could not be extended to BM samples. Additionally, the previous assay could not benefit from the recent advancement in the fluorochromes design that makes the protocol of the invention up-to-date with the most recent technology favoring its future exploitation. The low amount of blood required to achieve a comprehensive picture of the hematopoietic composition of a given sample makes the protocol of the invention suitable for clinical screening when limited amounts of starting material are available. When tested on samples from adult and pediatric healthy donors, the protocol of the invention proved its sensitivity. Although we observed a similar cellular distribution among the different leukocyte compartments in adult (Ad) and pediatric (Ped) healthy donors (HD) (FIG. 3B and FIG. 8A-B), we could detect the known subtle age-related differences in the hematopoietic composition, particularly regarding the lymphoid immature B cell lineages (28.5% vs. 17.4% Pre-B cells on lymphocytes in Ped HD and in Ad HD respectively, FIG. 3B and FIG. 8D). This difference was found further accentuated in the very young individuals affected by MLD (FIG. 3D and FIG. 8D), where we found a higher content of immature B cells as compared to Ad HD (FIG. 8D-E). We also tested the application of the protocol to comprehensively analyze the human-in-mouse graft in NSG and SGM3 mice transplanted with CB HSPC. By analyzing PB, SPL and BM of transplanted mice we could assess the composition and the absolute number of human hematopoietic cells generated from engrafted HSPC (FIG. 13-15). Moreover, the presence of HSPC-specific markers allowed also the measurement of circulating and BM-resident HSPC (FIG. 13E-F, FIGS. 14F and 15F). The combination of this information with the dynamics of mature human cells, makes the protocol of the invention a unique tool to comprehensively study human HSPC behavior in animal models, fundamental for assessing the safety and efficacy of treatments and for studying the biology of human hematopoietic system.

In order to further validate the protocol's efficacy in detecting hematopoietic alterations in clinically relevant settings, we analyzed BM samples from ADA-SCID and WAS patients. We could show that the protocol is capable not only of confirming the previously described hematopoietic alterations occurring in these individuals but also of providing novel information on the hematopoietic landscape of these diseases. Indeed, together with the known defects in B cell contribution (FIG. 3C and FIG. 8D-E Table 7-8), we could observe alterations in HSPC compartment, supporting the notion that the functional impairment causative of these PID also affects the very primitive stem-cell compartment (FIG. 8G and Table 7-8). These findings support the use of the technology as a screening tool for the first characterization of immunodeficiencies, directing the choice of additional assays on specific cellular compartments. In this regard, the protocol could also provide a relevant instrument for the evaluation of the BM composition of donor grafts prior to infusion and could be applied for the characterization of other cell sources enriched in HSPCs, including PB upon administration of mobilizing agents. Additionally, our protocol is suitable for the clinical monitoring of PID patients after allogeneic transplantation or GT to evaluate, at the same time, the level of re-establishment of mature blood cells and the long-term maintenance of all HSPC populations and for studying the dynamics of the hematopoietic reconstitution.

Finally, we tested our technology on samples from leukemic patients, both at diagnosis/relapse and after treatments (Table 6). We could clearly identify the blast populations and categorize the types of leukemia even in the samples with low blast content. Indeed, we found that the four leukemic samples at acute phases displayed a highly skewed repertoire with respect to HD and a clear myeloid phenotype (FIG. 4-5). On the other hand, in the samples analyzed after chemotherapy, we could identify residual myeloid and lymphoid leukemic blasts and evaluate their contribution, which was to levels comparable to the estimations made through the standard diagnostic assays (FIG. 4C-D, Table 6). Moreover, the protocol of the invention was able to detect the presence of a large fraction of previously unidentified cells with "plasmablast-like" phenotype in the MM BM sample (FIG. 4E-5E), suggesting that the technology of the invention is capable of providing a first categorization of the BM of leukemic patients that could guide investigators towards more detailed down-stream analyses. Importantly, the presence of antibodies specific for the HSPC subtypes represents a substantial advantage of the invention over the standard phenotypic characterizations allowing identifying with higher precision the level of maturation of the leukemic blasts. Indeed, through the protocol of the invention we showed that AML-1 and AML-4 displayed a more immature phenotype with respect to AML-2 and AML-3 (FIG. 4B-5B). Thus, this technology can provide in less than two hours important and timely readouts for directing therapeutic strategies on hospitalized individuals. Of note, by analyzing the phenotype of the residual blasts in two different AML patients (AML-5 and AML-6, FIG. 4) after chemotherapy, we could observe a diverse degree of differentiation of chemo-resistant blasts, with AML-5 displaying a "CMP-like" phenotype, while AML-6 showing a "HSC/MPP-like" phenotype. One could speculate that the protocol of the invention may provide a tool for the detection of Leukemic stem cells (LSC) which represent a subset of AML cells showing an early stem/progenitor phenotype with the potential of preserving the leukemic population and generate relapses after treatment.

The capability of the protocol of the invention of detecting residual clones in patients who underwent chemotherapy or BMT suggests that this technique could be also potentially exploited for the monitoring of Minimal Residual Disease (MRD). MRD tracking is currently performed by assessing the so-called Leukemia Associated Aberrant Immunophenotype at diagnosis and monitoring it during the patient follow-up after treatments, but a major disadvantage of this approach is the current lack of uniformity on performing this assay among centers. Once implemented, the standardized and reproducible nature of the protocol of the invention could overt these intrinsic constraints providing a common platform to reduce at minimum inter-laboratory variability. Overall, we believe that the protocol of the invention, allowing the simultaneous analysis of 23 different cell types including all the major mature lineage compartments, progenitors at different stages of maturation and rare subsets of HSPC, constitute a novel relevant tool for the analysis of PB and BM samples. The protocol has substantial advantages on the analysis of HSPC compartment with respect to current technologies based on CD34+ isolation and purification, which might introduce analytical biases and negatively affect the cell yield. The possibility through the protocol of the invention to analyze at the same time HSPC and mature cells starting from very small amounts of BM or PB allows studying the composition of human hematopoietic progenitors in different experimental settings like at steady-state hematopoiesis or upon stressed conditions, such as the ones related to hematopoietic defects, hematological tumors, pharmacological therapies, bone marrow transplantations and gene therapy. Importantly, the protocol of the invention could represent a useful tool for preclinical studies involving the use of humanized animal models where investigators might aim at analyzing small changes in BM and PB human blood cell composition upon treatment. Finally, it is relevant to underline the plasticity of the protocol's design. The high number of markers present in the protocol can be exploited to investigate several possible gating strategies and marker combination to focus on specific compartments. One example is the alternative gating strategy described in FIG. 9 that focuses on CD34+ population and allows dissection of LIN+CD34+ and HSPC subsets (FIG. 10). Moreover, the continuous update of hematopoietic subsets definition can also be overcome through the protocol of the invention. Indeed, recent works describe both novel erythroid progenitors using CD71 marker and a CMP subset with megakaryocytic potential identifiable through CD41 marker. Since both CD71 and anti-CD41/CD61 antibodies are present in the marker panel we can propose the protocol of the invention as capable of identifying these newly described subpopulations, updating the definition of progenitors composing the HSPC compartment.

In conclusion, the protocol of the invention allows unambiguously identifying >99% of the cell subpopulations composing a blood sample in a reproducible, standardized, cost- and time-efficient manner. This technology represents a powerful tool for the analysis of human hematopoiesis with a wide spectrum of potential pre-clinical and clinical applications.

REFERENCES

1. E. G. van Lochem, V. H. J. van der Velden, H. K. Wind, J. G. to Marvelde, N. A. C. Westerdaal, J. J. M. van Dongen, Immunophenotypic differentiation patterns of normal hematopoiesis in human bone marrow: reference patterns for age-related changes and disease-induced shifts, Cytometry B. Clin. Cytom. 60, 1-13 (2004).

2. F. E. Craig, K. A. Foon, Flow cytometric immunophenotyping for hematologic neoplasms, Blood 111, 3941-3967 (2008).

3. B. Cham, M. A. Bonilla, J. Wnkelstein, Neutropenia associated with primary immunodeficiency syndromes, Semin. Hematol. 39, 107-112 (2002).

4. S. G. Apasov, M. R. Blackburn, R. E. Kellems, P. T. Smith, M. V Sitkovsky, Adenosine deaminase deficiency increases thymic apoptosis and causes defective T cell receptor signaling, J. Clin. Invest 108, 131-141 (2001).

5. A. V Sauer, H. Morbach, I. Brigida, Y. Ng, A. Aiuti, E. Meffre, Defective B cell tolerance in adenosine deaminase deficiency is corrected by gene therapy, 122, 2141-2152 (2012).

6. I. Brigida, A. V Sauer, F. Ferrua, S. Giannelli, S. Scaramuzza, V. Pistoia, M. C. Castiello, B. H. Barendregt, M. P. Cicalese, M. Casiraghi, C. Brombin, J. Puck, K. Muller, L. D. Notarangelo, D. Montin, J. M. Van Montfrans, M. G. Roncarolo, E. Traggiai, J. J. M. Van Dongen, M. Van der Burg, A. Aiuti, B-cell development and functions and therapeutic options in adenosine deaminase—deficient patients, J. allergy Clin. Immunol. 133, 799-806 (2014).

7. K. L. Simon, S. M. Anderson, E. K. Garabedian, D. Moratto, R. A. Sokolic, F. Candotti, Molecular and phenotypic abnormalities of B lymphocytes in patients with Wiskott-Aldrich syndrome, J. Allergy Clin. Immunol. 133, 896-899.e4 (2014).

8. H. D. Ochs, S. J. Slichter, L. A. Harker, W. E. Von Behrensm, R. A. Clark, R. J. Wedgwood, The Wiskott-Aldrich Syndrome: Studies of Lymphocytes, Granulocytes, and Platelets, Blood 55, 243-252 (1980).

9. J. Y. Park, M. Kob, A. P. Prodeus, F. S. Rosen, A. Shcherbina, E. Remold-O'Donnell, Early deficit of lymphocytes in Wiskott-Aldrich syndrome: Possible role of WASP in human lymphocyte maturation, Clin. Exp. Immunol. 136, 104-110 (2004).

10. M. J. Massaad, N. Ramesh, R. S. Geha, Wiskott-Aldrich syndrome: A comprehensive review, Ann. N. Y. Acad. Sci. 1285, 26-43 (2013).

11. I. De Kouchkovsky, M. Abdul-Hay, "Acute myeloid leukemia: a comprehensive review and 2016 update," Blood Cancer J. e441, 1-10 (2016).

12. E. Jabbour, S. O'Brien, M. Konopleva, H. Kantarjian, New Insights into the Pathophysiology and Therapy of Adult Acute Lymphoblastic Leukemia, Cancer, 2517-2528 (2015).

13. S. P. Hunger, C. G. Mullighan, Acute Lymphoblastic Leukemia in Children, N. Engl. J. Med. 373, 1541-1552 (2015).

14. D. Bhojwani, J. J. Yang, C.-H. Pui, Biology of Childhood Acute Lymphoblastic Leukemia, Pediatr. Clin. North Am. 62, 47-60 (2015).

15. E. Oliveira, T. S. Bacelar, J. Ciudad, M. C. M. Ribeiro, D. R. N. Garcia, L. Sedek, S. F. Maia, D. B. Aranha, I. C. Machado, A. Ikeda, B. F. Baglioli, N. Lopez-Duarte, L. A. C. Teixeira, T. Szczepanski, M. L. M. Silva, M. G. P. Land, A. Orfao, E. S. Costa, Altered neutrophil immunophenotypes in childhood B-cell precursor acute lymphoblastic leukemia, Oncotarget 7, 24664-24676 (2016).

16. M. R. O'Donnell, C. N. Abboud, J. Altman, F. R. Appelbaum, D. A. Arber, E. Attar, U. Borate, S. E. Coutre, L. E. Damon, S. Goorha, J. Lancet, L. J. Maness, G. Marcucci, M. M. Millenson, J. O. Moore, F. Ravandi, P. J. Shami, B. D. Smith, R. M. Stone, S. A. Strickland, M. S.

Tallman, E. S. Wang, M. Naganuma, K. M. Gregory, Acute Myeloid Leukemia, *Natl. Compr. Cancer Netw.* 10, 984-1021 (2012).

17. A. Porwit, A. Rajab, Flow cytometry immunophenotyping in integrated diagnostics of patients with newly diagnosed cytopenia: one tube 10-color 14-antibody screening panel and 3-tube extensive panel for detection of MDS-related features, Int. J. Lab. Hematol. 37, 133-143 (2015).

18. M.-C. Jacob, A. Souvignet, J. Pont, F. Solly, J. Mondet, S. Kesr, M. Pernollet, C. Dumestreerard, L. Campos, J.-Y. Cesbron, One tube with eight antibodies for 14-part bone marrow leukocyte differential using flow cytometry, *Cytometry B. Clin. Cytom.* 00, 1-11 (2016).

The invention claimed is:

1. A kit for identifying, determining the relative frequency of and/or quantifying the number of cells within hematopoietic cell subtypes comprising (i) an anti-CD3 antibody, (ii) an anti-CD56 antibody, (iii) an anti-CD14 antibody, (iv) an anti-CD38 antibody, (v) an anti-CD45 antibody, (vi) an anti-CD90 antibody, (vii) an anti-CD135 antibody, (viii) an anti-CD10 antibody, (ix) an anti-CD11c antibody, (x) an anti-CD19 antibody, (xi) an anti-CD34 antibody, (xii) an anti-CD45RA antibody, (xiii) an anti-CD7 antibody, (xiv) an anti-CD71 antibody, (xv) an anti-CD41/CD61 complex antibody or an anti-CD41 antibody and/or an anti-CD61 antibody, and (xvi) an anti-CD33 antibody and/or an anti-CD66b antibody, wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome;

optionally, wherein the kit further comprises (B-i) an anti-CD3 antibody, (B-ii) an anti-CD56 antibody, (B-iii) an anti-CD45 antibody, (B-iv) an anti-CD19 antibody, (B-v) an anti-CD45RA antibody, (B-vi) an anti-CD33 antibody and/or an anti-CD66b antibody, (B-vii) an anti-CD4 antibody, (B-viii) an anti-CD8 antibody, (B-ix) an anti-CD95 antibody, (B-x) an anti-TCRγδ antibody, (B-xi) an anti-CD127 antibody, (B-xii) an anti-CD62L antibody, (B-xiii) an anti-CD25 antibody, wherein each of (B-i) to (B-xiii) is labelled with a different fluorochrome, wherein when (B-vi) is an anti-CD33 antibody and an anti-CD66b antibody, the anti-CD33 antibody and anti-CD66b are labelled with the same fluorochrome optionally, wherein the kit further comprises microspheres for providing an internal counting standard;

optionally wherein the kit further comprises a red blood cell lysis buffer.

2. The kit according to claim 1, wherein (xv) is an anti CD41/CD61 complex antibody; and/or wherein (xvi) and/or (B-vi) is an anti-CD33 antibody and an anti-CD66b antibody.

3. The kit according to claim 1, further comprising a fluorescent cell viability marker.

4. A composition for identifying, determining the relative frequency of and/or quantifying the number of cells within hematopoietic cell subtypes comprising (i) an anti-CD3 antibody, (ii) an anti-CD56 antibody, (iii) an anti-CD14 antibody, (iv) an anti-CD38 antibody, (v) an anti-CD45 antibody, (vi) an anti-CD90 antibody, (vii) an anti-CD135 antibody, (viii) an anti-CD10 antibody, (ix) an anti-CD11c antibody, (x) an anti-CD19 antibody, (xi) an anti-CD34 antibody, (xii) an anti-CD45RA antibody, (xiii) an anti-CD7 antibody, (xiv) an anti-CD71 antibody, (xv) an anti CD41/CD61 complex antibody or an anti-CD41 antibody and/or an anti-CD61 antibody, and (xvi) an anti-CD33 antibody and/or an anti-CD66b antibody, wherein each of (i) to (xvi) is labelled with a different fluorochrome, wherein when (xvi) is an anti-CD33 antibody and an anti-CD66b antibody, the anti-CD33 antibody and anti-CD66b are labelled with the same fluorochrome, and wherein when (xv) is an anti-CD41 antibody and an anti-CD61 antibody, the anti-CD41 antibody and the anti-CD61 antibody are labelled with the same fluorochrome.

5. The composition according to claim 4, wherein (xv) is an anti CD41/CD61 complex antibody; and/or wherein (xvi) and/or (B-vi) is an anti-CD33 antibody and an anti-CD66b antibody.

6. The composition according to claim 4, further comprising a fluorescent cell viability marker.

* * * * *